(12) United States Patent
Wu et al.

(10) Patent No.: US 9,856,264 B2
(45) Date of Patent: Jan. 2, 2018

(54) ISOQUINOLINESULFONYL DERIVATIVE AS RHO KINASE INHIBITOR

(71) Applicant: MEDSHINE DISCOVERY INC., Nanjing, Jiangsu (CN)

(72) Inventors: Lingyun Wu, Shanghai (CN); Yuanshan Yao, Shanghai (CN); Zhaoguo Chen, Shanghai (CN); Shuhui Chen, Shanghai (CN)

(73) Assignee: Medshine Discovery Inc., Jiangsu (CN)

( * ) Notice: Subject to any disclaimer, the term of this patent is extended or adjusted under 35 U.S.C. 154(b) by 0 days.

(21) Appl. No.: 15/306,965

(22) PCT Filed: Apr. 21, 2015

(86) PCT No.: PCT/CN2015/077045
§ 371 (c)(1),
(2) Date: Oct. 26, 2016

(87) PCT Pub. No.: WO2015/165341
PCT Pub. Date: Nov. 5, 2015

(65) Prior Publication Data
US 2017/0037050 A1    Feb. 9, 2017

(30) Foreign Application Priority Data

Apr. 28, 2014  (CN) .................. 2014 1 0174893
Apr. 16, 2015  (CN) .................. 2015 1 0182758

(51) Int. Cl.
| | |
|---|---|
| A61K 31/437 | (2006.01) |
| C07D 487/04 | (2006.01) |
| A61K 31/4725 | (2006.01) |
| A61K 31/55 | (2006.01) |
| C07D 401/12 | (2006.01) |
| C07D 471/04 | (2006.01) |

(52) U.S. Cl.
CPC ........ *C07D 487/04* (2013.01); *A61K 31/4725* (2013.01); *A61K 31/55* (2013.01); *C07D 401/12* (2013.01); *C07D 471/04* (2013.01)

(58) Field of Classification Search
CPC ............. A61K 31/437; A61K 31/4725; C07D 401/12; C07D 471/02
USPC .................... 514/307, 300; 546/139, 113
See application file for complete search history.

(56) References Cited

U.S. PATENT DOCUMENTS

| | | | | |
|---|---|---|---|---|
| 4,456,757 | A | * | 6/1984 | Hidaka ................ C07D 217/02 544/128 |
| 7,572,913 | B2 | | 8/2009 | McKerracher et al. |
| 7,964,613 | B2 | | 6/2011 | Matsubara et al. |
| 8,415,372 | B2 | | 4/2013 | Yamada et al. |
| 2005/0014783 | A1 | | 1/2005 | Dole et al. |

FOREIGN PATENT DOCUMENTS

| | | |
|---|---|---|
| CN | 1980929 A | 6/2007 |
| CN | 101253166 A | 8/2008 |
| CN | 101622243 A | 1/2010 |
| CN | 101730690 A | 6/2010 |
| CN | 102993178 A | 3/2013 |

OTHER PUBLICATIONS

Berge, Stephen M., etc.; Pharmaceutica Salts; Journal of Pharmaceutical Sciences, vol. 66, No. 1, Jan. 1977, 1-19.
Maehr, Hubert; A Proposed Hew Convention for Graphic Presentation of Molecular Geometry and Topography; Journal of Chemical Education, vol. 62, No. 2, Feb. 1965.
Remington: The Science and Practice of Pharmacy, 21st Ed., Lippincott, Williams & Wilkins 2005.
Chinese Priority Patent Application No. 201410174893.1 (not published) with translation.
Chinese Priority Patent Application No. 201510182758.6 (not published) with translation.
Jul. 9, 2015 International Search Report issued in International Patent Application No. PCT/CN20151077045, total 3 pages in English.
Written Opinion of ISA/CN, International Search Report dated Jul. 9, 2015 in International Application No. PCT/CN2015/077045, total 3 pages in English.

* cited by examiner

*Primary Examiner* — Charanjit Aulakh
(74) *Attorney, Agent, or Firm* — Harness, Dickey & Pierce, P.L.C.

(57) ABSTRACT

The present invention discloses a class of isoquinolinesulfonyl derivatives as RHO kinase inhibitors, and pharmaceutical compositions thereof, and relates to pharmaceutically acceptable uses thereof. Specifically, the present invention relates to a compound as represented by formula (I), or a pharmaceutically acceptable salt thereof.

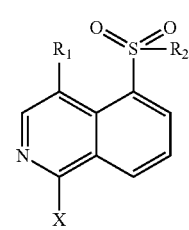

(I)

19 Claims, No Drawings

ISOQUINOLINESULFONYL DERIVATIVE AS RHO KINASE INHIBITOR

CROSS-REFERENCE TO RELATED APPLICATIONS

This application is a National Stage of International Application No. PCT/CN2015/077045, filed on Apr. 21, 2015 and published in Chinese as WO 2015/165341 on Nov. 5, 2015. This application claims the priority to Chinese Application No. 201410174893.1, filed on Apr. 28, 2014 and Chinese Application No. 201510182758.6, filed on Apr. 16, 2015. The entire disclosures of the above applications are incorporated herein by reference.

FIELD OF THE INVENTION

This invention relates to isoquinoline sulfonamide derivatives and its pharmaceutical composition as RHO inhibitors. To be specific, this invention relates to the compounds of formula (I) or pharmaceutically acceptable salts thereof as RHO inhibitors.

BACKGROUND OF THE INVENTION

Fasudil, as a RHO kinase inhibitor, can smooth the blood vessel contraction through reducing the myosin light chain phosphorylation, reduce the tension of endothelial cells, improve the blood microcirculation in the brain, and prevent the occur or aggravation of steal syndrome. At the same time, Fasudil can antagonize the effect of proinflammatory cytokines, protect the neurons from diverse cell death, and promote nerve regeneration. There is evidence to support fasudil hydrochloride in promoting the nerve function recovery and reducing the proportion of disability in clinical. Due to the limited access to healthcare service and the level of awareness of the disease in China rural areas, the ultra early thrombolysis treatment cannot be achieved for most patients. For patients beyond the thrombolysis window, there are limited medical treatment options to reduce further progression of the disease and rebuild local blood circulation. Fasudil has effects on both aspects, and may offer significant neuroprotective and therapeutic effects on ischemic cerebrovascular disease. This study of Fasudil and its analogs may have significant clinical impact to reduce the disability rate and improve the quality of life for stroke patients.

WO2004106325 discloses a series of compounds of the general formula (B-I) belonging to fasudil prodrug.

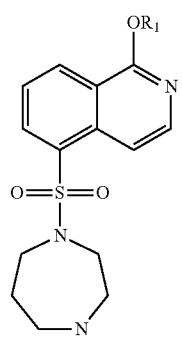

(B-I)

In spite of these prior art compounds can be used as RHO kinase inhibitors, their activity, solubility, pharmacokinetics and other aspects of performance of the aforesaid compounds could be improved.

SUMMARY OF THE INVENTION

An objective of the present invention is to provide a compound of formula (I) or a pharmaceutically acceptable salt thereof,

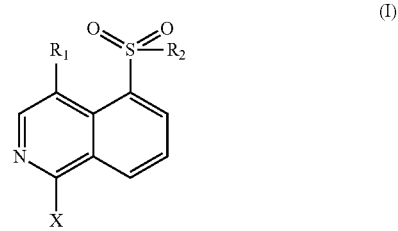

(I)

wherein, $R_1$, X are separately and independently selected from the group consisting of H, F, Cl, Br, I, CN, OH, $NH_2$, $C_{1-3}$alkyl, $C_{1-3}$alkoxy, $C_{1-3}$ alkylamino, and N,N-di($C_{1-3}$alkyl)amino, wherein the $C_{1-3}$alkyl is optionally substituted by $R_{01}$, $R_{01}$ is selected from the group consisting of F, Cl, Br, I, OH, and $NH_2$, the number of $R_{01}$ is 1, 2 or 3;

$R_2$ is selected from the group consisting of

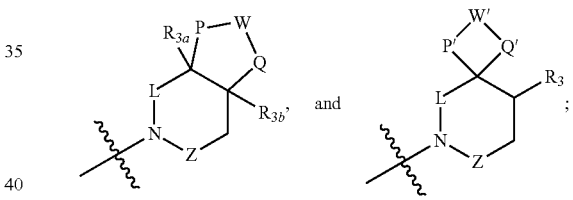

W, W' are separately and independently selected from the group consisting of $N(R_{w1})$, $C(R_{w2})(R_{w3})$ and single bond;
L, Z are separately and independently selected from the group consisting of single bond and $C(R_{z1})(R_{z2})$;
P, P' are separately selected from $(CH_2)_{q1}$;
Q, Q' are separately selected from $(CH_2)_{q2}$;
$q_1$, $q_2$ are separately and independently selected from the group consisting of 0, 1, 2, 3 and 4;
when $q_1$, $q_2$ are selected from 0, $(CH_2)_{q1}$, $(CH_2)_{q2}$ represent single bond;
up to two of P, W, and Q are single bonds simultaneously;
up to two of P', W', and Q' are single bonds simultaneously;
$R_{3a}$, $R_{3b}$, $R_3$, $R_{w1}$, $R_{w2}$, $R_{w3}$, $R_{z1}$, $R_{z2}$ are separately and independently selected from the group consisting of H, F, Cl, Br, I, CN, OH, $NH_2$, $C_{1-3}$alkyl, $C_{1-3}$alkoxy, $C_{1-3}$ alkylamino, and N,N-di($C_{1-3}$alkyl)amino, wherein the $C_{1-3}$alkyl is optionally substituted by $R_{01}$.

In certain embodiment of this invention, the aforesaid $R_{3a}$, $R_{3b}$, $R_3$, $R_{w1}$, $R_{w2}$, $R_{w3}$ are selected from the group, optionally substituted by halogen, hydroxyl and/or amino, consisting of methyl, ethyl and propyl; $R_{01}$ is selected from the group consisting of F, Cl, Br, I, OH, and $NH_2$, the number of $R_{01}$ is 1, 2 or 3.

In certain embodiment of this invention, the aforesaid $R_1$ is selected from the group consisting of H, F, Cl, Br, I, methyl, difluoromethyl, trifluoromethyl, and methoxyl; X is selected from the group consisting of H and OH.

In certain embodiment of this invention, the aforesaid moiety of

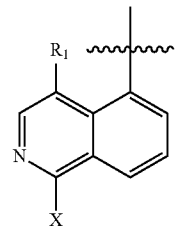

is selected from the group consisting of:

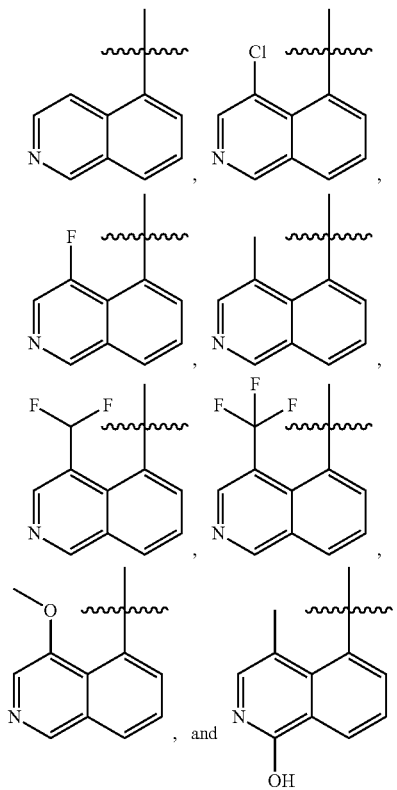

In certain embodiment of this invention, the aforesaid $R_2$ is selected from

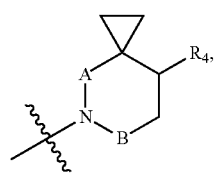

in which, one of A and B is single bond, and the other one is methylene; $R_4$ is selected from the group consisting of H, F, Cl, Br, I, CN, OH, $NH_2$, $C_{1-3}$alkyl, $C_{1-3}$alkoxy, $C_{1-3}$alkylamino, and N,N-di($C_{1-3}$alkyl)amino, wherein the $C_{1-3}$alkyl is optionally substituted by $R_{01}$, $R_{01}$ is selected from the group consisting of F, Cl, Br, I, OH, and $NH_2$, the number of $R_{01}$ is 1, 2 or 3; preferably, $R_4$ is selected from the group consisting of $NH_2$, and ethylamino.

In certain embodiment of this invention, the aforesaid $R_2$ is selected from the group consisting of

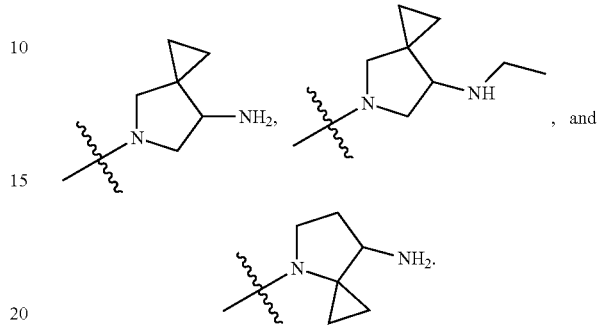

In certain embodiment of this invention, the aforesaid compound or a pharmaceutically acceptable salt thereof, the aforesaid $R_2$ is selected from the group consisting of

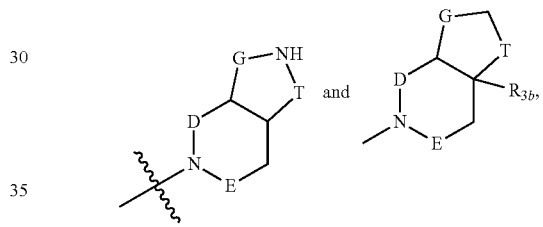

in which, one of D and E is single bond, and the other one is methylene; G is selected from $(CH_2)_g$; T is selected from $(CH_2)_t$; g, t are separately and independently selected from the group consisting of 0, 1, 2, 3 and 4.

In certain embodiment of this invention, the aforesaid g is selected from the group consisting of 1, 2, 3 and 4, t is selected from the group consisting of 0 and 1.

In certain embodiment of this invention, the aforesaid $R_{3b}$ is selected from $NH_2$.

In certain embodiment of this invention, the aforesaid $R_2$ is selected from the group consisting of

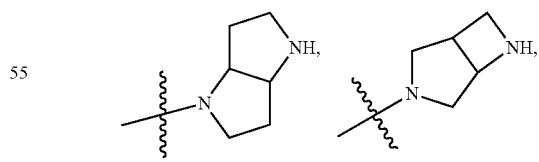

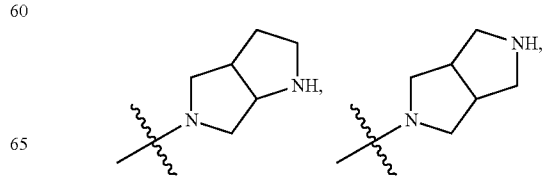

-continued

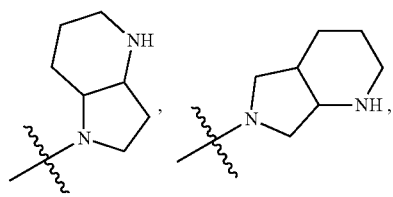 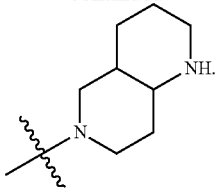

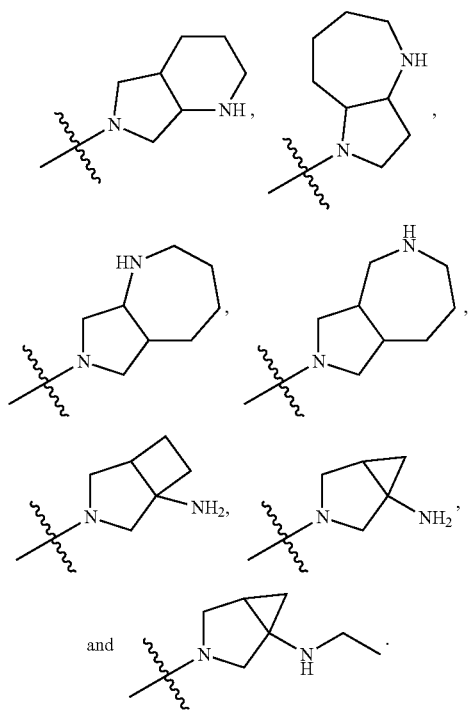

and

In certain embodiment of this invention, the aforesaid $R_2$ is selected from

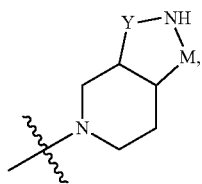

in which, Y is selected from $(CH_2)_y$; M is selected from $(CH_2)_m$; y is selected from the group consisting of 0, 1, 2 and 3; m is selected from the group consisting of 0 and 1.

In certain embodiment of this invention, the aforesaid $R_2$ is selected from the group consisting of

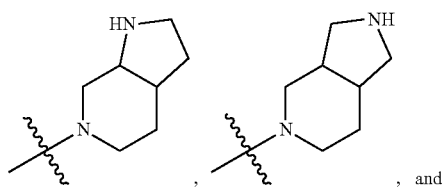, and

-continued

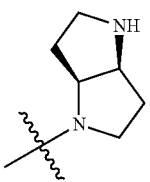

In certain embodiment of this invention, the aforesaid $R_2$ is selected from the group consisting of

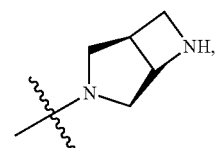

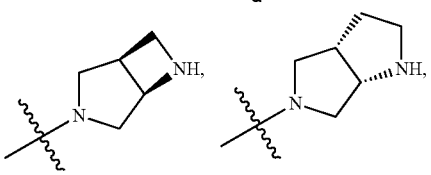

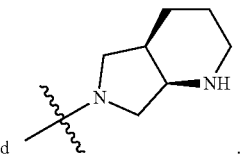

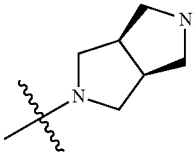 and

In certain embodiment of this invention, the aforesaid compound is selected from the group consisting of:

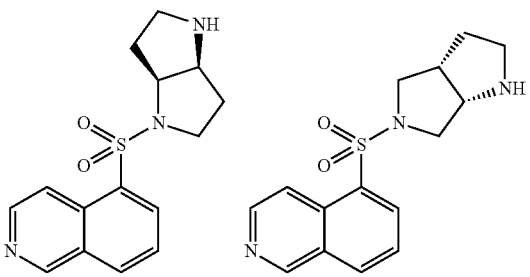

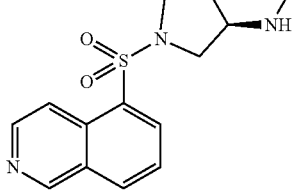

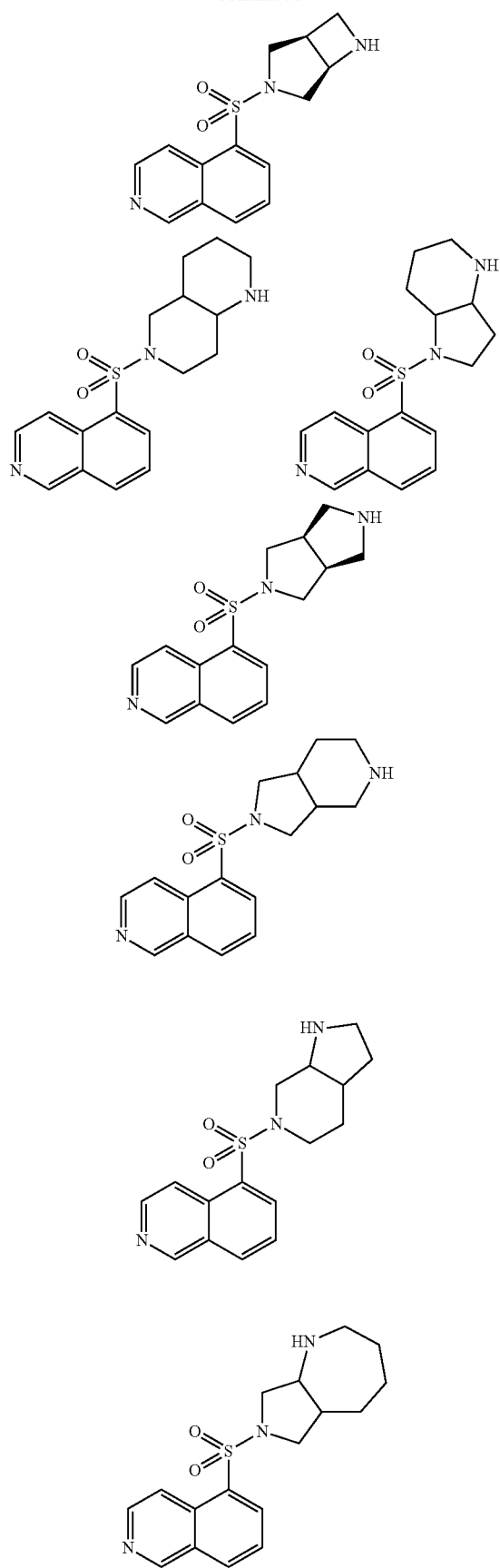
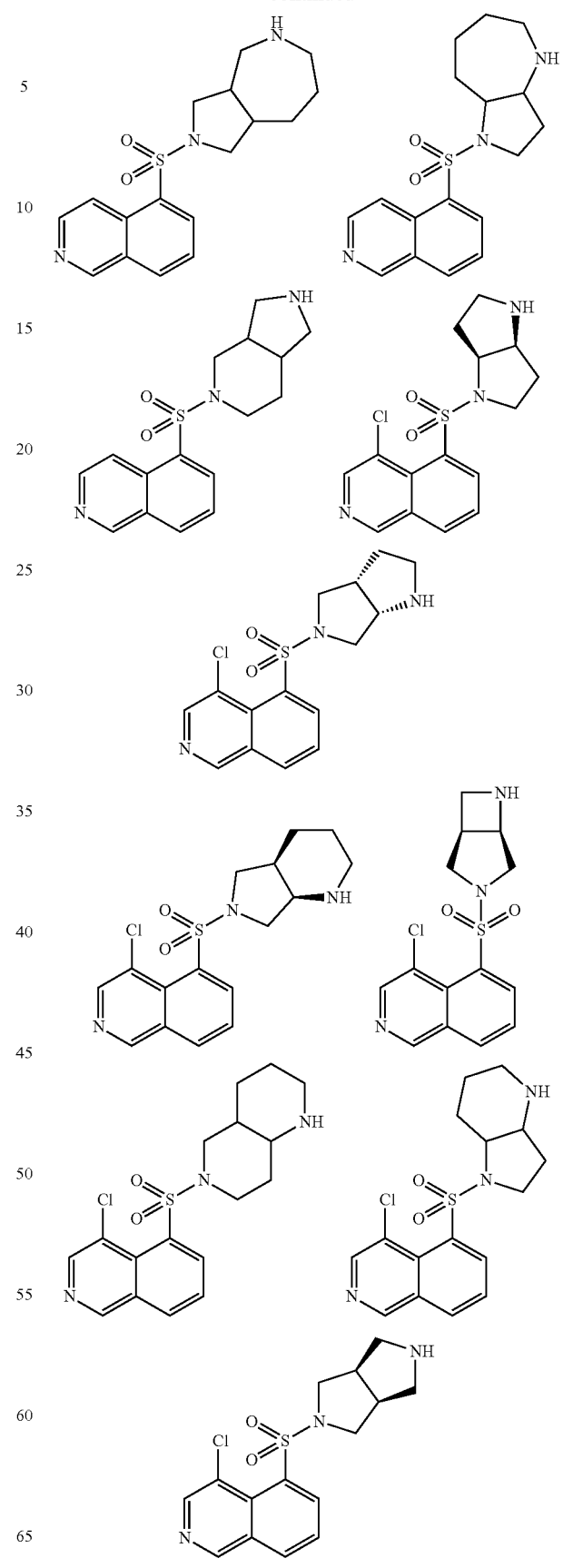

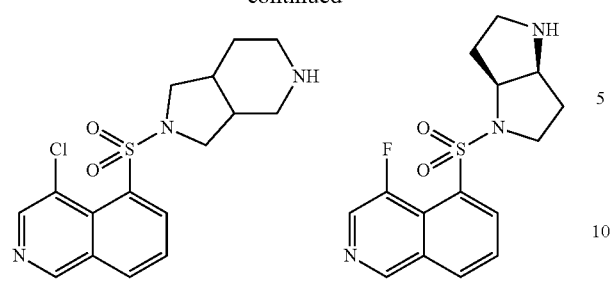
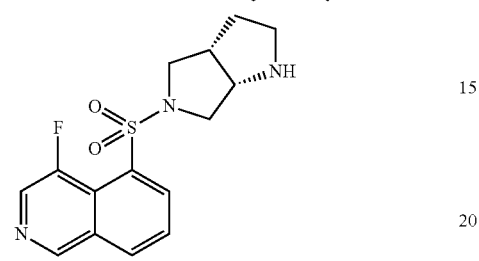
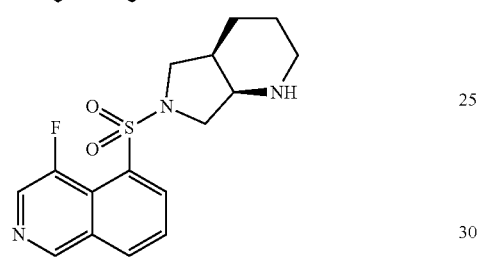
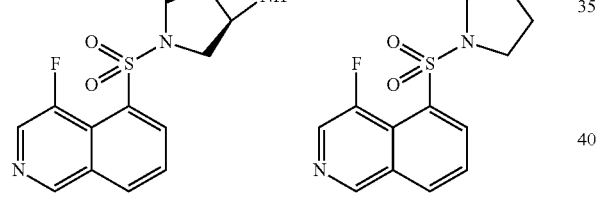
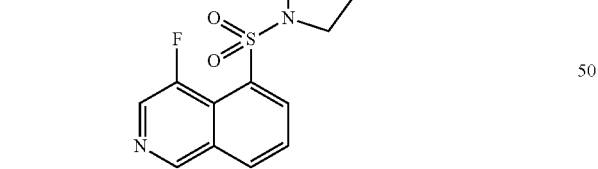
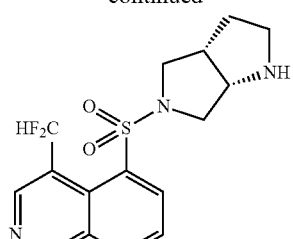
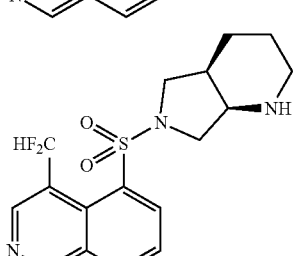
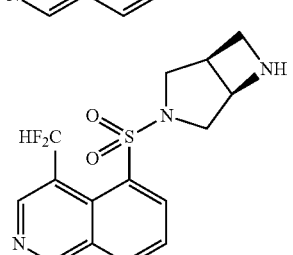
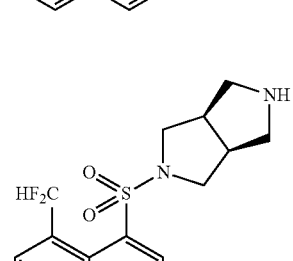
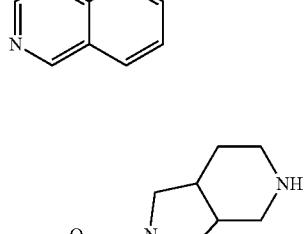
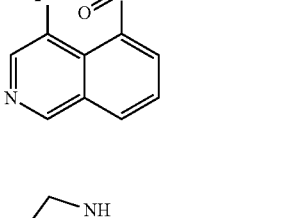

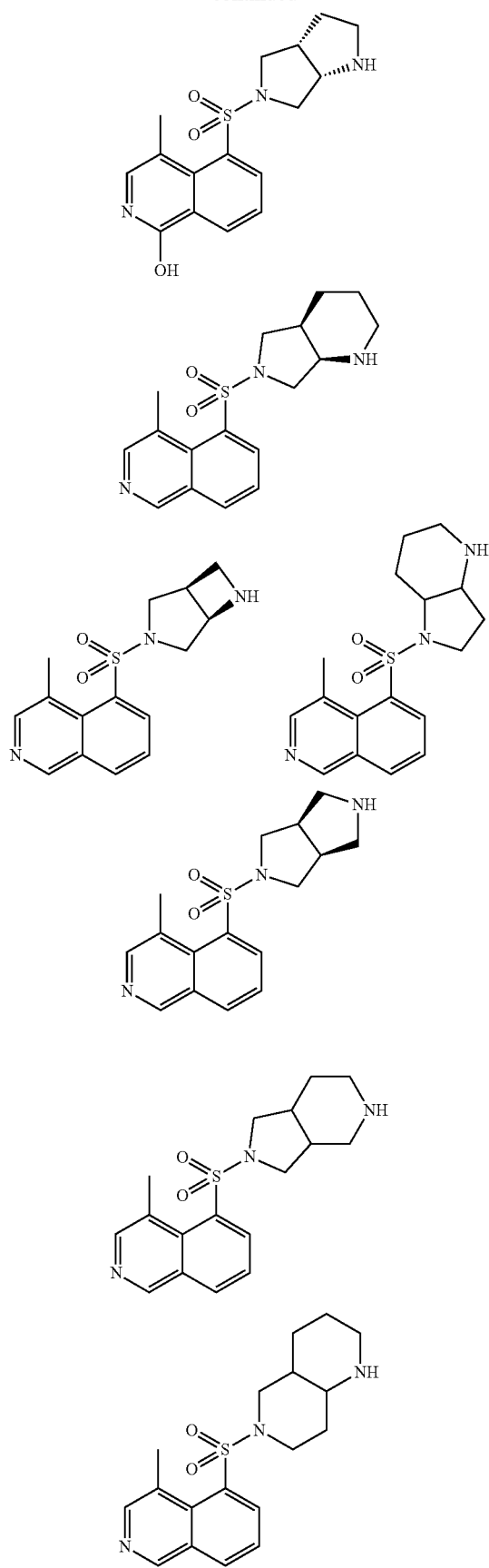
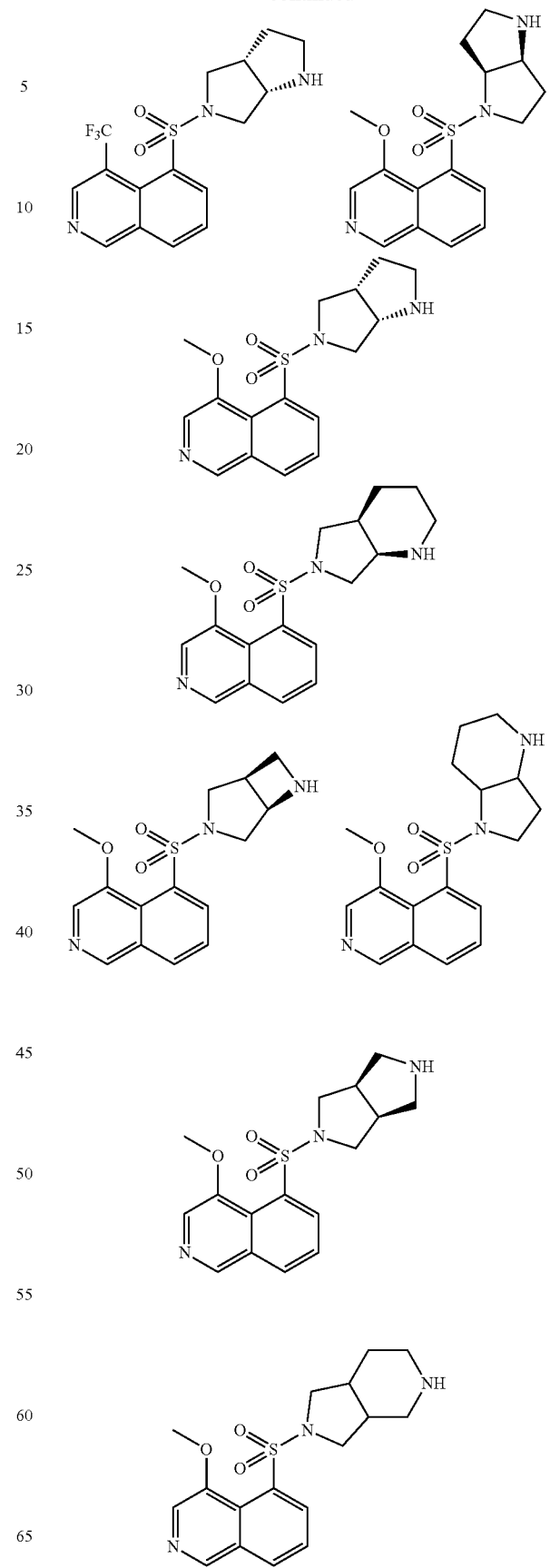

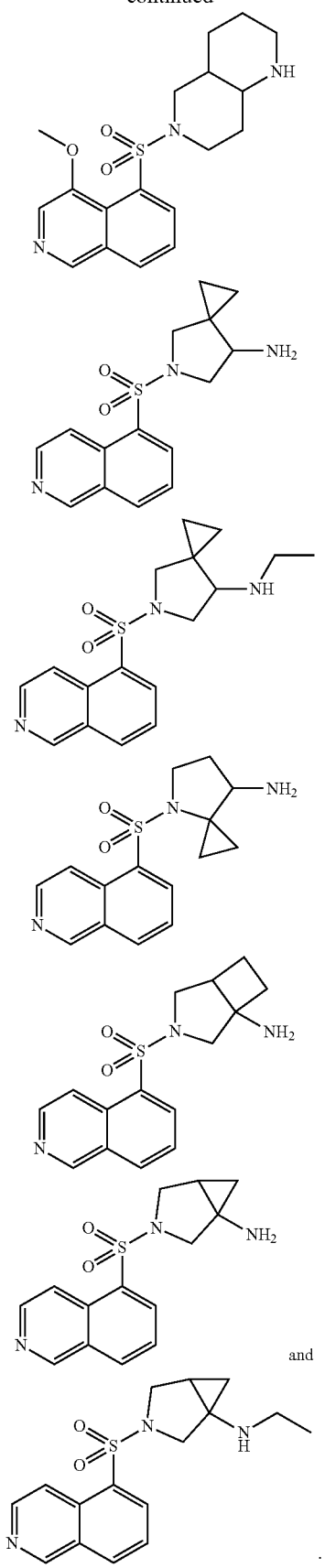

and

Another objective of the present invention is to provide a pharmaceutical composition comprising therapeutically effective amount of the aforesaid compound or a pharmaceutically acceptable salt thereof and pharmaceutical acceptable carriers.

Another objective of the present invention is to provide a use of the aforesaid compound or a pharmaceutically acceptable salt thereof, or the pharmaceutical composition in the preparation of a medicament for the prevention or treatment of various diseases caused by vasoconstriction, in which the diseases include cerebral embolism, cerebral ischemia, cerebral injury, vertebrobasilar insufficiency, cerebral angiospasm caused by subarachnoid hemorrhage, angina, glaucoma, hypertension, fibrosis.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salt" is meant to include a salt of a compound of the invention which is prepared by a relatively nontoxic acid or base the compound of the invention having particular substituents. When the compound of the invention contains a relatively acidic functional group, a base addition salt can be obtained by contacting a neutral form of such compounds with a sufficient amount of a desired base, either neat or in a suitable inert solvent. Examples of the pharmaceutically acceptable base addition salts include salts of sodium, potassium, calcium, ammonium, organic amine, or magnesium, or similar salts. When the compound of the invention contains a relatively basic functional group, an acid addition salt can be obtained by contacting a neutral form of such compounds with a sufficient amount of a desired acid, either neat or in a suitable inert solvent. Examples of the pharmaceutically acceptable acid addition salts include salts of inorganic acids including hydrochloric, hydrobromic, nitric, carbonic, hydrocarbonic, phosphoric, hydrophosphoric, dihydrophosphoric, sulfuric, hydrosulfuric, hydriodic, or phosphorous acids and the like; as well as salts of organic acids including acetic, propionic, isobutyric, maleic, malonic, benzoic, succinic, suberic, fumaric, lactic, mandelic, phthalic, benzenesulfonic, p-tolylsulfonic, citric, tartaric, methanesulfonic acid, or the like; and also salts of amino acids (such as arginate and the like), and salts of organic acids like glucuronic acid and the like (see, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral form of the compound is preferably regenerated by contacting the salt with a base or acid and then isolating the parent compounds in the conventional manner. The parent form of the compound differs from the various salt forms thereof in certain physical properties, such as solubility in polar solvents.

As used herein, "pharmaceutically acceptable salts" refers to derivatives of the compounds of the invention wherein the parent compound is modified by making a salt with an acid or base. Examples of pharmaceutically acceptable salts include, but are not limited to, mineral or organic acid salts of basic groups such as amines; alkali or organic salts of acidic groups such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, hydrobromic, hydrochloric, hydroiodide, hydroxyl acids hydroxynaphthoic, isethionic, lactic, lactobionic, lauryl sulfonic, maleic, malic, mandelic, methane sulfonic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile or the like are preferred.

In addition to salt forms, the present invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an in vivo environment.

Certain compounds of the invention can exist in unsolvated forms or solvated forms, including hydrated forms. In general, the solvated forms are equivalent to unsolvated forms and all are encompassed within the scope of the present invention.

Certain compounds of the invention may possess asymmetric carbon atoms (optical centers) or double bonds; the racemates, diastereomers, geometric isomers and individual isomers are all encompassed within the scope of the present invention.

The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, and all these mixtures as falling within the scope of the invention. Additional asymmetric carbon atoms can be present in a substituent such as an alkyl group. All such isomers, as well as mixtures thereof, are intended to be included in this invention.

Optically active (R)- and (S)-isomers and D and L isomers can be prepared by chiral synthons or chiral reagents, or other conventional techniques. If a particular enantiomer of a compound of the present invention is desired, it can be prepared by asymmetric synthesis, or by derivatization with a chiral auxiliary, where the resultant diastereomeric mixture is separated and the auxiliary group is cleaved to provide the pure desired enantiomers. Alternatively, where the molecule contains a basic functional group (such as an amino group) or an acidic functional group (such as a carboxyl group) diastereomeric salts can be formed with an appropriate optically active acid or base, followed by resolution of the diastereomers by general means known in the art, and subsequent recovery of the pure enantiomers. In addition, separation of enantiomers and diastereomers is frequently accomplished by chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, regardless of radioactivity or not, are intended to be encompassed within the scope of the present invention.

The term "pharmaceutically acceptable carrier or vehicle" refers to any formulation or carrier medium that is capable of delivery of an effective amount of an active agent of the invention without toxic side effects in a host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005) which is incorporated herein by reference.

The term "excipients" conventionally means carriers, diluents and/or vehicles needed in formulating defective pharmaceutical compositions.

The terms "effective amount" or "therapeutically effective amount" for a drug or pharmacologically active agent refers to a nontoxic but sufficient amount of the drug or agent to provide the desired effect. In the oral dosage forms of the present disclosure, an "effective amount" of an active agent of the composition refers to the amount of the active agent required to provide the desired effect when used in combination with the other active agent of the composition. The amount that is "effective" will vary from subject to subject, depending on the age and general condition of a recipient, and also a particular active agent, and an appropriate effective amount in an individual case may be determined by one of ordinary skill in the art using routine experimentation.

The terms "active ingredient," "therapeutic agent," "active substance," or "active agent" mean a chemical entity which can be effective in treating a targeted disorder, disease or condition.

The term "substituted", means that any one or more hydrogens on a designated atom is replaced with a substituent including deuterium and a variant of hydrogen, provided that the designated atom's valency is normal, and that the substituted compound is stable. When a substituent is keto (i.e., =O), it means that 2 hydrogen atoms are replaced. Keto substituents are not present on aromatic moieties. The term "optionally substituted" means that the designated atom can be substituted or unsubstituted, and unless otherwise stated, the species and number of the substituents may be arbitrary provided that they can be achieved in Chemistry.

When any variable (e.g., R) occurs more than once in the constituent or structure of a compound, its definition at each occurrence is independent. Thus, for example, if a group is substituted with 0-2 Rs, then said group may optionally be substituted with up to two R groups and R at each occurrence has independently options. Also, combinations of substituents and/or variables are permissible only if such combinations result in stable compounds.

When a variable is selected from single bond, it indicates that the two radical groups connected with the single bond are linked directly, for an example, when L represents single bond, A-L-Z is A-Z actually.

When a bond to a substituent is shown to cross a bond connecting two atoms in a ring, then such substituent may be bonded to any atom on the ring. When a substituent is listed without indicating via which atom such substituent is bonded to the compound of a general formula including unspecified ones, then such substituent may be bonded via any atom therein. Combinations of substituents and/or variables are permissible only if such combinations result in stable compounds.

Substituents of the alkyl and heteroalkyl radicals are generically referred to as "alkyl group substituents" and they can be one or more selected from, but not limited to the following groups: —R', —OR', =O, =NR', =N—OR', —NR'R", —SR', -halogen, —SiR'R"R", OC(O)R', —C(O)R', —CO₂R', —CONR'R", —OC(O)NR'R", —NR"C(O)R', NR'C(O)NR"R'", —NR"C(O)₂R', —NR""—C(NR'R"R''')=NR"", NR""C(NR'R")=NR"', —S(O)R', —S(O)₂R', S(O)₂NR'R", NR"SO₂R', —CN, —NO₂, —N₃, —CH(Ph)₂, and fluoro(C₁-C₄)alkyl, with a number of substitutents ranging from zero to (2m'+1), where m' is the total number of carbon atoms in such radical. R', R", R'", R"" and R""' are each preferably independently hydrogen, substituted or unsubstituted heteroalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion one of skill in the art will understand that the term "alkyl" is meant to include groups constituted by carbon atoms bonding to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents of the aryl and heteroaryl groups are generically referred to as "aryl group substituents." The substituents are selected from, for example: —R', —OR', —NR'R", —SR', -halogen, —SiR'R"R'", OC(O)R', —C(O)R', —CO2R', —CONR'R", —OC(O)NR'R", —NR"C(O)R', NR'C(O)NR"R'", —NR"C(O)₂R', —NR""—C(NR'R"R''')=NR"", NR""C(NR'R")=NR"', —S(O)R', —S(O)₂R', —S(O)₂NR'R", NR"SO₂R', —CN, —NO₂, —N₃, —CH(Ph)₂, fluoro(C1-C4)alkoxy, and fluoro(C1-C4)alkyl, etc, with a number ranging from zero to the total number of open valences on the aromatic ring; where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')q-U—, wherein T and U are independently selected from —NR—, —O—, —CRR'— or a single bond, and q is an integer from 0 to 3. Alternatively, two of the substituents on adjacent atoms of the aryl or heteroaryl ring may optionally be replaced with a substituent of the formula -A(CH2)rB—, wherein A and B are independently selected from —CRR'—, —O—, —NR—, —S—, —S(O)—, S(O)2-, —S(O)2NR'— or a single bond, and r is an integer from 1 to 4. One of the single bonds of the thus formed new ring may optionally be replaced with a double bond. Alternatively, two of the substituents on adjacent atoms of the aryl or heteroaryl ring may optionally be replaced with a substituent of the formula -A(CH2)rB—, where s and d are separately and independently selected from integers from 0 to 3, and X is —O—, —NR'—, —S(O)—, —S(O)2-, or —S(O)2NR'—. The substituents R, R', R" and R'" are separately, preferably and independently selected from hydrogen and substituted or unsubstituted (C1-C6)alkyl.

The term "halo" or "halogen," by themselves or as part of another substituent, means, unless otherwise stated, a fluorine, chlorine, bromine, or iodine atom. Additionally, the term "haloalkyl," are meant to include monohaloalkyl and polyhaloalkyl. For example, the term "halo(C1-C4)alkyl" is mean to include, but not be limited to, trifluoromethyl, 2,2,2-trifluoroethyl, 4-chlorobutyl, 3-bromopropyl, and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. C1-6 alkoxy is intended to include C1, C2, C3, C4, C5, and C6 alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. 3-7 cycloalkyl is intended to include C3, C4, C5, C6, and C7 cycloalkyl groups. "Alkenyl" is intended to include hydrocarbon chains of either straight or branched configuration and one or more unsaturated carbon-carbon bonds that may occur in any stable point along the chain, such as ethenyl and propenyl.

The term "Halo" or "halogen" refers to fluoro, chloro, bromo, and iodo.

As used herein, the term "hetero", mean, unless otherwise stated, "heteroatom" or "heteroradical" (namely radical containing heteroatom), including atoms other than carbon (C) and hydrogen (H), also including the radicals containing these aforesaid heteroatoms. Examples include oxygen (O), nitrogen (N) sulfur (S), silicon (Si), germanium (Ge), aluminum (Al) and boron (B), also include optionally substituted —C(=O)N(H)—, —N(H)—, —C(=NH)—, —S(=O)₂ N(H)—, or —S(=O)N(H)—.

"Ring or cyclo" means a substituted or unsubstituted cycloalkyl, heterocycloalkyl, cycloalkenyl, heterocycloalkenyl, cycloalkynyl, heterocycloalkynyl, aryl, or heteroaryl. The so-called ring includes mono, bi, spiro, fused, and bridged ring moieties. The number of atoms in a ring is typically defined as the number of members of the ring. For example, a "5- to 7-membered ring" means there are 5 to 7 atoms in the encircling arrangement. Unless otherwise specified, the ring optionally includes one to three heteroatoms. Thus, the term "5- to 7-membered ring" includes, for example phenyl, pyridinyl and piperidinyl. The term "5- to 7-membered heterocycloalkyl ring", on the other hand, include pyridinyl and piperidinyl, but not phenyl. The term "ring" further includes a ring system comprising at least one ring, wherein each "ring" is independently defined as above.

The term "heterocycle" or "heterocyclio" is intended to mean a stable monocyclic, bicyclic, or tricyclic ring containing heteroatom or heteroradical, which may be saturated, partially unsaturated or unsaturated (aromatic), and include carbon atoms and 1, 2, 3, or 4 ring heteroatoms independently selected from the group consisting of N, O and S in which any of the above-defined heterocyclic rings may be fused to a benzene ring to form a bicyclic group. The nitrogen and sulfur heteroatoms may optionally be oxidized (i.e., NO and S(O) p, p is 1 or 2). The nitrogen atom may be substituted or unsubstituted (i.e., N or NR wherein R is H or other substituents, already defined herein). The heterocyclic ring may be attached to its pendant group at any heteroatom or carbon atom that results in a stable structure. The heterocyclic rings described herein may be substituted on carbon or on a nitrogen atom if the resultant compound is stable. A nitrogen in the heterocycle may optionally be quaternized. In a preferred embodiment, when the total number of S and O atoms in the heterocycle exceeds 1, then these heteroatoms are not adjacent to one another. In another preferred embodiment the total number of S and O atoms in the heterocycle is not more than 1. As used herein, the term "aromatic heterocyclic group" or"heteroaryl" is intended to mean a stable 5-, 6-, or 7-membered monocyclic or bicyclic or 7-, 8-, 9-, or 10-membered bicyclic heterocyclic aromatic ring which includes carbon atoms and 1, 2, 3, or 4 heteroatoms independently selected from the group consisting of N, O and S. The nitrogen atom may be substituted or unsubstituted (i.e., N or NR wherein R is H or other substituents already defined herein). The nitrogen and sulfur heteroatoms may optionally be oxidized (i.e., NO and S(O) p, p is 1 or 2). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridged rings include, but are not limited to, one carbon atom, two carbon atoms, one nitrogen atom, two nitrogen atoms, and a carbon-nitrogen group. It is to be noted that a bridge always converts a monocyclic ring into a tricyclic ring. In a bridged ring, the substituents on the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing.

The term "hydrocarbyl" or its hyponyms (such as alkyl, alkenyl, alkynyl and aryl etc.) by itself or as part of another substituent, means, unless otherwise stated, a straight or branched chain, or cyclic hydrocarbon radical, or combination thereof, which may be fully saturated (such as alkyl), mono- or polyunsaturated (such as alkenyl, alkynyl and aryl etc.), may be mono- or polysubstituted, may be monovalent (e.g., methyl), divalent (e.g., methylene), or polyvalent (e.g., methyne), and can include di- or multivalent radicals, having the designated number of carbon atoms designated (i.e. $C_1$-$C_{12}$ meaning one to 12 carbons, $C_{1-12}$ is selected from the group consisting of $C_1$, $C_2$, $C_3$, $C_4$, $C_5$, $C_6$, $C_7$, $C_8$, $C_9$, $C_{10}$, $C_{11}$, and $C_{12}$; $C_{3-12}$ is selected from the group consisting of $C_3$, $C_4$, $C_5$, $C_6$, $C_7$, $C_8$, $C_9$, $C_{10}$, $C_{11}$, and $C_{12}$.). "Hydrocarbyl" include, but are not limited to, aliphatic hydrocarbyl and aromatic hydrocarbyl, and the aliphatic hydrocarbyl include linear and cyclic ones, specifically including but not limited to, alkyl, alkenyl, and alkynyl, and the aromatic hydrocarbyl include, but are not limited to, 6-12 membered aromatichydrocarbyl, for example, benzene, and naphthalene, etc. In some embodiments, the term "hydrocarbyl" means a straight or branched chain radical, or combinations thereof, which may be fully saturated, mono- or polyunsaturated and can include di- and multivalent radicals. Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, homologs and isomers of radicals such as n-pentyl, n-hexyl, n-heptyl, n-octyl, and the like. An unsaturated alkyl group is one having one or more double bonds or triple bonds. Examples of unsaturated hydrocarbyl groups include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heterohydrocarbyl" or its hyponymshyponyms (such as heteroalkyl, heteroalkenyl, heteroalkynyl and heteroaryl etc.) by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain hydrocarbyl radical, or combinations thereof, consisting of the stated number of carbon atoms and at least one heteroatom. In typical embodiment, the heteroatoms are selected from the group consisting of B, O, N and S, wherein the nitrogen and sulfur atoms may optionally be oxidized and the nitrogen heteroatom may optionally be quaternized. The heteroatom or heteroradical may be placed at any internal position of the heterohydrocarbyl group, including the position at which the hydrocarbyl group is attached to the remainder of the molecule, but the terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—OCH$_3$, and CH=CH—N($CH_3$)—$CH_3$. Up to two heteroatoms may be consecutive, such as, for example, —$CH_2$—NH—$OCH_3$.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

Unless otherwise stated, the terms "cyclohydrocarbyl", "heterocyclohydrocarbyl", or their hyponyms (such as aryl, heteroaryl, cycloalkyl, heterocycloalkyl, cycloalkenyl, heterocycloalkenyl, cycloalkynyl, and heterocycloalkynyl etc.) by themselves or in combination with other terms, represent, unless otherwise stated, cyclic versions of "hydrocarbyl" or "heterohydrocarbyl", respectively. Additionally, for heterohydrocarbyl or heterocyclohydrocarbyl(such as heteroalkyl and heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Non-limiting examples of heterocycle moieties include 1-(1,2,5,6-tetrahydropyridyl), 1-piperidinyl, 2-piperidinyl, 3-piperidinyl, 4-morpholinyl, 3-morpholinyl, tetrahydrofuranindol-2-yl, tetrahydrofuran-3-yl, tetrahydrothien-2-yl, tetrahydrothien-3-yl, 1 piperazinyl, and 2-piperazinyl.

The term "aryl" means, unless otherwise stated, a polyunsaturated, aromatic substituent that may be mono-, di- or poly-substituted, and can be monovalent, divalent, or polyvalent, or a single ring or multiple rings (such as 1 to 3 rings; at least one ring is aromatic), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents of any of the above described aryl and heteroaryl ring systems are selected from the acceptable substituents described below.

For brevity, the term "aryl" when used in combination with other terms (e.g., aryloxy, arylthio, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom, e.g., phenoxymethyl, 2-pyridyloxymethyl, 3-(1-naphthyloxy)propyl, and the like.

The term "leaving group" means a functional group or atom which can be displaced by another functional group or atom in a substitution reaction, (such as a nucleophilic substitution reaction). For example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "protecting group" includes but is not limited to "amino-protecting group", "hydroxy-protecting group" or "thiol-protecting group". The term "amino-protecting group" means a protecting group suitable for preventing side reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like. The term "hydroxy-protecting group" means a protecting group suitable for preventing side reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The compounds of the present invention can be prepared in a number of synthetic methods known to one skilled in the art, including the specific embodiments described below, the embodiments formed by combining them with other chemical synthetic methods known in the art, and equivalents well known to those skilled in the art. Preferred embodiments include, but are not limited to, examples of the invention.

The following abbreviations are used: aq represents aqueous; HATU represents 0-(7-azabenzotriazol-1-yl)-N,N,N,N'-tetramethyluronium hexafluorophosphate; EDC represents N-(3-dimethylaminopropyl)-N'-ethylcarbodiimide hydrochloride, m-CPBA represents 3-chloroperoxybenzoic acid; equivalent represents eq.; CDI represents carbonyl diimidaole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, a amine protecting group; BOC represents tert-butylcarbonyl, amine protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents sulfurous dichloride; $CS_2$ represents carbon disulfide; TsOH represents 4-methylbenzenesulfonic acid; NFSI represents N-fluoro-N-(phenylsulfonyl)benzenesulfonamide; NCS represents N-chlorosuccinimide; n-$Bu_4NF$ represents tetrabutylammonium fluoride; i-PrOH represents 2-propanol and mp represents melting point; mp represents melting point.

Compounds were named either manually or by using ChemDraw®, or using vendors catalogue name if commercially available.

Compared with the prior art, the compounds of the present invention have better effect, lower toxic than the compounds in the prior art, and make great progress in activity, $T_{1/2}$, solubility and DMPK and etc., which are more suitable to be pharmaceuticals.

DETAILED DESCRIPTION OF THE INVENTION

The following illustrative examples have been prepared, isolated and characterized using the methods disclosed herein. The following examples demonstrate a partial scope of the invention and are not meant to be limiting of the scope of the invention. While the invention has been described in detail and with reference to specific embodiments thereof, it will be apparent to one skilled in the art that various changes and modifications can be made therein without departing from the spirit and scope thereof.

Example 1

5-((hexahydropyrrolo[3,2-b]pyrrol-1(2H)-yl)sulfonyl)isoquinoline

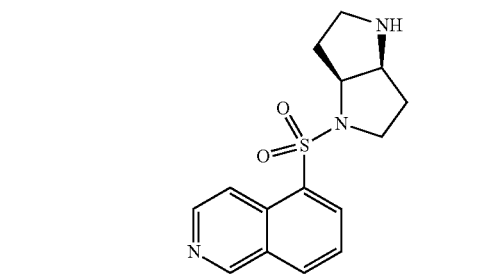 [SMILES: O=S(=O)(c1cccc2cnccc12)N1CC[C@@H]2NCC[C@@H]21]

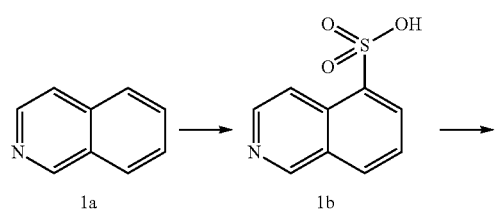

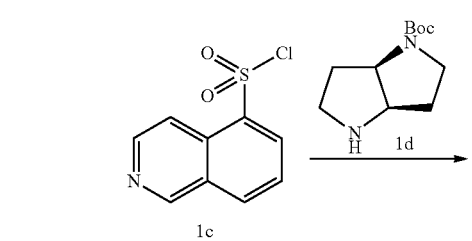

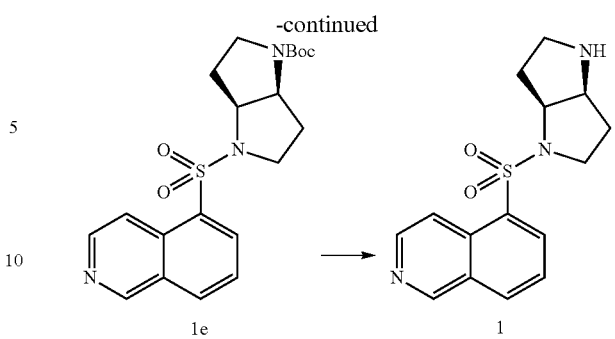

Step 1

Isoquinoline 1a (47.5 mL, 405 mmol) was slowly added to 22 mL concentrated sulfuric acid, and stirred into small pieces. Then the resulting mixture was added slowly in 20% fuming sulfuric acid (200 mL). The resulting clear solution was allowed to stand for 2 days at room temperature before being poured onto crushed ice (700 g). The mixture was stood overnight. The precipitate was collected by filtration, the cake was washed by water (100 mL×2) and dried in oven to give isoquinoline-5-sulfonic acid 1b (50 g, yield: 60%), used in next step directly.

$^1$H NMR (400 MHz, D$_2$O): δ 9.66 (s, 1H), 8.94-8.92 (m, 1H), 8.62-8.60 (m, 2H), 8.58-8.56 (m, 1H), 8.50-8.48 (m, 1H), 7.99-7.95 (m, 1H).

MS-ESI cal. [M+H]$^+$ 210, found 210.

Step 2

The solution of isoquinoline-5-sulfonic acid 1b (4.0 g, 0.019 mol) in 25 mL thionyl chloride and 0.1 mL dimethylformamide was heated to reflux for 2 h. The mixture was then distilled under reduced pressure to remove unreacted thionyl chloride. The crude was washed by dichloromethane (10 mL×2), and air dried to give isoquinoline-5-sulfonyl chloride 1e (3.9 g, yellow solid, yield: 100%).

MS-ESI cal. [M+H]$^+$ 227, found 227.

Step 3

Under N$_2$ atmosphere, isoquinoline-5-sulfonyl chloride 1e (150 mg, 0.33 mmol) was dissolved in 2 mL anhydrous dichloromethane, cis-tert-butyl hexahydropyrrolo[3,2-b]pyrrole-1(2H)-carboxylate 1d (80 mg, 0.38 mmol, commercially available) and N,N-diisopropylethylamine (0.25 mL, 1.14 mmol) were added successively at 0° C. The reaction mixture was stirred at room temperature for 16 h, it was then diluted with dichloromethane (10 mL) and water (10 mL), extracted with dichloromethane (10 mL×2). The combined organic layers were dried over anhydrous Na$_2$OS$_4$ and filtered. The filtrate was concentrated under reduced pressure, the residual was purified by silical gel column chromatography (0-100% EtOAc/PE) to give the product tert-butyl 4-(isoquinolin-5-ylsulfonyl)hexahydropyrrolo[3,2-b]pyrrole-1(2H)-carboxylate 1e (100 mg, colorless oil, yield: 65%).

MS-ESI cal. [M+H]$^+$ 404, found 404.

Step 4

To a solution of compound 1e (100 mg, 0.250 mmol) in 5 mL EtOAc was dropwised 10 mL saturated EtOAc with HCl (g) at 0° C., the resulting mixture was stirred at r.t. for 0.5 h. The precipitate was filtered, the filter cake was washed with EtOAc (10 mL×2) and dried to give the title compound 5-((hexahydropyrrolo[3,2-b]pyrrol-1(2H)-yl) sulfonyl)isoquinoline hydrochloride 1 (60 mg, white solid, yield: 79%).

$^1$H NMR (400 MHz, D$_2$O): δ9.82 (s, 1H), 9.10 (d, J=6.8 Hz, 1H), 8.84 (d, J=7.6 Hz, 1H), 8.77 (d, J=7.6 Hz, 1H), 8.68

(d, J=6.8 Hz, 1H), 8.15 (t, J=7.6 Hz, 1H), 4.55-4.40 (m, 1H), 4.35-4.25 (m, 1H), 3.62-3.55 (m, 1H), 3.50-3.45 (m, 1H), 3.39-3.30 (m, 2H), 2.35-2.00 (m, 4H).

MS-ESI cal. [M+H]$^+$ 304, found 304.

Example 2

5-((hexahydropyrrolo[3,4-b]pyrrol-5(1H)-yl)sulfonyl)isoquinoline

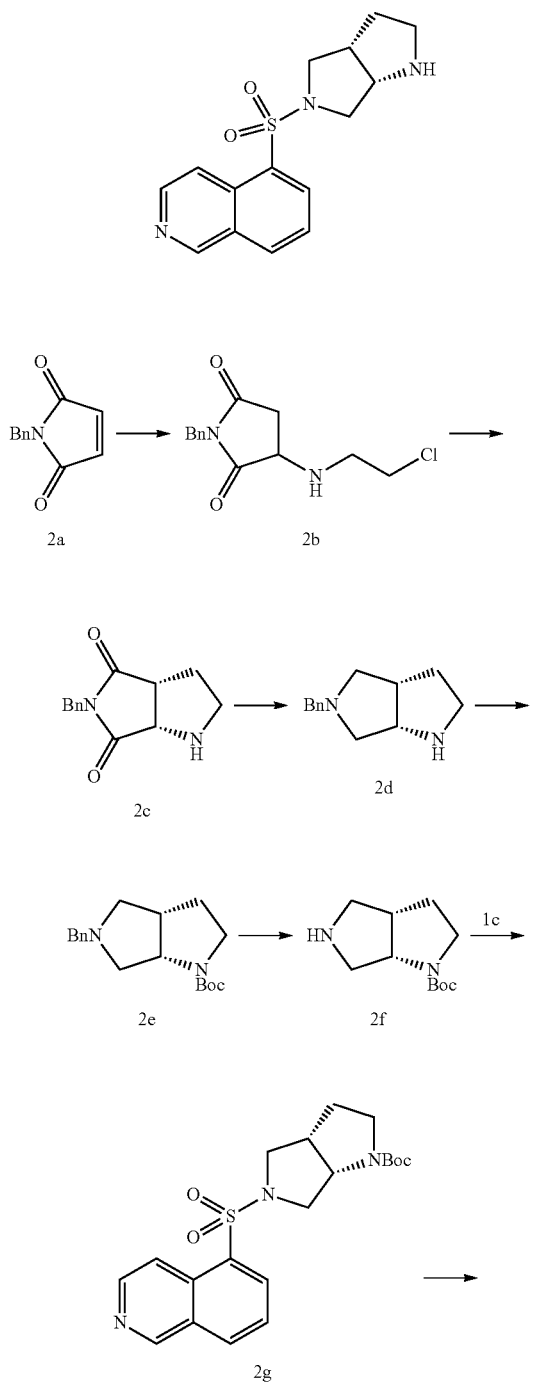

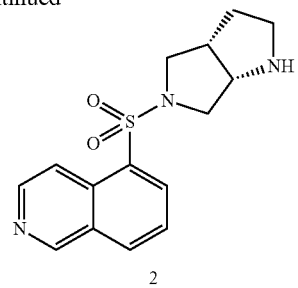

Step 1

A solution of 1-benzyl-1H-pyrrole-2,5-dione 2a (74.8 g, 0.400 mol), 2-chloroethylamine (58 g, 0.5 mol) and triethylamine (40 g, 0.40 mol) in 400 mL 1,4-dioxane was heated to reflux for 16 h. Then was cooled down to room temperature. The solvent was removed under reduced pressure, and the residue was purified by silica gel column chromatography (0-100% EtOAc/PE) to give 1-benzyl-3-((2-chloroethyl)amino)pyrrolidine-2,5-dione 2b (102 g, yield: 96%).

$^1$H NMR (400 MHz, CDCl$_3$): δ 7.40-7.25 (m, 5H), 4.66 (s, 2H), 3.82-3.77 (m, 1H), 3.67-3.63 (m, 2H), 3.01-2.94 (m, 3H), 2.55-2.50 (m, 1H), 2.21-2.15 (m, 1H).

Step 2

Under N$_2$ atmosphere, NaH (7.74 g, 358 mmol) was dissolved in 700 mL anhydrous DMF at 0° C. A solution of 1-benzyl-3-((2-chloroethyl)amino)pyrrolidine-2,5-dione 2b (40 g, 140 mmol) in 50 mL DMF was added at 30° C. After being stirred for 1 h at r.t., the reaction mixture was poured into 1 L water. The aqueous mixture was extracted with EtOAc (500 mL×3), the combined organic layers were dried over anhydrous Na$_2$SO$_4$ and filtered. The filtrate was concentrated under reduced pressure. The residual was purified by silica gel column chromatography (0-100% MeOH/EtOAc) to give 5-benzyltetrahydropyrrolo[3,4-b]pyrrole-4,6(2H,5H)-dione 2c (20 g, colorless oil, yield: 59%).

$^1$H NMR (400 MHz, CDCl$_3$): δ 7.37-7.28 (m, 5H), 4.65 (s, 2H), 4.13-4.11 (m, 1H), 3.30-3.27 (m, 1H), 3.07-3.05 (m, 1H), 2.57-2.56 (m, 1H), 2.15-2.05 (m, 3H).

Step 3

Under N$_2$ atmosphere, LiAlH$_4$ (7.19 g, 0.18 mol) was added to 250 mL THF portionwise at 0° C., then was added dropwisely a solution of cis-5-benzyltetrahydropyrrolo[3,4-b]pyrrole-4,6 (2H,5H)-dione 2c (20 g, 0.086 mol) in 250 mL THF at 0° C. After the completion of addition, the mixture was gradually warmed to reflux for 3 h. The mixture was cooled to 0° C., then was added dropwisely 7.2 mL water, 7.2 mL 15% aq. NaOH and 21.6 mL water in sequence. After additional stirred for 0.5 h, the mixture was filtered and the filtrate was concentrated to give 5-benzyloctahydropyrrolo[3,4-b]pyrrole 2d (16 g, colorless oil, yield: 92%).

MS-ESI cal. [M]$^+$ 203, found 203.

Step 4

To a solution of 5-benzyloctahydropyrrolo[3,4-b]pyrrole 2d (15 g, 74 mmol) in 300 mL dichloromethane was added N-ethyl-N-isopropylpropan-2-amine (19 g, 148 mmol) and di-tert-butyl dicarbonate (17.8 g, 0.081 mol), the resulting mixture was stirred for 4 h at room temperature. The mixture was concentrated, and the residual was purified by silica gel column chromatography (0-100% EtOAc/PE) to give tert-butyl 5-benzylhexahydropyrrolo[3,4-b]pyrrole-1(2H)-carboxylate 2e (18 g, yield: 81%).

MS-ESI cal. [M+H]$^+$ 310, found 310.

Step 5

To a solution of tert-butyl 5-benzylhexahydropyrrolo[3,4-b]pyrrole-1(2H) carboxylate 2e (12 g, 39.7 mmol) in THF (1 L) was added dry Pd(OH)$_2$/C (1.8 g, 10%) under argon atmosphere. The mixture was stirred under H$_2$ (3 MPa) atmosphere at 70° C. for 16 h. The reaction mixture was cooled to room temperature, and filtered through a pad of diatomite to remove the solid catalyst, the filtrate was concentrated to give cis-tert-butyl hexahydropyrrolo[3,4-b]pyrrole-1(2H)-carboxylate 2f (8 g, light yellow oil, yield: 95%).

$^1$H NMR (400 MHz, CD$_3$OD): δ 4.21-4.17 (m, 1H), 3.51-3.36 (m, 2H), 3.05-2.90 (m, 3H), 2.89-2.77 (m, 2H), 2.06-2.02 (m, 1H), 1.77-1.71 (m, 1H), 1.48 (s, 9H).

Step 6

From cis-tert-butyl hexahydropyrrolo[3,4-b]pyrrole-1(2H)-carboxylate 2f (212 mg, 1.00 mmol) and isoquinoline-5-sulfonyl chloride 1c (250 mg, 1.10 mmol), the compound 5-(isoquinolin-5-ylsulfonyl)hexahydro pyrrolo[3,4-b]pyrrole-1(2H)-carboxylate 2g was made following the procedure described for the synthesis of 1e (Example 1) and used in next step directly.

Step 7

The tile compound 5-((hexahydropyrrolo[3,4-b]pyrrol-5(1H)-yl)sulfonyl)isoquinoline2 was made from 5-(isoquinolin-5-ylsulfonyl)hexahydro pyrrolo[3,4-b]pyrrole-1(2H)-carboxylate 2g (50.0 mg, 0.130 mmol) following the procedure described for the synthesis of 1 (Example 1).

(19 mg, white solid, yield: 50%).

$^1$H NMR (400 MHz, CD$_3$OD): δ 9.39 (s, 1H), 8.68-8.61 (m, 2H), 8.48-8.38 (m, 2H), 7.88-7.84 (m, 1H), 3.83-3.74 (m, 1H), 3.25-3.12 (m, 4H), 2.82-2.77 (m, 3H), 1.91-1.86 (m, 1H), 1.60-1.56 (m, 1H).

MS-ESI calc'd. [M+H]$^+$ 304, found 304.

Example 3

5-((hexahydro-1H-pyrrolo[3,4-b]pyridin-6(2H)-yl)sulfonyl)isoquinoline

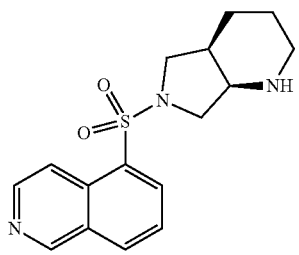 [SMILES: O=S(=O)(c1cccc2cnccc12)N1C[C@H]2CCCN[C@H]2C1]

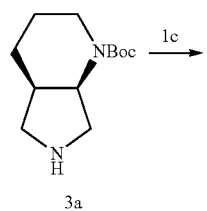

3a

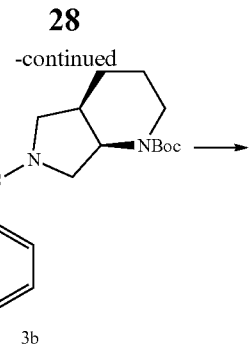

3b

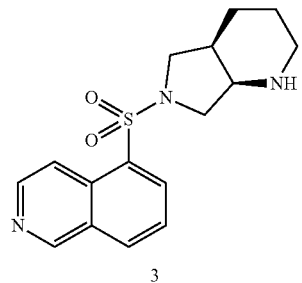

3

Step 1

From cis-tert-butyl octahydro-1H-pyrrolo[3,4-b]pyridine-1-carboxylate 3a (100 mg, 0.44 mmol, commercially available) and isoquinoline-5-sulfonyl chloride 1c (114 mg, 0.500 mmol), the compound tert-butyl 6-(isoquinolin-5-ylsulfonyl)octahydro-1H-pyrrolo[3,4-b]pyridine-1-carboxylate 3b was made following the procedure described for the synthesis of 1e (Example 1) and used in next step directly.

Step 2

The title compound 5-((hexahydro-1H-pyrrolo[3,4-b]pyridin-6(2H)-yl)sulfonyl) isoquinoline 3 was made from tert-butyl 6-(isoquinolin-5-ylsulfonyl)octahydro-1H-pyrrolo[3,4-b]pyridine-1-carboxylate 3b (80.0 mg, 0.190 mmol) following the procedure described for the synthesis of 1 (Example 1). (40 mg, white solid, yield: 65%)

$^1$H NMR (400 MHz, CD$_3$OD): δ 9.35 (s, 1H), 8.67-8.57 (m, 2H), 8.47 (d, J=7.2 Hz, 1H), 8.37 (d, J=8.0 Hz, 1H), 7.81 (t, J=8.0 Hz, 1H), 3.47-3.38 (m, 3H), 3.34-3.26 (m, 2H), 2.78-2.71 (m, 1H), 2.55-2.46 (m, 1H), 2.17-2.07 (m, 1H), 1.65-1.30 (m, 4H).

MS-ESI calc'd. [M+H]$^+$ 318, found 318.

Example 4

(3,6-diazabicyclo[3.2.0]heptan-3-ylsulfonyl)isoquinoline

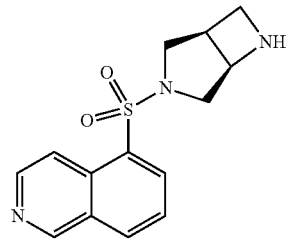 [SMILES: O=S(=O)(c1cccc2cnccc12)N1C[C@H]2CN[C@H]2C1]

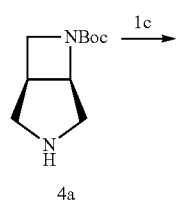

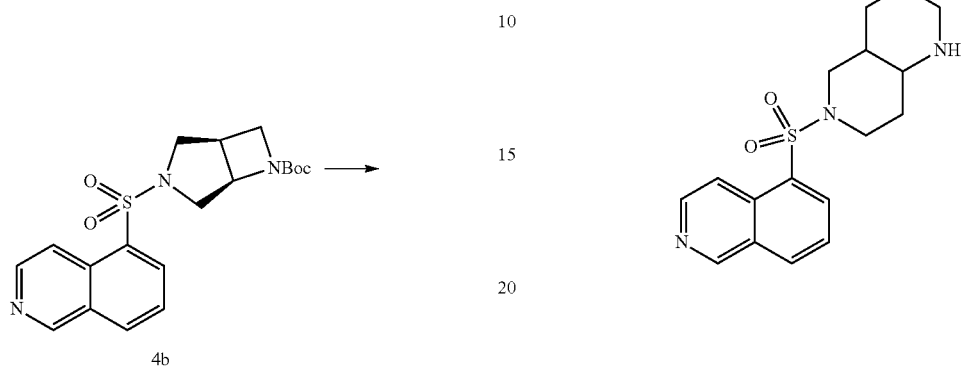

Step 1

From tert-butyl 3-(isoquinolin-5-ylsulfonyl-3,6-diazabicyclo[3.2.0]heptane-6-carboxylate 4a (66 mg, 0.33 mmol, commercially available) and isoquinoline-5-sulfonyl chloride 1c (107 mg, 0.400 mmol), the compound tert-butyl 3-(isoquinolin-5-ylsulfonyl)-3,6-diazabicycle[3.2.0]heptanes-6-carboxylate 4b was made following the procedure described for the synthesis of 1e (Example 1) a. (110 mg, yellow oil, yield: 85%).

MS-ESI calc'd. [M+H]$^+$ 390, found 390.

Step 2

The title compound 5-(3,6-diazabicyclo[3.2.0]heptan-3-ylsulfonyl)isoquinoline 4 was made from tert-butyl 3-(isoquinolin-5-ylsulfonyl)-3,6-diazabicycle[3.2.0]heptanes-6-carboxylate 4b (30 mg, 0.77 mmol) following the procedure described for the synthesis of 1 (Example 1). (15 mg, yellow solid, yield: 67%).

$^1$H NMR (400 MHz, D$_2$O): δ 9.74 (s, 1H), 9.17 (d, J=7.2 Hz, 1H), 8.78 (d, J=7.2 Hz, 1H), 8.7 (d, J=8.4 Hz, 1H), 8.6 (d, J=8.4 Hz, 1H), 8.09 (t, J=7.2 Hz, 1H), 4.15-4.05 (m, 1H), 4.05-3.95 (m, 1H), 3.75-3.69 (m, 3H), 3.29-3.24 (m, 1H), 2.96-2.93 (m, 1H), 2.80-2.78 (m, 1H).

MS-ESI calc'd. [M+H]$^+$ 290, found 290.

Example 5

6-(isoquinolin-5-ylsulfonyl)decahydro-1,6-naphthyridine

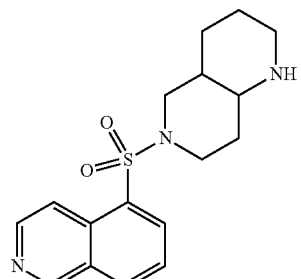

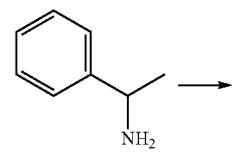

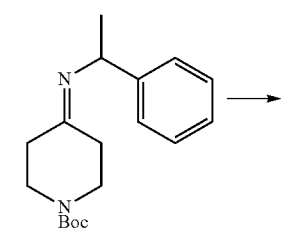

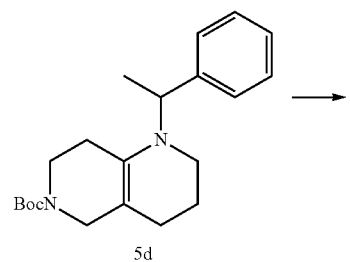

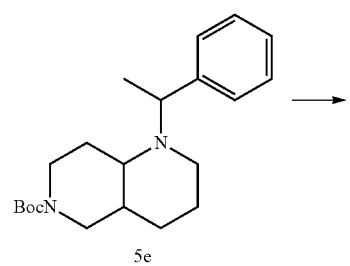

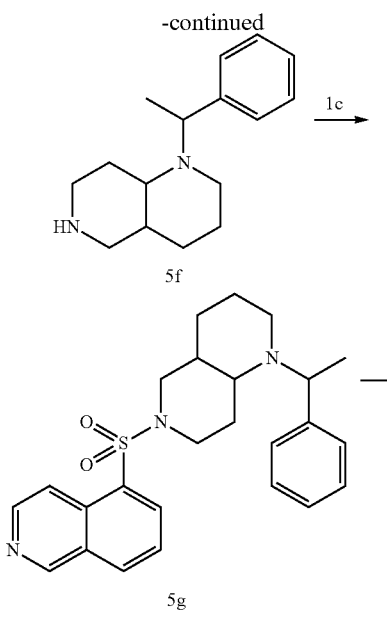

Step 1

To a solution of tert-butyl 4-oxopiperidine-1-carboxylate 5a (10 g, 0.050 mol) in 250 mL toluene was added 1-phenylethanamine 5b (6.05 g, 50.0 mmol). The resulting mixture was heated to reflux at 110° C. with a Dean-Stark trap for 3 h, then was cooled to room temperature and concentrated under reduced pressure to give tert-butyl 4-((1-phenylethyl)imino)piperidine-1-carboxylate 5c (15.1 g, yellow oil, yield: 100%). The crude was used directly without further purification.

Step 2

Under $N_2$ atmosphere, n-butyl lithium (34.4 mL, 0.086 mol, 2 M) was added dropwisely to a solution of diisopropylamine (7.4 g, 0.075 mol) in 100 mL anhydrous THF at −10° C. The resulting mixture was further stirred at this temperature for 20 min, then was cooled to −30° C. and added a solution of tert-butyl 4-((1-phenylethyl)imino)piperidine-1-carboxylate 5c (15.1 g, 0.05 mol) in 100 mL anhydrous THF. After additional stirred for 30 min at −30° C., the mixture was cooled to −65° C., and added 1-bromo-3-chloropropane (9.45 g, 60.0 mmol, in 50 mL THF) dropwisely. After the completion of addition, the reaction mixture was warmed to room temperature slowly, stirred for 2 h at room temperature then refluxed for 4 h. The mixture was cooled to room temperature and concentrated under reduced pressure. The residue was diluted with water (100 mL) and extracted with methyl tert-butyl ether (200 mL×3). The combined organic layers were washed with brine (100 mL), dried over anhydrous $Na_2SO_4$, and filtered. The filtrate was concentrated under reduced pressure to give tert-butyl 1-(1-phenylethyl)-1,2,3,4,7,8-hexahydro-1,6-naphthyridine-6(5H)-carboxylate 5d (17 g, yellow oil) which was used in the next step directly without further purification.

MS-ESI calc'd. $[M+H]^+$ 343, found 343.

Step 3

To a solution of tert-butyl 1-(1-phenylethyl)-1,2,3,4,7,8-hexahydro-1,6-naphthyridine-6(5H)-carboxylate 5d (7 g, 0.02 mol) in 600 mL THF was added 10% Pd/C (700 mg, 10%). The resulting mixture was stirred under $H_2$ (3 MPa) atmosphere at 40° C. for 14 h, then was filtered through a pad of diatomite to remove Pd/C. The filtrate was concentrated under reduced pressure to give crude product which was purified by silica gel column chromatography (0-100% EtOAc/PE) to give tert-butyl 1-(1-phenylethyl) octahydro-1,6-naphthyridine-6(2H)-carboxylate 5e (2.26 g, yellow oil, yield: 33%).

MS-ESI calc'd. $[M+H]^+$ 345, found 345.

Step 4

To a solution of tert-butyl 1-(1-phenylethyl) octahydro-1,6-naphthyridine-6(2H)-carboxylate 5e (500 mg, 1.45 mmol) in 5 mL EtOAc was added 30 mL EtOAc saturated with HCl (g). The mixture was stirred for 1.5 h at room temperature, then was concentrated under reduced pressure to give 1-(1-phenylethyl)decahydro-1,6-naphthyridine 5f (296 mg, white solid, yield: 84%).

MS-ESI calc'd. $[M+H]^+$ 245, found 245.

Step 5

From 1-(1-phenylethyl)decahydro-1,6-naphthyridine 5f (296 mg, 1.21 mmol) and isoquinoline-5-sulfonyl chloride 1c (550 mg, 2.42 mmol), the compound 6-(isoquinolin-5-ylsulfonyl)-1-(1-phenylethyl)decahydro-1,6-naphthyridine 5g was made following the procedure described for the synthesis of 1e (Example 1). (96 mg, yellow solid, yield: 18%).

MS-ESI calc'd. $[M+H]^+$ 436, found 436.

Step 6

A solution of 6-(isoquinolin-5-ylsulfonyl)-1-(1-phenylethyl)decahydro-1,6-naphthyridine 5g (30 mg, 0.069 mmol) in 1 mL TFA was heated by microwave at 100° C. for 1 h. The mixture concentrated under reduced pressure to give a residual which was purified by prep. HPLC to give 6-(isoquinolin-5-ylsulfonyl)decahydro-1,6-naphthyridine 5 (7 mg, white solid, yield: 31%).

$^1$H NMR (400 MHz, $CD_3OD$): δ 9.41 (s, 1H), 8.66-8.62 (m, 1H), 8.59-8.54 (m, 1H), 8.50-8.43 (m, 2H), 7.87 (t, J=8.0 Hz, 1H), 4.06-3.50 (m, 4H), 3.14-3.00 (m, 3H), 2.24-2.10 (m, 1H), 1.99-1.63 (m, 6H).

MS-ESI calc'd. $[M+H]^+$ 332, found 332.

Example 6

5-((octahydro-1H-pyrrolo[3,2-b]pyridin-1-yl)sulfonyl)isoquinoline

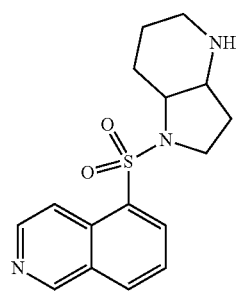 [SMILES: O=S(=O)(c1cccc2cnccc12)N1CCC2NCCCC21]

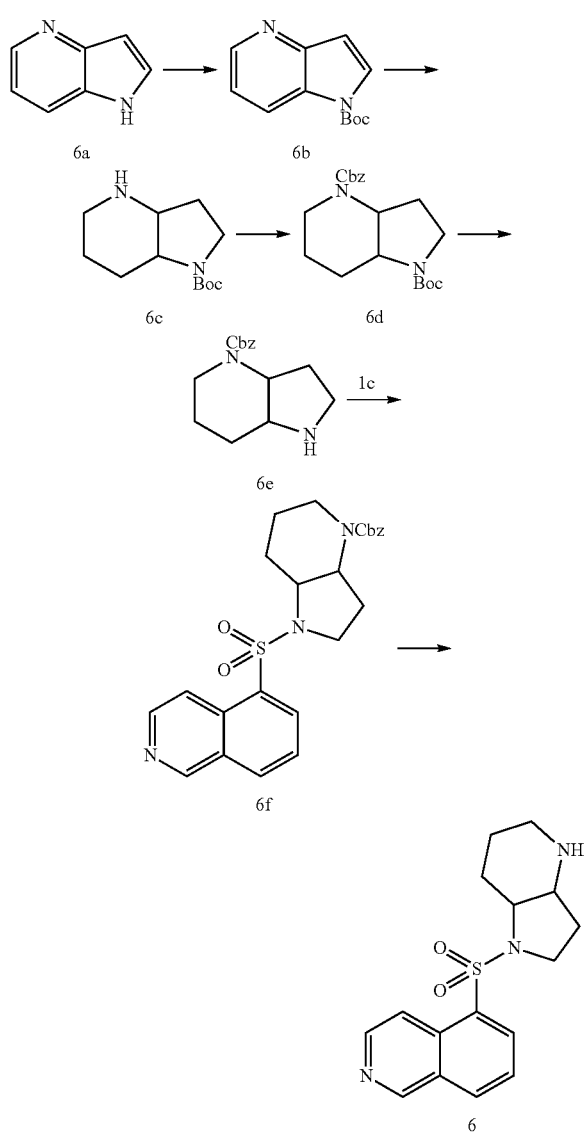

Step 1

To a solution of 1H-pyrrolo[3,2-b]pyridine 6a (2.00 g, 16.9 mmol) in 30 mL dichloromethane was added 4-dimethylaminopyridine (2.06 g, 16.9 mmol), triethylamine (2.05 g, 20.3 mmol) and di-tert-butyl dicarbonate (4.42 g, 20.3 mmol). The resulting mixture was stirred overnight at room temperature. The mixture was concentrated under reduced pressure and purified by silica gel column chromatography (20% EtOAc/PE) to give tert-butyl 1H-pyrrolo[3,2-b]pyridine-1-carboxylate 6b (3.5 g, white solid, yield: 95%).

MS-ESI calc'd. [M+H]$^+$ 219, found 219.

Step 2

To a solution of tert-butyl 1H-pyrrolo[3,2-b]pyridine-1-carboxylate 6b (1.00 g, 4.59 mmol) in 30 mL acetic acid was added PtO$_2$ (104 mg, 0.460 mmol), the resulting mixture was stirred under H$_2$ (4 MPa) atmosphere at 50° C. for 24 h. The reaction mixture was cooled to room temperature, filtered, and concentrated under reduced pressure to give crude tert-butyl octahydro-1H-pyrrolo[3,2-b]pyridine-1-carboxylate 6c (1.0 g, colorless oil, 96%) which was used in the next step without further purification.

MS-ESI calc'd. [M+H]$^+$ 227, found 227.

Step 3

To a solution of tert-butyl octahydro-1H-pyrrolo[3,2-b]pyridine-1-carboxylate 6c (1.00 g, 4.42 mmol) in 30 mL dichloromethane was added N,N-diisopropylethylamine (2.4 mL, 13.3 mmol) and Carboxylic acid chloride benzyl ester (1.13 g, 6.63 mmol) at 0° C. under N$_2$ atmosphere. The resulting mixture was stirred at room temperature overnight, then was concentrated under reduced pressure. The residue was added 20 mL water, the aqueous mixture was extracted with EtOAc (30 mL×3). The combined organic layers were washed with brine (30 mL), dried over anhydrous Na$_2$SO$_4$, filtered, and concentrated to give crude product which was purified by silica gel column chromatography (10% EtOAc/PE) to give 4-benzyl 1-tert-butyl hexahydro-1H-pyrrolo[3,2-b]pyridine-1,4(2H)-dicarboxylate 6d (1.35 g, yellow oil, yield: 85%).

MS-ESI calc'd. [M+H]$^+$ 361, found 361.

Step 4

To a solution of 4-benzyl 1-tert-butyl hexahydro-1H-pyrrolo[3,2-b]pyridine-1,4(2H)-dicarboxylate 6d (1.35 g, 3.75 mmol) in 5 mL EtOAc was added 40 mL EtOAc saturated with HCl (g). The resulting mixture was stirred for 45 min at room temperature, and concentrated under reduced pressure to give benzyl hexahydro-1H-pyrrolo[3,2-b]pyridine-4(2H)-carboxylate 6e (1.0 g, white solid, yield: 90%).

MS-ESI calc'd. [M+H]$^+$ 261, found 261.

Step 5

From benzyl hexahydro-1H-pyrrolo[3,2-b]pyridine-4(2H)-carboxylate 6e (132 mg, 0.51 mmol) and isoquinoline-5-sulfonyl chloride 1c (141, 0.62 mmol), the compound benzyl 1-(isoquinolin-5-ylsulfonyl) hexahydro-1H-pyrrolo[3,2-b]pyridine-4(2H)-carboxylate 6f was made following the procedure described for the synthesis of compound 1e (Example 1). (185 mg, yellow oil, yield: 81%).

MS-ESI calc'd. [M+H]$^+$ 452, found 452.

Step 6

The compound 5-((octahydro-1H-pyrrolo[3,2-b]pyridin-1-yl)sulfonyl) isoquinoline 6 was made from benzyl 1-(isoquinolin-5-ylsulfonyl) hexahydro-1H-pyrrolo[3,2-b]pyridine-4(2H)-carboxylate 6f (150 mg, 0.332 mmol) following the procedure described for the synthesis of compound 5 (Example 1) (64 mg, white solid, yield: 61%).

$^1$H NMR (400 MHz, CD$_3$OD): δ 9.42 (s, 1H), 8.69-8.64 (m, 2H), 8.50-8.40 (m, 2H), 7.88 (t, J=8.0 Hz, 1H), 3.83-3.79 (m, 1H), 3.72-3.54 (m, 3H), 3.16-3.10 (m, 1H), 2.99-2.93 (m, 1H), 2.27-2.23 (m, 1H), 2.10-2.01 (m, 2H), 1.92-1.84 (m, 1H), 1.77-1.69 (m, 1H), 1.64-1.59 (m, 1H).

MS-ESI calc'd. [M+H]$^+$ 318, found 318.

Example 7

5-((hexahydropyrrolo[3,4-c]pyrrol-2(1H)-yl)sulfonyl)isoquinoline

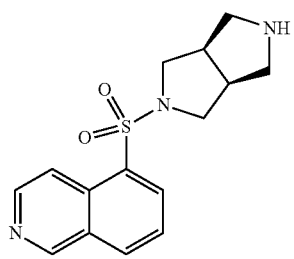 [SMILES: O=S(=O)(c1cccc2cnccc12)N1C[C@H]2CNC[C@H]2C1]

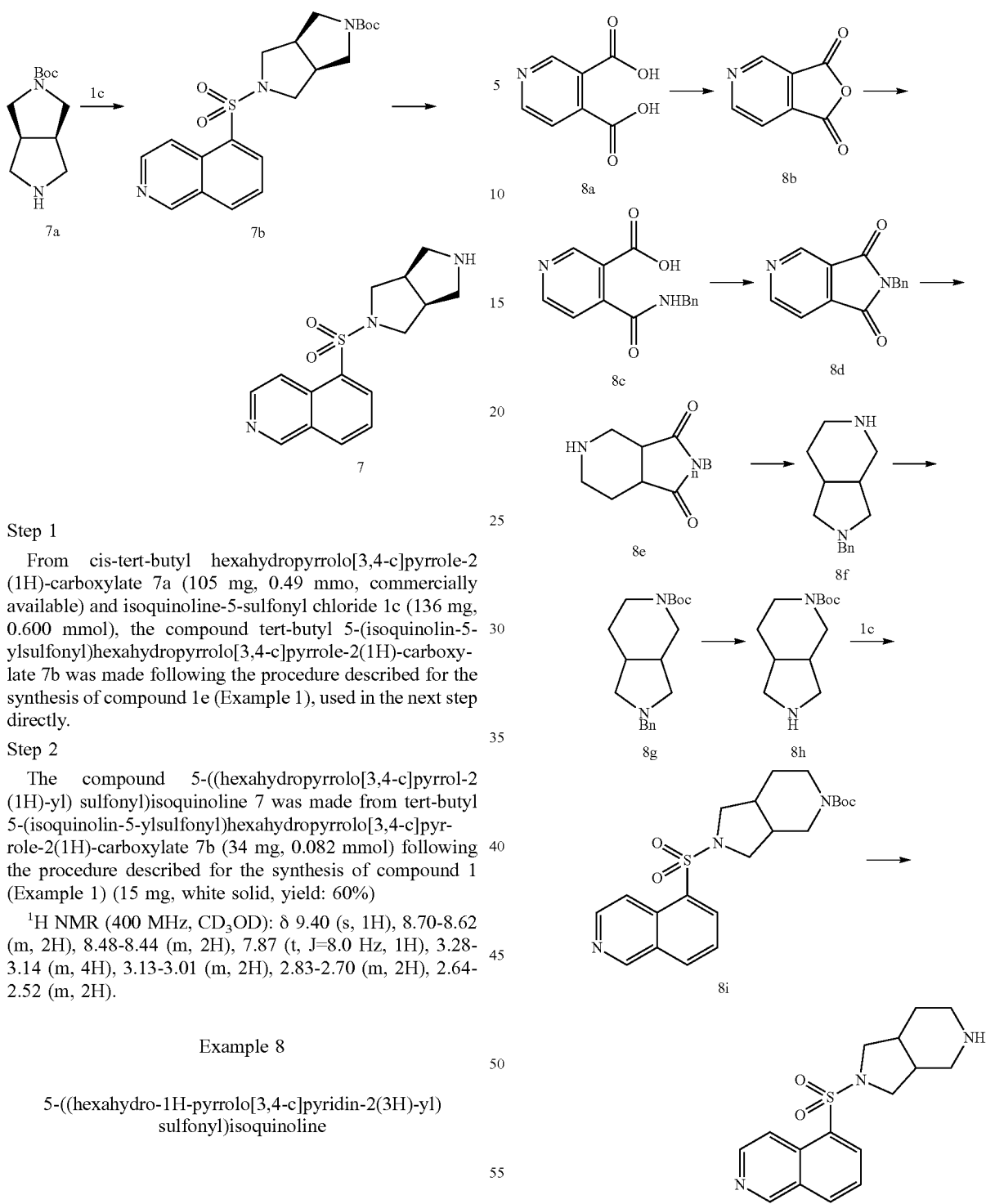

Step 1

From cis-tert-butyl hexahydropyrrolo[3,4-c]pyrrole-2(1H)-carboxylate 7a (105 mg, 0.49 mmo, commercially available) and isoquinoline-5-sulfonyl chloride 1c (136 mg, 0.600 mmol), the compound tert-butyl 5-(isoquinolin-5-ylsulfonyl)hexahydropyrrolo[3,4-c]pyrrole-2(1H)-carboxylate 7b was made following the procedure described for the synthesis of compound 1e (Example 1), used in the next step directly.

Step 2

The compound 5-((hexahydropyrrolo[3,4-c]pyrrol-2(1H)-yl) sulfonyl)isoquinoline 7 was made from tert-butyl 5-(isoquinolin-5-ylsulfonyl)hexahydropyrrolo[3,4-c]pyrrole-2(1H)-carboxylate 7b (34 mg, 0.082 mmol) following the procedure described for the synthesis of compound 1 (Example 1) (15 mg, white solid, yield: 60%)

$^1$H NMR (400 MHz, CD$_3$OD): δ 9.40 (s, 1H), 8.70-8.62 (m, 2H), 8.48-8.44 (m, 2H), 7.87 (t, J=8.0 Hz, 1H), 3.28-3.14 (m, 4H), 3.13-3.01 (m, 2H), 2.83-2.70 (m, 2H), 2.64-2.52 (m, 2H).

Example 8

5-((hexahydro-1H-pyrrolo[3,4-c]pyridin-2(3H)-yl)sulfonyl)isoquinoline

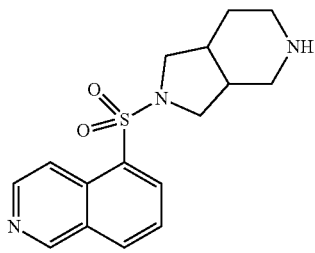 [SMILES: O=S(=O)(c1cccc2cnccc12)N1CC2CCNCC2C1]

Step 1

A solution of pyridine-3,4-dicarboxylic acid 8a (30.0 g, 180 mmol) in 250 mL acetic anhydride was heated to reflux for 3-4 h until it turned clear. The mixture was cooled to room temperature, and the solvent acetic anhydride was removed under reduced pressure to give furo[3,4-c]pyridine-1,3-dione 8b which was used in the next step directly.

Step 2

Benzyl amine (28.9 g, 270 mmol) was added to solid furo[3,4-c]pyridine-1,3-dione 8b (crude product of the last step) at 0° C., the resulting mixture was warmed to room temperature and allowed to stand for 1 h. The viscous liquid generated, 4-(benzylcarbamoyl)nicotinic acid 8c which was used in next step directly.

Step 3

4-(benzylcarbamoyl)nicotinic acid 8c (crude from last step) was dissolved in 150 mL acetic anhydride carefully the resulting mixture was heated at 110° C. for 4 h until it turned clear. The mixture was cooled to room temperature, and solvent acetic anhydride was removed by distillation under reduced pressure. The residue was diluted with 100 mL water and EtOAc (100 mL) and extracted with EtOAc (100 mL×2). The combined organic layers were washed with 100 mL saturated aq. $NaHCO_3$, 100 mL water and 100 mL brine successively, dried over anhydrous $Na_2SO_4$, filtered, and concentrated. The crude product was purified by silica gel column chromatography (30%-50% EtOAc/PE) to give white solid 2-benzyl-1H-pyrrolo[3,4-c]pyridine-1,3(2H)-dione 8d (29.5 g, yield: 69% for 3 step)

$^1$H NMR (400 MHz, $CDCl_3$): δ 9.17 (s, 1H), 9.07 (d, J=4 Hz, 1H), 7.76 (d, J=4 Hz, 1H), 7.50-7.40 (m, 2H), 7.30-7.36 (m, 3H), 4.88 (s, 2H).

Step 4

To a solution of 2-benzyl-1H-pyrrolo[3,4-c]pyridine-1,3 (2H)-dione 8d (9.60 g, 40.3 mmol) in 300 mL MeOH was added wet Pd/C (2.0 g, 20%), the resulting mixture was placed under 3 MPa $H_2$ atmosphere and stirred at 60° C. overnight. The mixture was cooled to room temperature and filtered through a pad of diatomite to remove Pd/C, and the filtrate was concentrated to give 2-benzylhexahydro-1H-pyrrolo[3,4-c]pyridine-1,3(2H)-dione 8e which was used in the next step directly.

Step 5

To a solution of 2-benzylhexahydro-1H-pyrrolo[3,4-c]pyridine-1,3(2H)-dione 8e (9.84 g, 40.3 mmol) in 120 mL THF was added $LiAlH_4$ (3.06 g, 80.6 mmol) at 0° C. under $N_2$ atmosphere. The reaction mixture was heated to reflux for 2 h until it turned clear. The mixture was cooled to room temperature then further cooled down to 0° C. using ice bath, then was added dropwisely 3 mL water, 3 mL 15% aq. NaOH, and 9 mL water successively. After being warmed to room temperature and stirred for 30 min, the mixture was filtered, and the filtrate was concentrated to give light yellow oil 2-benzyloctahydro-1H-pyrrolo[3,4-c]pyridine 8f which was used directly without further purification.

Step 6

To a solution of 2-benzyloctahydro-1H-pyrrolo[3,4-c]pyridine 8f (8.7 g, 40.3 mmol) and diisopropylethylamine (11.4 mL, 80.6 mmol) in 100 mL dichloromethane was added a solution of di-tert-butyl dicarbonate (13.06 g, 60.45 mmol in 15 mL dichloromethane) dropwisely at 0° C. under $N_2$ atmosphere. The ice bath was removed after the completion of addition, and the mixture was warmed to room temperature and stirred for 2 h until it turned clear. To the reaction mixture 100 mL water was added, the aqueous mixture was extracted with dichloromethane (2×50 mL). The combined organic layers were washed with 50 mL water and 50 mL brine successively, dried over anhydrous $Na_2SO_4$, filtered, and concentrated to give a residue which was purified by silica gel column chromatography (2% MeOH/DICHLOROMETHANE) to give tert-butyl 2-benzylhexahydro-1H-pyrrolo[3,4-c]pyridine-5(6H)-carboxylate 8g.

MS-ESI calc'd. [M+H]$^+$ 317, found 317.

Step 7

A solution of tert-butyl 2-benzylhexahydro-1H-pyrrolo[3,4-c]pyridine-5(6H)-carboxylate 8g (1.5 g, 4.7 mmol) and 300 mg dry Pd(OH)$_2$ (10%) in 120 mL THF was placed under H$_2$ (3 MPa) atmosphere and stirred at 60° C. for 24 h. The mixture was cooled to room temperature and filtered to remove Pd(OH)$_2$, the filtrate was concentrated and purified by silica gel column chromatography (50%-100% MeOH/DICHLOROMETHANE) to give tert-butyl hexahydro-1H-pyrrolo[3,4-c]pyridine-5(6H)-carboxylate 8 h (0.5 g, yield: 50%).

MS-ESI calc'd. [M+H]$^+$ 227, found 227.

Step 8

From tert-butyl hexahydro-1H-pyrrolo[3,4-c]pyridine-5(6H)-carboxylate 8 h (90 mg, 0.40 mmol) and isoquinoline-5-sulfonyl chloride 1c (116 mg, 0.510 mmol), the compound tert-butyl 2-(isoquinolin-5-ylsulfonyl)hexahydro-1H-pyrrolo[3,4-c]pyridine-5(6H)-carboxylate 8l was made following the procedure described for the synthesis of 1e (example 1) The crude product was used in the next step directly.

Step 9

The compound 5-((hexahydro-1H-pyrrolo[3,4-c]pyridin-2(3H)-yl) sulfonyl) isoquinoline 8 was made from tert-butyl 2-(isoquinolin-5-ylsulfonyl)hexahydro-1H-pyrrolo[3,4-c] pyridine-5 (6H)-carboxylate 8l(36 mg, 0.85 mmol) following the procedure described for the synthesis of 1 (example 1) (17 mg, light yellow solid, yield: 63%).

$^1$H NMR (400 MHz, $CD_3OD$): δ 9.42 (s, 1H), 8.69-8.59 (m, 2H), 8.53-8.35 (m, 3H), 7.87 (t, J=8.0 Hz, 1H), 3.53-3.46 (m, 2H), 3.44-3.37 (m, 2H), 3.28-3.22 (m, 1H), 3.19-2.95 (m, 3H), 2.62-2.44 (m, 2H), 1.92-1.86 (m, 1H), 1.74-1.63 (m, 1H).

MS-ESI calc'd. [M+H]$^+$ 318, found 318.

Example 9

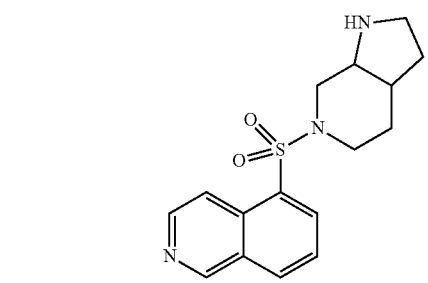 [SMILES: O=S(=O)(c1cccc2cnccc12)N1CCC2CCNC2C1]

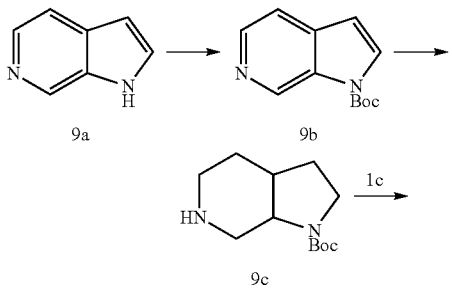

1H), 2.65-2.60 (m, 1H), 2.31 (brs, 1H), 2.23-2.05 (m, 1H), 1.96-1.75 (m, 2H), 1.65-1.55 (m, 1H).

MS-ESI calc'd. [M+H]+ 318, found 318.

Example 10

5-(isoquinolin-5-ylsulfonyl)-5-azaspiro[2.4]heptan-7-amine

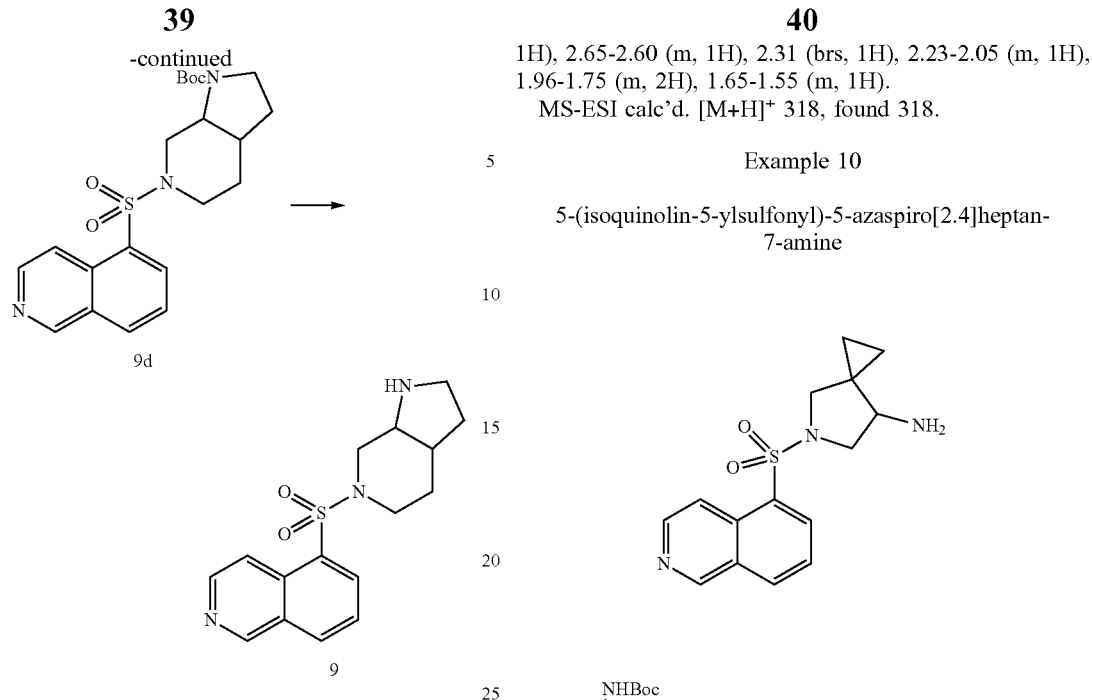

Step 1

To a solution of 1H-pyrrolo[2,3-c]pyridine 9a (1.00 g, 8.47 mmol) in 20 mL dichloromethane was added 2 mL triethylamine and di-tert-butyl dicarbonate (2.00 g, 9.17 mmol, in 10 mL dichloromethane) at 0° C. The mixture was warmed to room temperature and stirred for 16 h. The mixture was concentrated directly under reduced pressure to give tert-butyl 1H-pyrrolo[2,3-c]pyridine-1-carboxylate 9b which was used in the next step directly.

Step 2

To a solution of tert-butyl 1H-pyrrolo[2,3-c]pyridine-1-carboxylate 9b (1.2 g, 5.5 mmol) in 15 mL acetic acid was added PtO$_2$ (0.3 g, 1.3 mmol), the resulting mixture was placed under H$_2$ (4 MPa) atmosphere and stirred at room temperature for 12 h. The reaction mixture was filtered to remove PtO$_2$, the filtrate was concentrated under reduced pressure and purified by silica gel column chromatography (0-100% MeOH/dichloromethane) to give tert-butyl octahydro-1H-pyrrolo[2,3-c]pyridine-1-carboxylate 9c (600 mg, yield: 50%).

MS-ESI calc'd. [M+H]+ 227, found 227.

Step 3

From tert-butyl octahydro-1H-pyrrolo[2,3-c]pyridine-1-carboxylate 9c (100 mg, 0.44 mmol) and isoquinoline-5-sulfonyl chloride 1c (120 mg, 0.51 mmol), the compound tert-butyl 6-(isoquinolin-5-ylsulfonyl) octahydro-1H-pyrrolo[2,3-c]pyridine-1-carboxylate 9d was made following the procedure described for the synthesis of 1e (example 1) The crude was used directly without purification.

MS-ESI calc'd. [M+H]+ 418, found 418.

Step 4

The compound 5-((hexahydro-1H-pyrrolo[2,3-c]pyridin-6(2H)-yl)sulfonyl) isoquinoline 9 was made from tert-butyl 6-(isoquinolin-5-ylsulfonyl) octahydro-1H-pyrrolo[2,3-c]pyridine-1-carboxylate 9d (100 mg, 0.24 mmol) following the procedure described for the synthesis of 1 (example 1) (60 mg, yield: 79%)

$^1$H NMR (400 MHz, CD$_3$OD): δ 9.63 (s, 1H), 8.90 (d, J=6.0 Hz, 1H), 8.69 (d, J=6.0 Hz, 1H), 8.65-8.55 (m, 2H), 8.01 (t, J=7.8 Hz, 1H), 4.00-3.90 (m, 1H), 3.84-3.76 (m, 1H), 3.70-3.65 (m, 1H), 3.51-3.36 (m, 2H), 3.15-2.98 (m,

Step 1

From tert-butyl 5-azaspiro[2.4]heptan-7-ylcarbamate 10a (50 mg, 0.25 mmol) and isoquinoline-5-sulfonyl chloride 1c (75 mg, 0.32 mmol), the compound tert-butyl (5-(isoquinolin-5-ylsulfonyl)-5-azaspiro[2.4]heptan-7-yl)carbamate 10b was made following the procedure described for the synthesis of 1e (example 1). (95 mg, yellow oil, yield: 95%).

MS-ESI calc'd. [M+H]+ 404, found 404.

Step 2

The compound 5-(isoquinolin-5-ylsulfonyl)-5-azaspiro[2.4]heptan-7-amine 10 was made from tert-butyl (5-(isoquinolin-5-ylsulfonyl)-5-azaspiro[2.4]heptan-7-yl)carbamate 10b (30 mg, 0.074 mmol) following the procedure described for the synthesis of 1 (example 1). (10 mg, yellow solid, yield: 44%).

$^1$H NMR (400 MHz, D$_2$O): δ 9.40 (s, 1H), 8.60-8.58 (m, 2H), 8.55-8.45 (m, 2H), 7.88 (t, J=8.0 Hz, 1H), 3.79-3.69 (m, 3H), 3.43-3.41 (m, 1H), 3.15-3.10 (m, 1H), 0.96-0.89 (m, 1H), 0.85-0.75 (m, 1H), 0.68-0.61 (m, 1H), 0.48-0.42 (m, 1H).

MS-ESI calc'd. [M+H]$^+$ 304, found 304.

Example 11

N-ethyl-5-(isoquinolin-5-ylsulfonyl)-5-azaspiro[2.4]heptan-7-amine

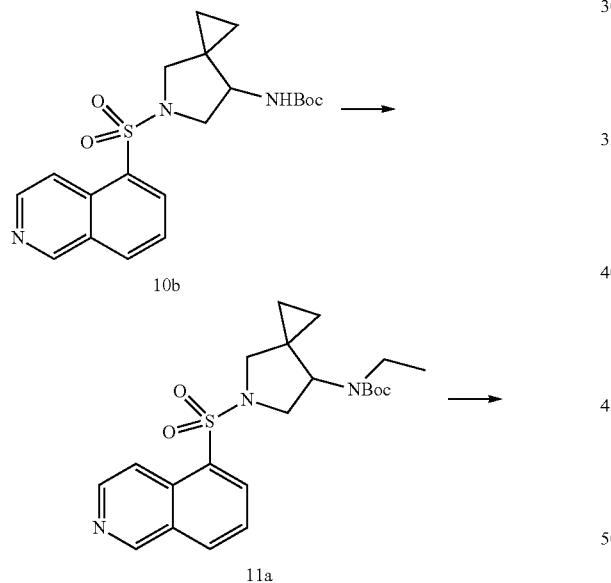

Step 1

To a solution of tert-butyl (5-(isoquinolin-5-ylsulfonyl)-5-azaspiro[2.4]heptan-7-yl) carbamate 10b (65 mg, 0.16 mmol, example 10) in 4 mL anhydrous N,N-dimethylformamide was added NaH (4.6 mg, 0.19 mmol) at 0° C. under N$_2$ atmosphere, the resulting mixture was stirred for 10 min at 0° C. before iodoethane (30 mg, 0.19 mmol) was added. The reaction mixture was stirred at room temperature for 1 h and added 20 mL brine. The aqueous mixture was extracted with EtOAc (30 mL×2), the combined organic layers were dried over Na$_2$SO$_4$, filtered, concentrated under reduced pressure. The crude product was purified by silica gel column chromatography (0-100% EtOAc/PE) to give tert-butyl ethyl (5-(isoquinolin-5-ylsulfonyl)-5-azaspiro[2.4]heptan-7-yl)carbamate 11a (15 mg, yellow oil, yield: 22%).

MS-ESI calc'd. [M+H]$^+$ 432, found 432.

Step 2

The compound N-ethyl-5-(isoquinolin-5-ylsulfonyl)-5-azaspiro[2.4]heptan-7-amine 11 was made from tert-butyl ethyl (5-(isoquinolin-5-ylsulfonyl)-5-azaspiro[2.4]heptan-7-yl)carbamate 11a (15 mg, 0.035 mmol) following the procedure described for the synthesis of 1 (example 1). (10 mg, yellow solid, yield: 87%)

$^1$H NMR (400 MHz, D$_2$O): δ 9.50 (s, 1H), 8.73 (d, J=6.4 Hz, 1H), 8.58-8.48 (m, 3H), 7.92 (d, J=8.0 Hz, 1H), 3.85-3.80 (m, 1H), 3.72-3.61 (m, 2H), 3.35-3.30 (m, 1H), 3.10-3.29 (m, 3H) 1.15 (t, J=7.2 Hz, 3H), 1.03-0.94 (m, 1H), 0.85-0.75 (m, 1H), 0.62-0.51 (m, 1H), 0.41-0.32 (m, 1H).

MS-ESI calc'd. [M+H]$^+$ 332, found 332.

Example 12

7-(isoquinolin-5-ylsulfonyl)decahydropyrrolo[3,4-b]azepine 12; 2-(isoquinolin-5-ylsulfonyl)decahydropyrrolo[3,4-c]azepine12'

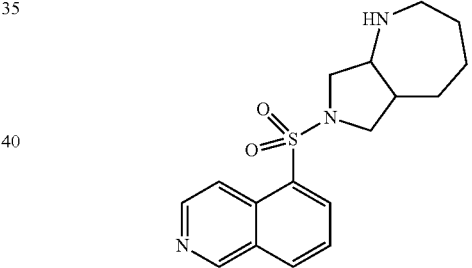

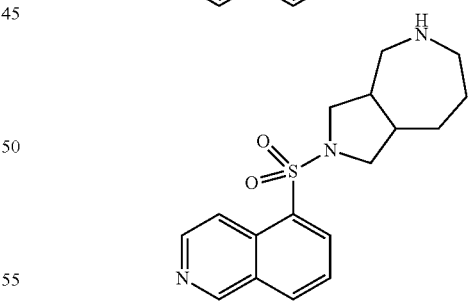

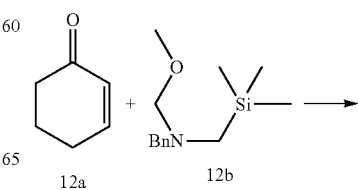

-continued

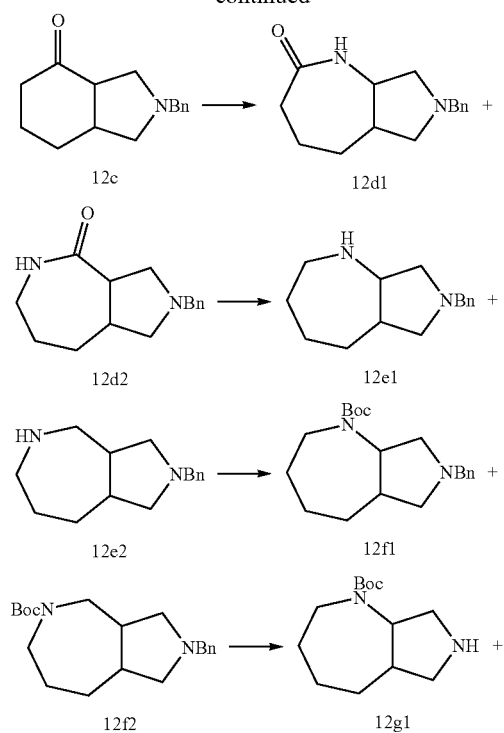

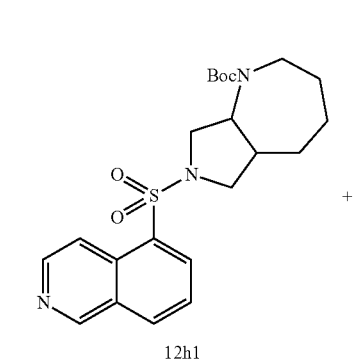

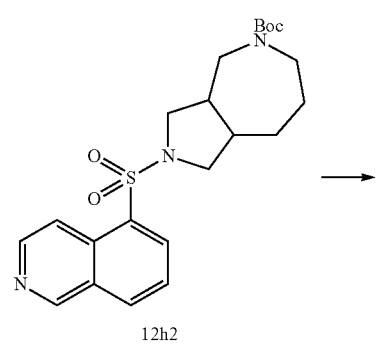

-continued

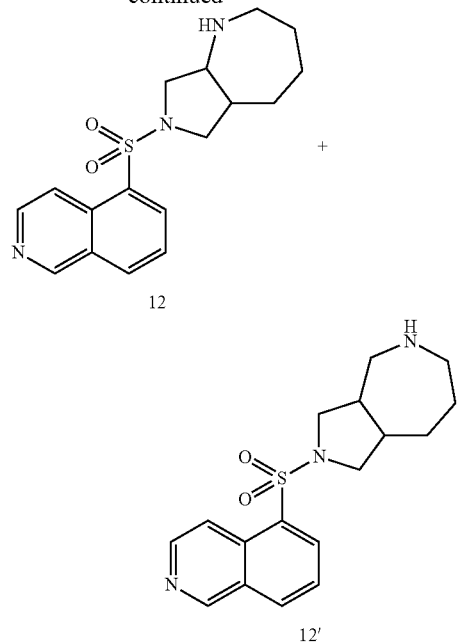

Step 1

To a solution of cyclohex-2-enone 12a (5.00 g, 52.1 mmol) in 50 mL dichloromethane was added N-benzyl-1-methoxy-N-((trimethylsilyl)methyl)methanamine 12b (7.74 g, 34.7 mmol) and 0.5 mL TFA and the resulting mixture was stirred at room temperature for 12 h under $N_2$ atmosphere. The reaction mixture was quenched by adding 20 mL saturated aq. $NaHCO_3$, then extracted with dichloromethane (20 mL×2), washed with 20 mL saturated aq. $NaHCO_3$. The combined organic layers were dried over anhydrous $Na_2SO_4$, and concentrated under reduced pressure to give 2-benzylhexahydro-1H-isoindol-4(2H)-one 12c which was used directly without further purification.

MS-ESI calc'd. $[M+H]^+$ 230, found 230.

Step 2

To a solution of 2-benzylhexahydro-1H-isoindol-4(2H)-one 12c (4.00 g, 17.5 mmol) in 50 mL chloroform was added $NaN_3$ (2.28 g, 35.0 mmol) and methylsulfonic acid (1.68 g, 17.5 mmol) at 0° C. under $N_2$ atmosphere. The resulting mixture was stirred at room temperature for 12 h, then was diluted by 50 mL water. The aqueous mixture was extracted with dichloromethane (30 mL×2), and the combined organic layers were washed with 30 mL saturated aq. $NaHCO_3$, dried over anhydrous $Na_2SO_4$, and concentrated to give a mixture of 7-benzyloctahydropyrrolo[3,4-b]azepin-2(1H)-one 12d1 and 2-benzyloctahydro pyrrolo[3,4-c]azepin-4 (2H)-one 12d2 which were used directly without further purification.

MS-ESI calc'd. $[M+H]^+$ 245, found 245.

Step 3

To a solution of mixture of 7-benzyloctahydropyrrolo[3,4-b]azepin-2(1H)-one 12d1 and 2-benzyloctahydropyrrolo [3,4-c]azepin-4(2H)-one 12d2 (2.80 g, 11.5 mmol) in 40 mL THF was added $LiAlH_4$ (872 mg, 22.8 mmol) at 0° C. under $N_2$ the resulting mixture was stirred at 60° C. for 2 h. then was added 1 mL water, 1 mL 15% aq. NaOH and 3 mL water in sequence at 0° C., then was stirred at room temperature for 30 min. The mixture was filtered, and the filtrate was extracted with EtOAc (20 mL×2). The combined organic layers were washed by 30 mL brine, dried over anhydrous Na$_2$SO$_4$, and concentrated to give a mixture of 7-benzyl-decahydropyrrolo[3,4-b]azepine 12e1 and 2-benzyldecahydropyrrolo[3,4-c]azepine 12e2 which were used directly without further purification.

Step 4

To a solution of mixture of 7-benzyldecahydropyrrolo[3,4-b]azepine 12e1 and 2-benzyldecahydropyrrolo[3,4-c]azepine 12e2 (2.62 g, 11.4 mmol) in 40 mL THF was added di-tert-butyl dicarbonate (3.73 g, 17.1 mmol) and triethylamine (1.73 g, 17.1 mmol) at room temperature under N$_2$ atmosphere, and the resulting mixture was stirred for 2 h at room temperature. The mixture was diluted by 50 mL water, then was extracted with EtOAc (30 mL×2). The combined organic layers were washed with saturated aq. NaHCO$_3$, dried over anhydrous Na$_2$SO$_4$, and concentrated to give a mixture of tert-butyl 7-benzyloctahydropyrrolo[3,4-b]azepine-1(2H)-carboxylate 12f1 and tert-butyl 2-benzyloctahydropyrrolo[3,4-c]azepine-5(1H)-carboxylate 12f2 which was used directly without further purification.

MS-ESI calc'd. [M+H]$^+$ 331, found 331.

Step 5

To a solution of mixture of tert-butyl 7-benzyloctahydropyrrolo[3,4-b]azepine-1(2H)-carboxylate 12f1 and tert-butyl 2-benzyloctahydropyrrolo[3,4-c]azepine-5(1H)-carboxylate 12f2 (1.90 g, 5.74 mmol) in 50 mL MeOH was added 100 mg wet Pd/C. The resulting mixture was placed under H$_2$ (1 atm) atmosphere and stirred at 50° C. for 2 h. The mixture was filtered, and the filtrate was concentrated under reduced pressure to get a mixture of tert-butyl octahydropyrrolo[3,4-b]azepine-1 (2H)-carboxylate 12g1 and tert-butyl octahydropyrrolo[3,4-c]azepine-5(1H)-carboxylate 12g2 which was used directly without further purification.

MS-ESI calc'd. [M+H]$^+$ 241, found 241.

Step 6

From a mixture of tert-butyl octahydropyrrolo[3,4-b]azepine-1(2H)-carboxylate 12g1 and tert-butyl octahydropyrrolo[3,4-c]azepine-5(1H)-carboxylate 12g2 (800 mg, 3.33 mmol) and isoquinoline-5-sulfonyl chloride 1c (910 mg, 4.00 mmol), a mixture of tert-butyl7-(isoquinolin-5-ylsulfonyl)octahydropyrrolo[3,4-b]azepine-1(2H)-carboxylate 12 h1 and tert-butyl 2-(isoquinolin-5-ylsulfonyl)octahydropyrrolo[3,4-c]azepine-5(1H)-carboxylate 12 h2 were made following the procedure described for the synthesis of 1e (example 1). Both 12 h1 and 12 h2 were used directly without purification.

MS-ESI calc'd. [M+H]$^+$ 432, found 432.

Step 7

Compounds 7-(isoquinolin-5-ylsulfonyl)decahydropyrrolo[3,4-b]azepine 12 (284 mg, yield: 26%); 2-(isoquinolin-5-ylsulfonyl)decahydropyrrolo[3,4-c]azepine12' (32 mg). were made from tert-butyl7-(isoquinolin-5-ylsulfonyl)octahydropyrrolo[3,4-b]azepine-1(2H)-carboxylate 12 h1 and tert-butyl 2-(isoquinolin-5-ylsulfonyl)octahydropyrrolo[3,4-c]azepine-5(1H)-carboxylate 12 h2 (1.43 g, 3.30 mmol) following the procedure described for the synthesis of 1 (example 1).

12: $^1$H NMR (400 MHz, CDCl$_3$): δ 9.28 (s, 1H), 8.62 (m, 1H), 8.52 (m, 1H), 8.33 (m, 1H), 8.17 (d, J=8.0 Hz, 1H), 7.66 (t, J=8.0 Hz, 1H), 3.79-3.74 (m, 1H), 3.59-3.55 (m, 1H), 3.49-3.44 (m, 1H), 3.10-3.07 (m, 1H), 2.86-2.77 (m, 3H), 2.43-2.36 (m, 2H), 1.70-1.63 (m, 3H), 1.37-1.32 (m, 3H).

12': $^1$H NMR (400 MHz, CDCl$_3$): δ 9.35 (s, 1H), 8.66 (m, 1H), 8.53 (m, 1H), 8.35 (m, 1H), 8.18 (d, J=8.0 Hz, 1H), 7.68 (t, J=8.0 Hz, 1H), 3.72-3.70 (m, 1H), 3.64-3.62 (m, 1H), 3.07-3.00 (m, 1H), 2.98-2.93 (m, 3H), 2.84 (m, 1H), 1.99 (m, 1H), 1.85-1.83 (m, 2H), 1.70-1.67 (m, 3H), 1.66-1.51 (m, 1H), 1.16-1.14 (m, 1H).

Example 13

4-(isoquinolin-5-ylsulfonyl)-4-azaspiro[2.4]heptan-7-amine

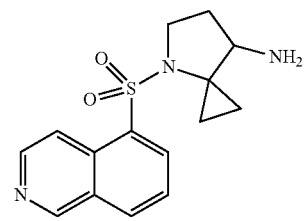 [SMILES: NC1CCN(S(=O)(=O)c2cccc3cnccc23)C12CC2]

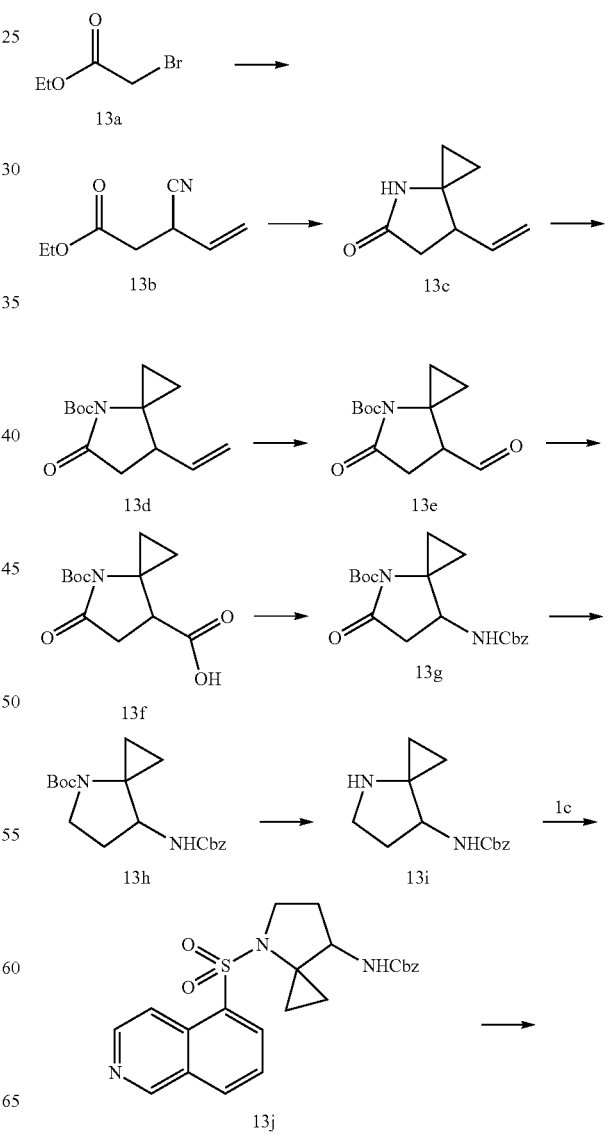

-continued

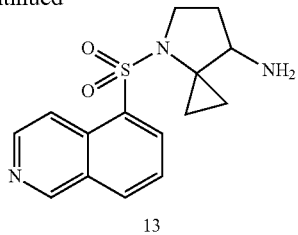

13

Step 1

To a solution of diisopropylamine (41.6 g, 0.41 mol) in 1.5 L THF was added n-butyl lithium (150 mL, 0.375 mol) dropwise at −78° C. under $N_2$ atmosphere at −78° C. After the completion of addition, the mixture was stirred for another 1 h at −78° C. then was added but-2-enenitrile (22.78 g, 0.34 mol) dropwisely. The resulting mixture was stirred for 1 h at −78° C., then was added ethyl 2-bromoacetate 13a (56.8 g, 0.34 mol) dropwisely at −78° C. and further stirred for 1 h after the completion of addition. 2.0 L saturated aq. $NH_4Cl$ was added to quench the reaction, and the resulting aqueous mixture was extracted with EtOAc (500 mL×3), and the combined organic layers were washed with water 500 mL and brine 500 mL successively, dried over anhydrous $Na_2SO_4$, filtered, and concentrated under reduced pressure to give a residue which was purified by silica gel column chromatography (0-100% EtOAc/PE) to give ethyl 3-cyanopent-4-enoate 13b (13.5 g, colorless oil, yield: 34%).

$^1$H NMR (400 MHz, $CDCl_3$): δ 5.83-5.71 (m, 1H), 5.51 (m, 1H), 5.34 (m, 1H), 4.20 (m, 2H), 3.79-3.71 (m, 1H), 2.81-2.73 (m, 1H), 2.69-2.61 (m, 1H), 1.28 (m, 3H).

Step 2

To a solution of ethyl 3-cyanopent-4-enoate 13b (6 g, 39.2 mmol) in 1 L anhydrous ether were added (i-PrO)$_4$Ti (11.76 mL, 39.2 mmol) and ethyl magnesium bromide (21.6 mL, 64.8 mmol, 3 M in THF) dropwisely in sequence at room temperature under $N_2$ atmosphere. The resulting mixture was stirred for 3 h at room temperature until starting material disappeared. Water (36 mL) was added to quench the reaction and the resulting suspension solution was filtered, and the filtrate was concentrated under reduced pressure to give a residue which was purified by silica gel column chromatography (0-100% EtOAc/PE) to give 7-vinyl-4-azaspiro[2.4]heptan-5-one 13c (3.3 g, white solid, yield: 63%)

$^1$H NMR (400 MHz, $CDCl_3$): δ 6.09 (brs, 1H), 5.68-5.60 (m, 1H), 5.08-5.00 (m, 2H), 3.0-2.96 (m, 1H), 2.70-2.64 (m, 1H), 2.40-2.36 (m, 1H), 0.83-0.75 (m, 2H), 0.65-0.58 (m, 2H).

MS-ESI calc'd. [M+H]$^+$ 138, found 138.

Step 3

To a solution of 7-vinyl-4-azaspiro[2.4]heptan-5-one 13c (1.2 g, 8.75 mmol) in 29 mL anhydrous acetonitril was added 4-N,N-dimethylaminopyridine (110 mg, 0.875 mmol) and di-tert-butyl dicarbonate (2.86 g, 13.1 mmol, in 10 mL acetonitril) dropwisely, and the resulting mixture was stirred for 5 h at room temperature. The reaction mixture was poured to 25 mL water, extracted with EtOAc (30 mL×3). The combined organic layers were dried over anhydrous $Na_2SO_4$, filtered, and the filtrate was concentrated under reduced pressure to give a residue which was purified by silica gel column chromatography (0-100% EtOAc/PE) to give tert-butyl 5-oxo-7-vinyl-4-azaspiro[2.4]heptane-4-carboxylate 13d (1.2 g, brown solid, yield: 55%)

$^1$H NMR (400 MHz, $CDCl_3$): δ 5.66-5.57 (m, 1H), 5.13-5.06 (m, 2H), 2.77-2.72 (m, 2H), 2.48-2.43 (m, 1H), 1.62-1.60 (m, 1H), 1.51 (s, 9H), 1.43-1.41 (m, 1H), 0.67-0.65 (m, 1H), 0.54-0.51 (m, 1H).

MS-ESI calc'd. [M+H]$^+$ 238, found 238.

Step 4

To a solution of tert-butyl 5-oxo-7-vinyl-4-azaspiro[2.4]heptane-4-carboxylate 13d (3.4 g, 14.3 mmol) in a mixed solvent of 34 mL MeOH and 51 mL $H_2O$ was added sodium periodate (9.2 g, 43 mmol) and osmium (VIII) oxide (55 mg, 0.22 mmol) at room temperature, and continuously stirred for 4 h. The reaction was quenched by addition of 40 mL water, the mixture was extracted with EtOAc (40 mL×3). The combined organic layers were dried over anhydrous $Na_2SO_4$, filtered, and concentrated to give a residue which was purified by silica gel column chromatography (0-100% EtOAc/PE) to give tert-butyl 7-formyl-5-oxo-4-azaspiro[2.4]heptane-4-carboxylate 13e (2.6 g, brown oil, yield: 76%).

MS-ESI calc'd. [M+H]$^+$ 240, found 240.

Step 5

To a solution of tert-butyl 7-formyl-5-oxo-4-azaspiro[2.4]heptane-4-carboxylate 13e (2.60 g, 10.9 mmol) in a mixed solvent of 87 mL tertiary butanol and 87 mL THF was added 2-butene (22.7 mL), $NaClO_2$ (979 mg, 10.9 mmol) and $NaH_2PO_3 \cdot 2H_2O$ (3.39 g, 21.8 mmol) in 63 mL water at 0° C. The resulting mixture was stirred at room temperature for 16 h and adjusted pH to ~4 using diluted hydrochloric acid, extracted with EtOAc (50 mL×3). The combined organic layers were dried over anhydrous $Na_2SO_4$, filtered, and the filtrate was concentrated under reduced pressure to give 4-(tert-butoxycarbonyl)-5-oxo-4-azaspiro[2.4]heptane-7-carboxylic acid 13f (2 g, light yellow solid, yield: 75%).

$^1$H NMR (400 MHz, DMSO): δ 12.76 (brs, 1H), 2.83-2.72 (m, 2H), 2.56-2.55 (m, 1H), 1.69-1.66 (m, 1H), 1.41 (s, 9H), 1.35-1.33 (m, 1H), 0.79-0.73 (m, 2H).

MS-ESI calc'd. [M+H]$^+$ 226, found 256.

Step 6

To a solution of 4-(tert-butoxycarbonyl)-5-oxo-4-azaspiro[2.4]heptane-7-carboxylic acid 13f (2.31 g, 9.02 mmol) in 30 mL toluene was added N,N-diisopropylethylamine (1.51 g, 11.7 mmol) and diphenyl phosphorazidate (3.23 g, 11.7 mmol) at 0° C., then the resulting mixture was stirred at 90° C. for 0.5 h. The reaction was then cooled down to room temperature and was added benzyl alcohol (1.07 g, 9.92 mmol) and stirred for 16 h at room temperature before the reaction was quenched by addition of 40 mL water and extracted with EtOAc (40 mL×3), the combined organic layers were dried over anhydrous $Na_2SO_4$, filtered, the filtrate was concentrated under reduced pressure to give a residue which was purified by silica gel column chromatography (0-100% EtOAc/PE) to give tert-butyl 7-(((benzyloxy)carbonyl)amino)-5-oxo-4-azaspiro[2.4]heptane-4-carboxylate 13g (1.8 g, white solid, yield: 56%).

MS-ESI calc'd. [M+H]$^+$ 361, found 361.

Step 7

To a solution of tert-butyl 7-(((benzyloxy)carbonyl)amino)-5-oxo-4-azaspiro[2.4]heptane-4-carboxylate 13g (200 mg, 0.56 mmol) in 3 mL THF was added borane in dimethyl sulfide ether (3.9 mL, 11.7 mmol, 3 M in dimethyl sulfide ether) at 0° C. under $N_2$ atmosphere. The resulting mixture was stirred at 60° C. for 1 h, then poured into 20 mL ice water, and extracted with EtOAc (20 mL×3). The combined organic layers were dried over anhydrous $Na_2SO_4$, filtered, and the filtrate was concentrated under reduced pressure was and purified by silica gel column chromatography (0-100% EtOAc/PE) to give tert-butyl 7-(((benzyloxy)carbonyl) amino)-4-azaspiro[2.4]heptane-4-carboxylate 13 h (30 mg, colorless oil, yield: 16%).

MS-ESI calc'd. [M+H]⁺ 347, found 347.

Step 8

From tert-butyl 7-(((benzyloxy)carbonyl) amino)-4-azaspiro[2.4]heptane-4-carboxylate 13 h (100 mg, 0.39 mmol) the compound benzyl 4-azaspiro[2.4]heptan-7-ylcarbamate 13i was made following the procedure described for the synthesis of 5f (example 5). (101 mg, white solid, yield: 100%).

MS-ESI calc'd. [M+H]⁺ 247, found 247.

Step 9

From benzyl 4-azaspiro[2.4]heptan-7-ylcarbamate 13i (70 mg, 0.27 mmol) and isoquinoline-5-sulfonyl chloride 1e (80 mg, 0.35 mmol), the compound benzyl (4-(isoquinolin-5-ylsulfonyl)-4-azaspiro[2.4]heptan-7-yl) carbamate 13j was made following the procedure described for the synthesis of 1e (example 1). (80 mg, colorless oil, yield: 68%).

MS-ESI calc'd. [M+H]⁺ 438, found 438.

Step 10

The compound 4-(isoquinolin-5-ylsulfonyl)-4-azaspiro[2.4]heptan-7-amine 13 was made from benzyl (4-(isoquinolin-5-ylsulfonyl)-4-azaspiro[2.4]heptan-7-yl) carbamate 13j following the procedure described for the synthesis of 5 (example 5). (11 mg, yellow solid, yield: 50%).

¹H NMR (400 MHz, CD₃OD): δ 9.42 (s, 1H), 8.65 (d, J=6.4 Hz, 1H), 8.54 (d, J=8.0 Hz, 1H), 8.47 (d, J=8.0 Hz, 1H), 8.38 (d, J=6.4 Hz, 1H), 7.87 (t, J=8.0 Hz, 1H), 4.16-4.12 (m, 1H), 3.67-3.64 (m, 1H), 3.41-3.38 (m, 1H), 2.53-2.51 (m, 1H), 2.09-2.07 (m, 1H), 1.24-1.21 (m, 1H), 1.15-1.13 (m, 1H), 0.80-0.73 (m, 2H).

MS-ESI calc'd. [M+H]⁺ 304, found 304.

Example 14

1-(isoquinolin-5-ylsulfonyl)decahydropyrrolo[3,2-b]azepine

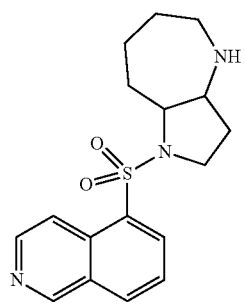 [SMILES: O=S(=O)(c1cccc2cnccc12)N1CCC2NCCCCC21]

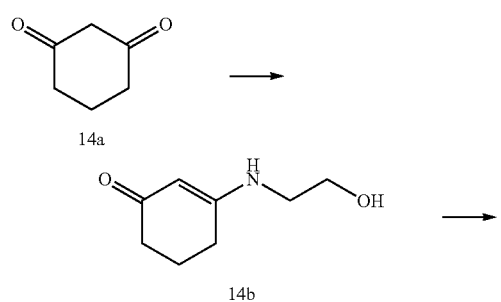

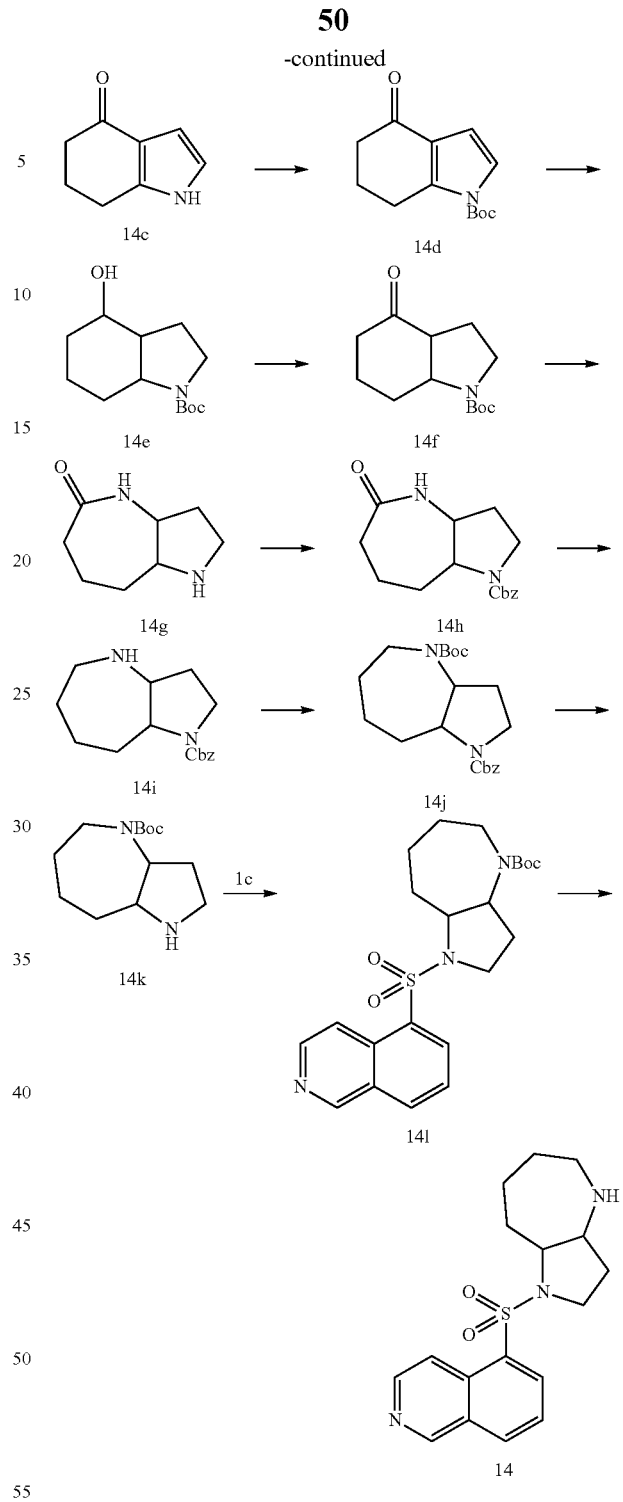

Step 1

To a solution of cyclohexane-1,3-dione 14a (5 g, 44.6 mmol) in 10 mL THF was added 2-aminoethanol (3.27 g, 53.5 mmol) at room temperature. The resulting suspension was poured into 90 mL toluene in a round bottom flask which was equipped with a Dean-Stark trap and heated to reflux overnight. The reaction mixture was cooled down to room temperature, concentrated under reduced pressure and purified by silica gel column chromatography (15% EtOAc/PE) to give 3-((2-hydroxyethyl)amino)cyclohex-2-enone 14b (4.30 g, yellow solid, yield: 62%).

¹H NMR (400 MHz, DMSO-d6): δ 4.80 (s, 1H), 3.47-3.57 (m, 2H), 3.14-3.22 (m, 2H), 3.05-2.95 (m, 1H), 2.27-2.35 (m, 2H), 2.09-2.03 (m, 1H), 1.68-1.82 (m, 2H).

Step 2

To a solution of 3-((2-hydroxyethyl)amino)cyclohex-2-enone 14b (3.70 g, 23.9 mmol) in 120 mL N,N-dimethylformamide was added triphenylphosphine palladium (552 mg, 0.48 mmol), trimethylbromobenzene (4.76 g, 23.9 mmol) and potassium carbonate (6.60 g, 47.8 mmol) at room temperature under $N_2$ atmosphere. The resulting mixture was refluxed at 150° C. for 2 h, cooled down to room temperature and concentrated under reduced pressure to give a residue which was then diluted with 100 mL EtOAc. The resulting mixture was washed with 100 mL brine, dried over anhydrous $Na_2SO_4$, filtered, concentrated, and purified by silica gel column chromatography (15% EtOAc/PE) to give 1,5,6,7-tetrahydro-1H-indol-4(5H)-one 14e (2.66 g, white solid, yield: 82%).

MS-ESI calc'd. $[M+H]^+$ 136, found 136.

Step 3

To a solution of 6,7-dihydro-1H-indol-4(5H)-one 14e (4.66 g, 34.5 mmol) in 120 mL acetonitrile was added N,N-diisopropylethylamine (9.3 mL, 51.7 mmol), di-tert-butyl dicarbonate (8.27 g, 37.9 mmol) and N,N-dimethylaminopyridine (82 mg, 0.69 mmol). The resulting mixture was stirred overnight at room temperature, concentrated under reduced pressure, and purified by silica gel column chromatography (10% EtOAc/PE) to give tert-butyl 4-oxo-4,5,6,7-tetrahydro-1H-indole-1-carboxylate 14d (7 g, white solid, yield: 86%).

Step 4

To a solution of tert-butyl 4-oxo-4,5,6,7-tetrahydro-1H-indole-1-carboxylate 14d (500 mg, 2.13 mmol) in 20 mL MeOH was added catalytic acetic acid and 50 mg $PtO_2$ at room temperature. The resulting mixture was stirred under $H_2$ (1 MPa) atmosphere at 50° C. for 3 h. After being cooled downed room temperature, the reaction mixture was concentrated and purified by silica gel column chromatography (50% EtOAc/PE) to give tert-butyl 4-hydroxyoctahydro-1H-indole-1-carboxylate 14e (400 mg, colorless oil, yield: 78%).

Step 5

To a solution of tert-butyl 4-hydroxyoctahydro-1H-indole-1-carboxylate 14e (700 mg, 2.9 mmol) in 35 mL dichloromethane was added Dess-Marteen Periodinane (2.46 g, 5.80 mmol) at 0° C. The resulting mixture was stirred at room temperature for 30 min. 50 mL saturated aq. $NaHCO_3$ was added, the mixture was extracted with dichloromethane (30 mL×3). The combined organic layers were washed with 50 mL brine, dried over anhydrous $Na_2SO_4$, filtered, concentrated, and purified by silica gel column chromatography (25% EtOAc/PE) to give tert-butyl 4-oxooctahydro-1H-indole-1-carboxylate 14f (470 mg, colorless oil, yield: 68%).

MS-ESI calc'd. $[M+H—C_4H_8]^+$ 184, found 184.

Step 6

To a solution of tert-butyl 4-oxooctahydro-1H-indole-1-carboxylate 14f (470 mg, 1.97 mmol) in 15 mL chloroform was added $NaN_3$ (250 mg, 3.85 mmol) and methylsulfonic acid (1.51 g, 15.8 mmol) at 0° C., the resulting mixture was stirred at 70° C. overnight. The reaction was cooled down to room temperature, 20 mL saturated aq. $NaHCO_3$ was added to quench the reaction. The aqueous mixture was extracted with EtOAc (40 mL), the organic layer was concentrated under vacuum to give octahydropyrrolo[3,2-b]azepin-5(1H)-one 14g which was used directly without further purification.

Step 7

To a solution of octahydropyrrolo[3,2-b]azepin-5(1H)-one 14g (303 mg, 1.97 mmol) in 15 mL water was added benzyl chloroformate (1.69 g, 9.85 mmol) and potassium carbonate (150 mg, 1.08 mmol) at 0° C. and the resulting mixture was warmed to room temperature and stirred for 4 h. The reaction mixture was extracted by EtOAc (20 mL×3), washed with 20 mL brine, dried over anhydrous $Na_2SO_4$, filtered and concentrated. The crude product was purified by prep. TLC (½ EtOAc/PE) to give benzyl 5-oxooctahydropyrrolo[3,2-b]azepine-1(2H)-carboxylate 14h (130 mg, colorless oil, yield: 23%).

¹H NMR (400 MHz, CDCl₃): δ 7.40-7.30 (m, 5H), 5.80 (s, 1H), 5.20-5.06 (m, 2H), 4.08-4.00 (m, 1H), 3.70-3.55 (m, 1H), 3.47-3.30 (m, 3H), 3.22-3.11 (m, 1H), 2.51-1.37 (m, 6H).

Step 8

To a solution of benzyl 5-oxooctahydropyrrolo[3,2-b]azepine-1(2H)-carboxylate 14h (180 mg, 0.63 mmol) in 5 mL THF was added borane (0.63 mL, 1.86 mmol, 3 M in dimethyl sulfide) at −78° C. The resulting mixture was warmed to 50° C. after addition and stirred for 4 h at this temperature. After being cooled down to room temperature, the reaction mixture was quenched by addition of 3 mL MeOH, The mixture was concentrated to give benzyl octahydropyrrolo[3,2-b]azepine-1(2H)-carboxylate 14l which was used directly without purification.

Step 9

To a solution of benzyl octahydropyrrolo[3,2-b]azepine-1(2H)-carboxylate 14l (171 mg, 0.625 mmol) in 3 mL dichloromethane was added N,N-diisopropylethylamine (161 mg, 1.25 mmol), 4-N,N-dimethylaminopyridine (8 mg, 0.025 mmol) and di-tert-butyl dicarbonate (273 mg, 1.25 mmol) successively at room temperature. The resulting mixture was stirred overnight, then was quenched by adding water. The mixture was extracted by dichloromethane (10 mL×3), the combined organic layers were washed by 20 mL brine, dried over anhydrous $Na_2SO_4$, filtered and concentrated. The crude product was purified by prep. TLC (1/1 EtOAc/PE) to give 1-benzyl 4-tert-butyl hexahydropyrrolo[3,2-b]azepine-1,4(2H,5H)-dicarboxylate 14j (180 mg, colorless oil, yield: 77%).

MS-ESI calc'd. $[M+H—C_4H_8]^+$ 319, found 319.

Step 10

To a solution of 1-benzyl 4-tert-butyl hexahydropyrrolo[3,2-b]azepine-1,4(2H,5H)-dicarboxylate 14j (180 mg, 0.48 mmol) in 20 mL THF was added 18 mg dry Pd/C at room temperature under $N_2$ atmosphere. The resulting mixture was stirred under $H_2$ (1 atm) atmosphere at room temperature for 2 h, then was filtered, and the filtrate was concentrated to give tert-butyl octahydropyrrolo[3,2-b]azepine-4(2H)-carboxylate 14k (30 mg, colorless oil, yield: 26%).

Step 11

From tert-butyl octahydropyrrolo[3,2-b]azepine-4(2H)-carboxylate 14k (30 mg, 0.12 mmol) and isoquinoline-5-sulfonyl chloride 1c (32 mg, 0.14 mmol), the compound tert-butyl 1-(isoquinolin-5-ylsulfonyl)octahydropyrrolo[3,2-b]azepine-4(2H)-carboxylate 14l was made following the procedure described for the synthesis of 1e (example 1). (30 mg, colorless oil, yield: 56%).

MS-ESI calc'd. $[M+H—C_4H_8]^+$ 432, found 432.

Step 12

The compound 1-(isoquinolin-5-ylsulfonyl)decahydropyrrolo[3,2-b]azepine 14 was made from tert-butyl 1-(isoquinolin-5-ylsulfonyl)octahydropyrrolo[3,2-b]azepine-4(2H)- carboxylate 14l (30 mg, 0.07 mmol) following the procedure described for the synthesis of 1 (example 1). (15 mg, white solid, yield: 65%).

¹H NMR (400 MHz, D₂O): δ 9.81-9.73 (m, 1H), 9.11-9.04 (m, 1H), 8.84-8.76 (m, 1H), 8.74-8.70 (m, 1H), 8.69-8.65 (m, 1H), 8.15-8.07 (m, 1H), 4.05-3.95 (m, 1H), 3.57-3.53 (m, 1H), 3.50-3.40 (m, 1H), 3.45-3.38 (m, 1H), 3.34-3.23 (m, 1H), 3.35-3.25 (m, 1H), 2.95-2.90 (m, 1H), 2.70-2.57 (m, 1H), 2.17-2.07 (m, 1H), 2.03-1.90 (m, 3H), 1.78-1.65 (m, 2H).

MS-ESI calc'd. [M+H]⁺ 332, found 332.

Example 15

5-((hexahydro-1H-pyrrolo[3,4-c]pyridin-5(6H)-yl)sulfonyl)isoquinoline

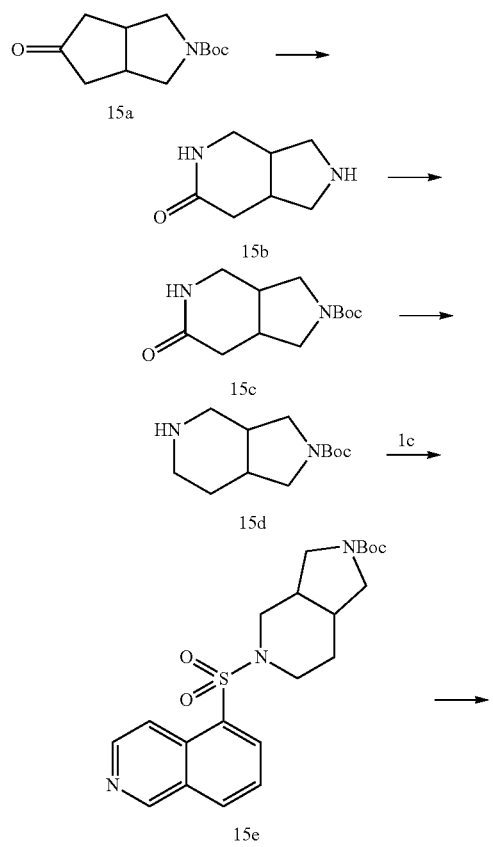

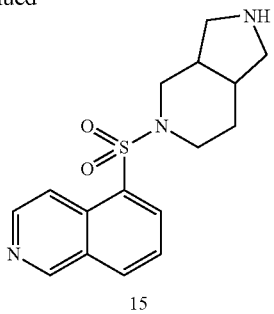

Step 1

To a solution of tert-butyl 5-oxohexahydrocyclopenta[c]pyrrole-2(1H)-carboxylate 15a (2 g, 8.89 mmol) in 10 mL chloroform was added NaN₃ (1.2 g, 18.4 mmol) and methylsulfonic acid (8.5 g, 88.9 mmol) successively. The resulting mixture was stirred at 70° C. for 2 h, and then cooled down to room temperature and adjusted pH to 7 using saturated aq. NaHCO₃, extracted with dichloromethane (20 mL×2). The combined organic layers were dried over anhydrous Na₂SO₄, concentrated to give yellow oil hexahydro-1H-pyrrolo[3,4-c]pyridin-6(2H)-one 15b which was used directly without purification.

Step 2

To a solution of hexahydro-1H-pyrrolo[3,4-c]pyridin-6(2H)-one 15b (1.22 g, 8.72 mmol) in 40 mL 10% aq. NaOH and THF (v/v=1/1) was added di-tert-butyl dicarbonate (3.87 g, 17.8 mmol) and stirred for 3 h at room temperature. The reaction mixture was extracted with EtOAc (30 mL×3), the combined organic layers were dried over anhydrous Na₂SO₄ and concentrated under reduced pressure. The crude product was purified by silica gel column chromatography (0-10% MeOH/EtOAc) to give tert-butyl 6-oxohexahydro-1H-pyrrolo[3,4-c]pyridine-2(3H)-carboxylate 15e (0.9 g, yellow oil, yield: 43%).

Step 3

To a solution of tert-butyl 6-oxohexahydro-1H-pyrrolo[3,4-c]pyridine-2(3H)-carboxylate 15e (600 mg, 2.5 mmol) in 20 mL THF was added a solution of LiAlH₄ (190 mg, 50 mmol) in 10 mL THF at −10° C. The resulting mixture was stirred at room temperature for 3 h. To the reaction mixture was added 0.19 mL water, 0.19 mL 15% aq. NaOH and 0.51 mL water in sequence, then the mixture was allowed to stir for another 30 min and filtered. The filtrate was concentrated under reduced pressure to give tert-butyl hexahydro-1H-pyrrolo[3,4-c]pyridine-2(3H)-carboxylate 15d as yellow oil which was used directly without purification.

Step 4

From tert-butyl hexahydro-1H-pyrrolo[3,4-c]pyridine-2(3H)-carboxylate 15d (200 mg, 0.88 mmol, crude from last step) and isoquinoline-5-sulfonyl chloride 1c (280 mg, 1.25 mmol), the compound tert-butyl 5-(isoquinolin-5-ylsulfonyl)hexahydro-1H-pyrrolo[3,4-c]pyridine-2(3H)-carboxylate 15e made following the procedure described for the synthesis of 1e (example 1). (80 mg, colorless oil, yield: 22%).

MS-ESI calc'd. [M+H−56]⁺ 362, found 362.

Step 5

The compound 5-((hexahydro-1H-pyrrolo[3,4-c]pyridin-5(6H)-yl)sulfonyl)isoquinoline 15 was made from tert-butyl 5-(isoquinolin-5-ylsulfonyl)hexahydro-1H-pyrrolo[3,4-c]pyridine-2(3H)-carboxylate 15e (80 mg, 0.19 mmol) following the procedure described for the synthesis of 1 (example 1). (51 mg, yellow oil, yield: 85%).

$^1$H NMR (400 MHz, CD$_3$OD): δ9.39 (s, 1H), 8.62 (d, J=8.0 Hz, 1H), 8.55 (d, J=8.0 Hz, 1H), 8.52-8.39 (m, 3H), 7.85 (t, J=8.0 Hz, 1H), 3.70-3.58 (m, 2H), 3.41-3.34 (m, 1H), 3.21-3.04 (m, 4H), 2.80-2.75 (m, 1H), 2.57-2.48 (m, 1H), 2.42-2.32 (m, 1H), 1.85-1.77 (m, 1H), 1.61-1.51 (m, 1H).

MS-ESI calc'd. [M+H]$^+$ 318, found 318.

Example 16

4-chloro-5-((hexahydropyrrolo[3,2-b]pyrrol-1(2H)-yl)sulfonyl)isoquinoline

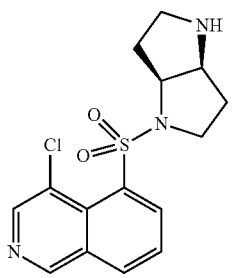 [SMILES: O=S(=O)(c1cccc2cncc(Cl)c12)N1CC[C@@H]2NCC[C@@H]21]

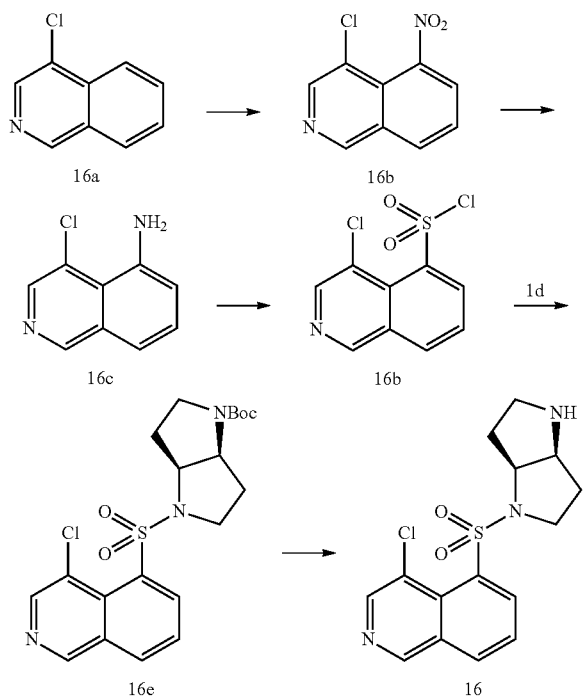

Step 1

To a solution of 4-chloroisoquinoline 16a (10.0 g, 61 mmol) in 55 mL concentrated sulfuric acid was added a solution of potassium nitrate (7.98 g, 79 mmol) in 69.0 mL concentrated sulfuric acid at −5° C. The resulting mixture was stirred at 0° C. for 1 h and then stirred at room temperature overnight. The reaction mixture was poured to 300 mL ice water, adjusted pH to 8 using solid Na$_2$CO$_3$, extracted with EtOAc (200 mL×2). The combined organic layers were dried over anhydrous Na$_2$SO$_4$, filtered, and concentrated. The crude product was purified by silica gel column chromatography (0-100% EtOAc/PE) to give 4-chloro-5-nitroisoquinoline 16b (11.2 g, white solid, yield: 88%).

MS-ESI calc'd. [M+H]$^+$ 209, found 209.

Step 2

To a solution of 4-chloro-5-nitroisoquinoline 16b (2.00 g, 9.62 mmol) in 34 mL concentrated hydrochloric acid was added SnCl$_2$.2H$_2$O (13 g, 57.7 mmol) at 0° C. The reaction mixture was stirred at 100° C. overnight, and then was cooled down to room temperature, adjusted pH to 8 using solid NaHCO$_3$. The mixture was extracted with EtOAc (100 mL×2), and the combined organic layers were dried over anhydrous Na$_2$SO$_4$ and filtered. The filtrate was concentrated and purified by silica gel column chromatography (0-100% EtOAc/PE) to give 4-chloroisoquinolin-5-amine 16c (1.57 g, yellow solid, yield: 92%).

MS-ESI calc'd. [M+H]$^+$ 179, found 179.

Step 3

To a solution of 4-chloroisoquinolin-5-amine (1.57 g, 8.82 mmol) in 14 mL concentrated hydrochloric acid was added a solution of NaNO$_2$ (620 mg, 8.82 mmol) in 2 mL water at −5° C., and the resulting mixture was allowed to stir for 1 h at this temperature, and then was transferred to a solution of 30 mL acetic acid with CuCl (224 mg, 2.20 mmol, in 2 mL water) saturated by SO$_2$ in one portion. The reaction was stirred at room temperature until no more bubble formed. To the reaction mixture was added 100 mL ice water, and the pH was adjusted to 8 using saturated aq. NaHCO$_3$. The mixture was then extracted with dichloromethane (100 mL×2), the combined organic layers were dried over anhydrous Na$_2$SO$_4$ and filtered. The filtrate was concentrated to give 4-chloroisoquinoline-5-sulfonyl chloride 16d (1.07 g, yellow solid, yield: 46%).

MS-ESI calc'd. [M+H]$^+$ 262, found 262.

Step 4

From cis-tert-butyl hexahydropyrrolo[3,4-b]pyrrole-1 (2H)-carboxylate 1d (30 mg, 0.142 mmol) and 4-chloroisoquinoline-5-sulfonyl chloride 16d (55.6 mg, 0.212 mmol), the compound tert-butyl 4-((4-chloroisoquinolin-5-yl)sulfonyl)hexahydropyrrolo[3,2-b]pyrrole-1(2H)-carboxylate 16e was made following the procedure described for the synthesis of 1e (example 1). (30 mg, yellow oil, yield: 48%).

MS-ESI calc'd. [M+H]$^+$ 438, found 438.

Step 5

The compound 4-chloro-5-((hexahydropyrrolo[3,2-b]pyrrol-1(2H)-yl)sulfonyl) isoquinoline 16 was made from tert-butyl 4-((4-chloroisoquinolin-5-yl)sulfonyl)hexahydropyrrolo[3,2-b]pyrrole-1(2H)-carboxylate 16e (30 mg, 0.092 mmol) following the procedure described for the synthesis of 1 (example 1). (20 mg, white solid, yield: 96%).

$^1$H NMR (400 MHz, D$_2$O): δ 9.21 (s, 1H), 8.63 (s, 1H), 8.40-8.30 (m, 2H), 7.80 (t, J=8.0 Hz, 1H), 4.77 (s, 1H), 4.53-4.50 (m, 1H), 3.71-3.66 (m, 1H), 3.35-3.31 (m, 2H), 3.47-3.44 (m, 1H), 2.54-2.44 (m, 1H), 2.28-2.23 (m, 1H), 2.16-2.11 (m, 2H).

MS-ESI calc'd. [M+H]$^+$ 338, found 338.

Example 17

4-chloro-5-((hexahydropyrrolo[3,4-b]pyrrol-5 (1H)-yl)sulfonyl)isoquinoline

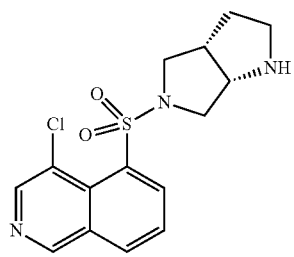 [SMILES: O=S(=O)(c1cccc2cncc(Cl)c12)N1C[C@@H]2CCN[C@@H]2C1]

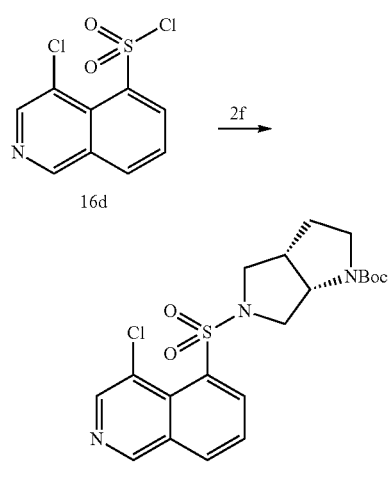

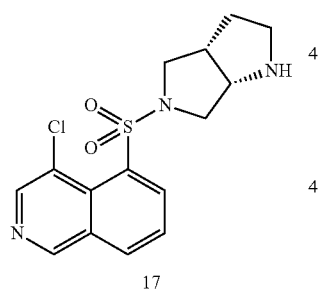

17

Step 1

From cis-tert-butyl hexahydropyrrolo[3,4-b]pyrrole-1(2H)-carboxylate 2f (30 mg, 0.142 mmol, example 2) and 4-chloroisoquinoline-5-sulfonyl chloride 16d (56 mg, 0.212 mmol), the compound tert-butyl 5-((4-chloroisoquinolin-5-yl)sulfonyl)hexahydropyrrolo[3,4-b]pyrrole-1(2H)-carboxylate 17e was made following the procedure described for the synthesis of 1e (example 1). (40 mg, yellow oil, yield: 65%).

MS-ESI calc'd. [M+H]⁺ 438, found 438.

Step 2

The compound 4-chloro-5-((hexahydropyrrolo[3,4-b]pyrrol-5(1H)-yl)sulfonyl)isoquinoline 17 was made from tert-butyl 5-((4-chloroisoquinolin-5-yl)sulfonyl)hexahydropyrrolo[3,4-b]pyrrole-1(2H)-carboxylate 17e (45 mg, 0.092 mmol) following the procedure described for the synthesis of 1 (example 1). (30 mg, white solid, yield: 96%).

¹H NMR (400 MHz, D₂O): δ9.25 (s, 1H), 8.64 (s, 1H), 8.45-8.35 (m, 2H), 7.81 (t, J=8.0 Hz, 1H), 4.43-4.39 (m, 1H), 3.80-3.75 (m, 2H), 3.65-3.60 (m, 1H), 3.47-3.44 (m, 1H), 3.37-3.23 (m, 3H), 2.27-2.17 (m, 1H), 1.96-1.89 (m, 1H).

MS-ESI calc'd. [M+H]⁺ 338, found 338.

Example 18

4-chloro-5-((hexahydro-1H-pyrrolo[3,4-b]pyridin-6(2H)-yl)sulfonyl)isoquinoline

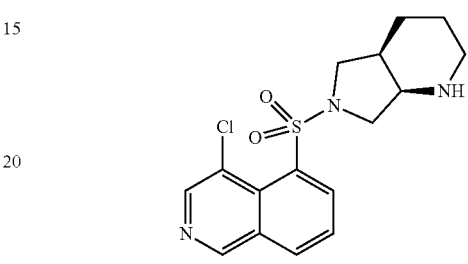

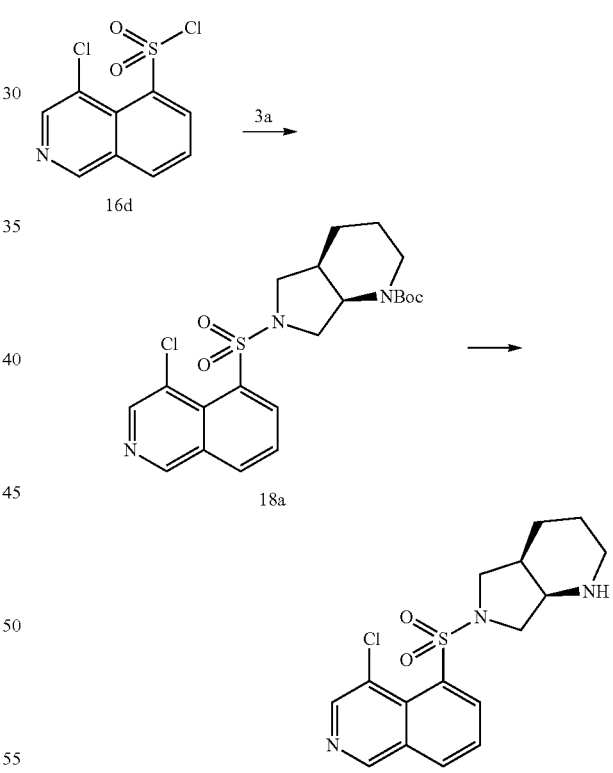

Step 1

From cis-tert-butyl octahydro-1H-pyrrolo[3,4-b]pyridine-1-carboxylate 3a (30 mg, 0.13 mmol, example 3) and 4-chloroisoquinoline-5-sulfonyl chloride 16d, the compound tert-butyl 6-((4-chloroisoquinolin-5-yl)sulfonyl)octahydro-1H-pyrrolo[3,4-b]pyridine-1-carboxylate 18a was made following the procedure described for the synthesis of 1e (example 1). (56 mg, yellow oil, yield: 93%).

MS-ESI calc'd. [M+H]⁺ 452, found 452.

Step 2

The compound 4-chloro-5-((hexahydro-1H-pyrrolo[3,4-b]pyridin-6(2H)-yl)sulfonyl)isoquinoline 18 was made from tert-butyl 6-((4-chloroisoquinolin-5-yl)sulfonyl)octahydro-1H-pyrrolo[3,4-b]pyridine-1-carboxylate 18a (15 mg, 0.035 mmol) following the procedure described for the synthesis of 1 (example 1). (10 mg, yellow solid, yield: 87%).

$^1$H NMR (400 MHz, D$_2$O): δ9.25 (s, 1H), 8.63-8.61 (s, 1H), 8.39-8.36 (m, 1H), 8.26-8.24 (m, 1H), 7.80 (t, J=8.0 Hz, 1H), 3.98-3.97 (m, 1H), 3.85-3.76 (m, 2H), 3.51 (t, J=10.0 Hz, 2H), 3.33-3.31 (m, 1H), 3.04-2.99 (m, 2H), 1.87-1.74 (m, 4H).

MS-ESI calc'd. [M+H]$^+$ 352, found 352.

Example 19

5-(3,6-diazabicyclo[3.2.0]heptan-3-ylsulfonyl)-4-chloroisoquinoline

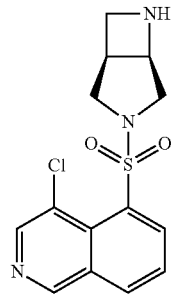 [SMILES: O=S(=O)(c1cccc2cncc(Cl)c12)N1C[C@H]2CN[C@H]2C1]

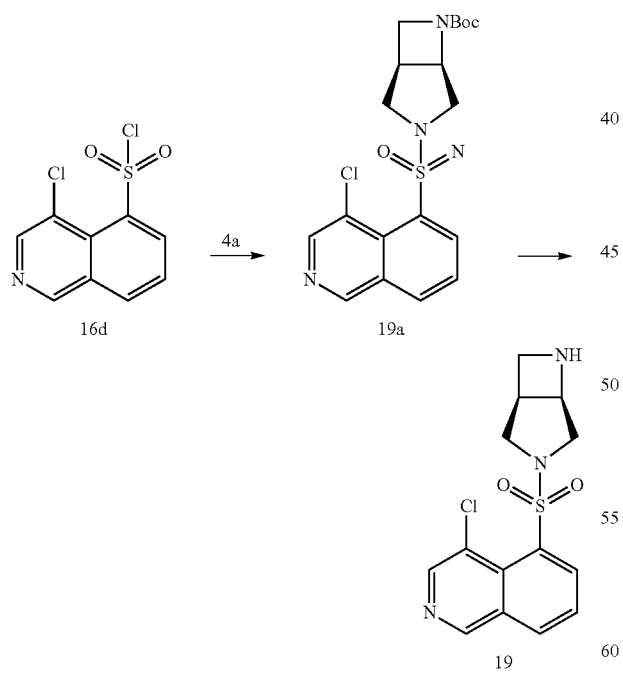

Step 1

From tert-butyl 3,6-diazabicyclo[3.2.0]heptane-6-carboxylate 4a (30 mg, 0.15 mmol) and 4-chloroisoquinoline-5-sulfonyl chloride 16d (44 mg, 0.17 mmol), the compound tert-butyl 3((4-chloroisoquinolin-5-yl) sulfonyl)-3,6-diazabicyclo[3.2.0]heptane-6-carboxylate 19a was made following the procedure described for the synthesis of 1e (example 1). (25 mg, yellow oil, yield: 39%).

MS-ESI calc'd. [M+H]$^+$ 418, found 418.

Step 2

The compound 5-(3,6-diazabicyclo[3.2.0]heptan-3-ylsulfonyl)-4-chloroisoquinoline 19 was made from tert-butyl 3((4-chloroisoquinolin-5-yl) sulfonyl)-3,6-diazabicyclo[3.2.0]heptane-6-carboxylate 19a (25 mg, 0.059 mmol) following the procedure described for the synthesis of 1 (example 1). (8 mg, white solid, yield: 38%).

$^1$H NMR (400 MHz, D$_2$O): δ 9.27 (s, 1H), 8.70 (brs, 1H), 8.49-8.43 (m, 2H), 7.85 (t, J=8.0 Hz, 1H), 5.06-5.01 (m, 1H), 4.26-4.21 (m, 1H), 4.10-4.07 (m, 1H), 3.83-3.91 (m, 2H), 3.69-3.64 (m, 1H), 3.61-3.54 (m, 1H), 3.52-3.48 (m, 1H).

MS-ESI calc'd. [M+H]$^+$ 318, found 318.

Example 20

6-((4-chloroisoquinolin-5-yl)sulfonyl)decahydro-1,6-naphthyridine

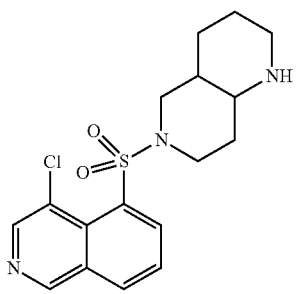 [SMILES: O=S(=O)(c1cccc2cncc(Cl)c12)N1CCC2NCCCC2C1]

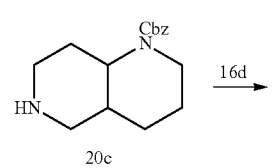

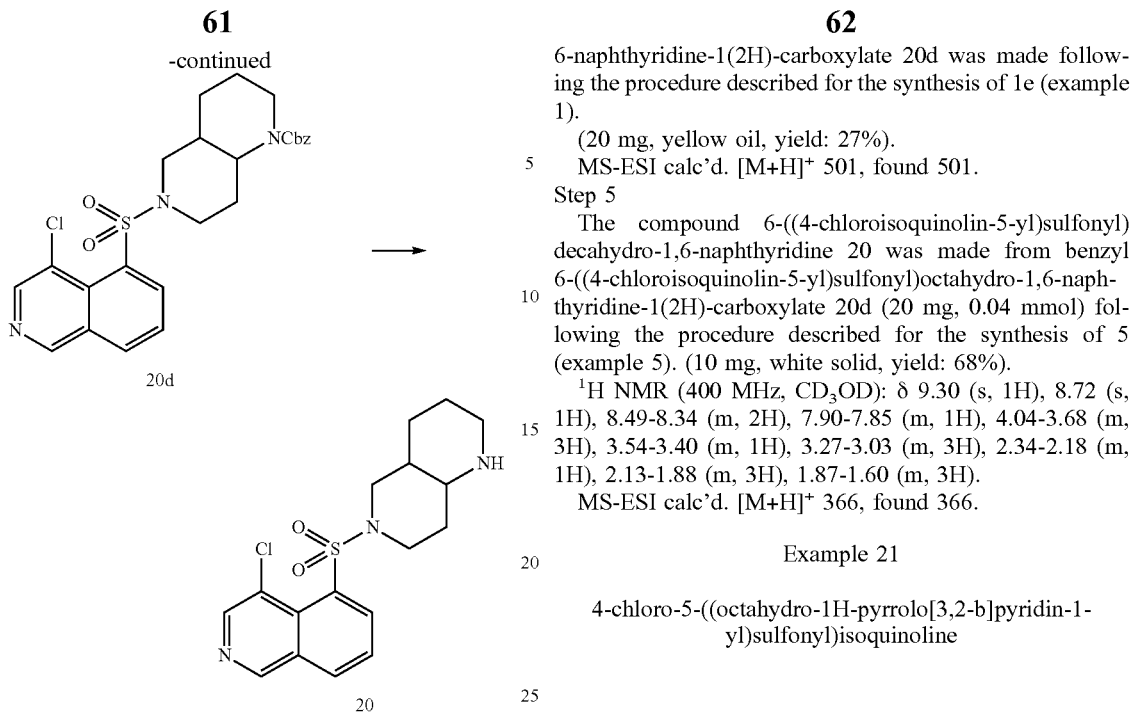

6-naphthyridine-1(2H)-carboxylate 20d was made following the procedure described for the synthesis of 1e (example 1).

(20 mg, yellow oil, yield: 27%).

MS-ESI calc'd. [M+H]⁺ 501, found 501.

Step 5

The compound 6-((4-chloroisoquinolin-5-yl)sulfonyl)decahydro-1,6-naphthyridine 20 was made from benzyl 6-((4-chloroisoquinolin-5-yl)sulfonyl)octahydro-1,6-naphthyridine-1(2H)-carboxylate 20d (20 mg, 0.04 mmol) following the procedure described for the synthesis of 5 (example 5). (10 mg, white solid, yield: 68%).

$^1$H NMR (400 MHz, CD$_3$OD): δ 9.30 (s, 1H), 8.72 (s, 1H), 8.49-8.34 (m, 2H), 7.90-7.85 (m, 1H), 4.04-3.68 (m, 3H), 3.54-3.40 (m, 1H), 3.27-3.03 (m, 3H), 2.34-2.18 (m, 1H), 2.13-1.88 (m, 3H), 1.87-1.60 (m, 3H).

MS-ESI calc'd. [M+H]⁺ 366, found 366.

Example 21

4-chloro-5-((octahydro-1H-pyrrolo[3,2-b]pyridin-1-yl)sulfonyl)isoquinoline

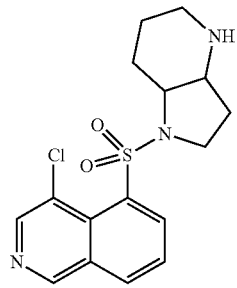 [SMILES: O=S(=O)(c1cccc2cncc(Cl)c12)N1CCC2NCCCC21]

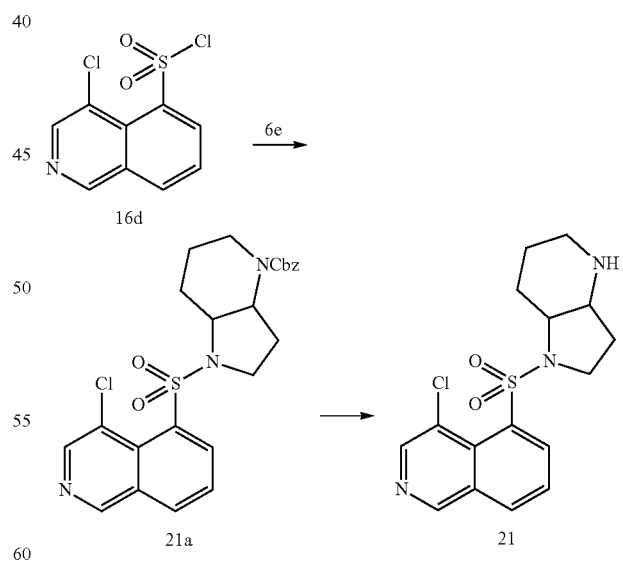

Step 1

To a solution of tert-butyl 1-(1-phenylethyl)octahydro-1,6-naphthyridine-6(2H)-carboxylate 5e (15 g, 0.044 mol) in 600 mL THF was added 1.5 g Pd(OH)$_2$ (20% on carbon). The resulting mixture was placed under H$_2$ (3 MPa) atmosphere and stirred at 80° C. for 16 h. After being cooled down to room temperature, the reaction mixture was filtered. The filtrate was concentrated under reduced pressure and purified by silica gel column chromatography (50% MeOH/EtOAc) to give tert-butyl octahydro-1,6-naphthyridine-6(2H)-carboxylate 20a (320 mg, yellow oil, yield: 3%).

MS-ESI calc'd. [M+H]⁺ 241, found 241.

Step 2

To a solution of tert-butyl octahydro-1,6-naphthyridine-6(2H)-carboxylate 20a (320 mg, 1.33 mmol) in 5 mL dichloromethane was added N,N-diisopropylethylamine (516 mg, 3.99 mmol) and benzyl chloroformate (340 mg, 2.0 mmol) at 0° C. The resulting mixture was stirred at room temperature for 1 h. The reaction mixture was concentrated, 20 mL water was added, and the resulting aqueous solution was extracted with EtOAc (30 mL×2). The combined organic layers were washed with 50 mL brine, dried over anhydrous Na$_2$SO$_4$, concentrated and purified by prep. TLC (3/1 PE/EtOAc) to give 1-benzyl 6-tert-butyl hexahydro-1,6-naphthyridine-1,6(2H,7H)-dicarboxylate 20b (275 mg, yellow oil, yield: 86%).

MS-ESI calc'd. [M+H]⁺ 375, found 375.

Step 3

From 1-benzyl 6-tert-butyl hexahydro-1,6-naphthyridine-1,6(2H,7H)-dicarboxylate 20b (275 mg, 0.73 mmol), the compound benzyl octahydro-1,6-naphthyridine-1(2H)-carboxylate 20c was made following the procedure described for the synthesis of 1 (example 1). (200 mg, white solid, yield: 96%).

MS-ESI calc'd. [M+H]⁺ 275, found 275.

Step 4

From benzyl octahydro-1,6-naphthyridine-1(2H)-carboxylate 20c (40 mg, 0.15 mmol) and 4-chloroisoquinoline-5-sulfonyl chloride 16d (42 mg, 0.16 mmol), the compound benzyl 6-((4-chloroisoquinolin-5-yl)sulfonyl)octahydro-1, Step 1

From benzyl hexahydro-1H-pyrrolo[3,2-b]pyridine-4(2H)-carboxylate 6e (30 mg, 0.12 mmol, example 6) and 4-chloroisoquinoline-5-sulfonyl chloride 16d (45 mg, 0.17 mmol), the compound benzyl 1-((4-chloroisoquinolin-5-yl)sulfonyl)hexahydro-1H-pyrrolo[3,2-b]pyridine-4(2H)-carboxylate 21a was made following the procedure described for the synthesis of 1e (example 1). (30 mg, yellow oil, yield: 36%).

MS-ESI calc'd. [M+H]+ 486, found 486.

Step 2

The compound 4-chloro-5-((octahydro-1H-pyrrolo[3,2-b]pyridin-1-yl)sulfonyl)isoquinoline 21 was made from benzyl 1-((4-chloroisoquinolin-5-yl)sulfonyl)hexahydro-1H-pyrrolo[3,2-b]pyridine-4 (2H)-carboxylate 21a (30 mg, 0.062 mmol) following the procedure described for the synthesis of 5 (example 5). (15 mg, white solid, yield: 71%).

1H NMR (400 MHz, D2O): δ9.33 (s, 1H), 8.78 (s, 1H), 8.55-8.50 (m, 2H), 7.91 (t, J=8.0 Hz, 1H), 4.64 (s, 1H), 4.18-4.13 (m, 1H), 4.03-3.98 (m, 1H), 3.80-3.75 (m, 2H), 3.17-3.04 (m, 1H), 2.41-2.36 (m, 2H), 1.97-1.80 (m, 3H), 1.58-1.55 (m, 1H).

MS-ESI calc'd. [M+H]+ 352, found 352.

Example 22

4-chloro-5-((hexahydropyrrolo[3,4-c]pyrrol-2(1H)-yl)sulfonyl)isoquinoline

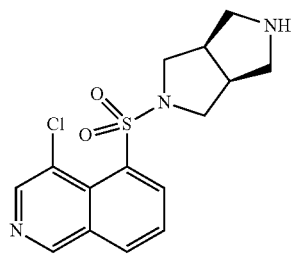 [SMILES: O=S(=O)(c1cccc2cncc(Cl)c12)N1C[C@H]2CNC[C@H]2C1]

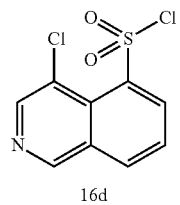

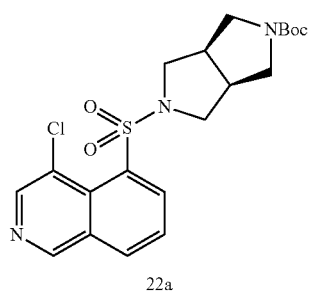

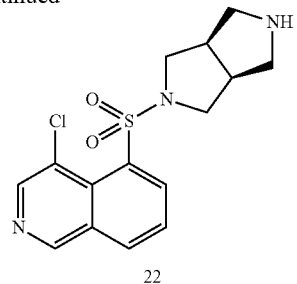

22

Step 1

From cis-tert-butyl hexahydropyrrolo[3,4-c]pyrrole-2(1H)-carboxylate 7a (30 mg, 0.14 mmo) and 4-chloroisoquinoline-5-sulfonyl chloride 16d (131 mg, 0.58 mmol), the compound tert-butyl 5((4-chloroisoquinolin-5-yl)sulfonyl)hexahydropyrrolo[3,4-c]pyrrole-2(1H)-carboxylate 22a was made following the procedure described for the synthesis of 1e (example 1). (50 mg, yellow oil, yield: 81%).

MS-ESI calc'd. [M+H]+ 438, found 438.

Step 2

The compound 4-chloro-5-((hexahydropyrrolo[3,4-c]pyrrol-2(1H)-yl)sulfonyl) isoquinoline 22 was made from tert-butyl 5-((4-chloroisoquinolin-5-yl)sulfonyl)hexahydropyrrolo[3,4-c]pyrrole-2(1H)-carboxylate 22a (50 mg, 0.11 mmol) following the procedure described for the synthesis of compound 1 (example 1). (35 mg, yellow solid, yield: 91%).

1H NMR (400 MHz, D2O): δ 9.23-9.21 (m, 1H), 8.64 (s, 1H), 8.78 (d, J=8.0 Hz, 1H), 8.43-8.38 (m, 2H), 3.61-3.54 (m, 4H), 3.45-3.40 (m, 2H), 3.21-3.19 (m, 2H), 3.05-3.00 (m, 2H).

MS-ESI calc'd. [M+H]+ 338, found 338.

Example 23

4-chloro-5-((hexahydro-1H-pyrrolo[3,4-c]pyridin-2(3H)-yl)sulfonyl)isoquinoline

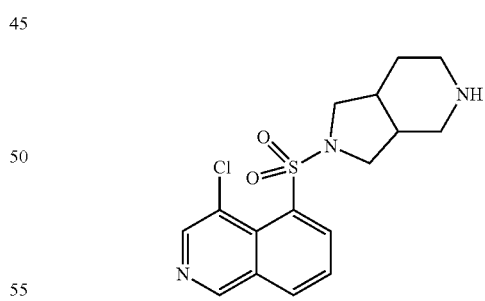

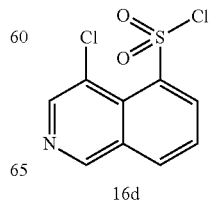

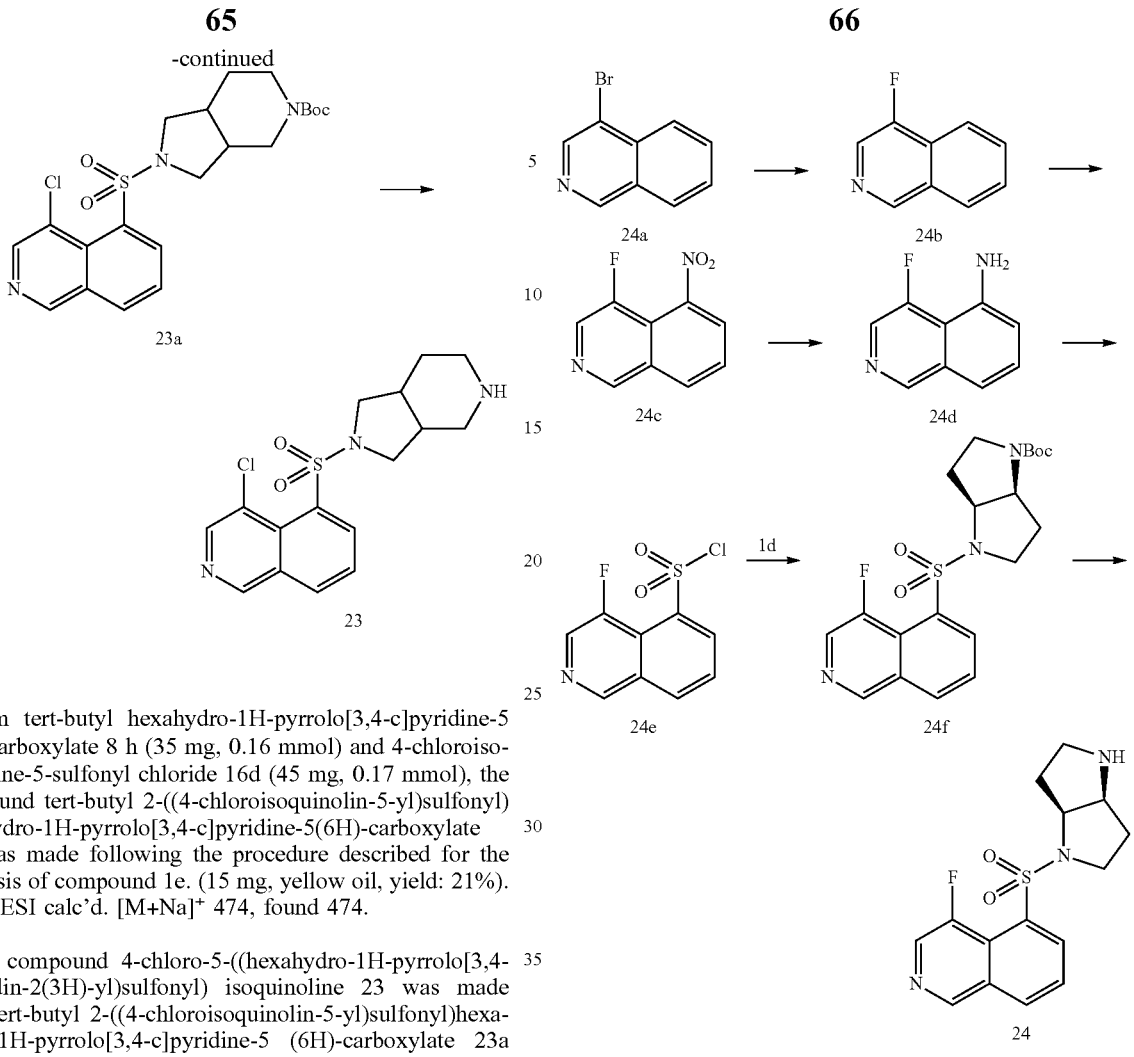

Step 1

From tert-butyl hexahydro-1H-pyrrolo[3,4-c]pyridine-5 (6H)-carboxylate 8 h (35 mg, 0.16 mmol) and 4-chloroisoquinoline-5-sulfonyl chloride 16d (45 mg, 0.17 mmol), the compound tert-butyl 2-((4-chloroisoquinolin-5-yl)sulfonyl)hexahydro-1H-pyrrolo[3,4-c]pyridine-5(6H)-carboxylate 23a was made following the procedure described for the synthesis of compound 1e. (15 mg, yellow oil, yield: 21%).

MS-ESI calc'd. [M+Na]$^+$ 474, found 474.

Step 2

The compound 4-chloro-5-((hexahydro-1H-pyrrolo[3,4-c]pyridin-2(3H)-yl)sulfonyl) isoquinoline 23 was made from tert-butyl 2-((4-chloroisoquinolin-5-yl)sulfonyl)hexahydro-1H-pyrrolo[3,4-c]pyridine-5 (6H)-carboxylate 23a (15 mg, 0.033 mmol) following the procedure described for the synthesis of compound 1. (10 mg, white solid, yield: 86%).

$^1$H NMR (400 MHz, D$_2$O): δ 9.28 (s, 1H), 8.70-8.68 (m, 1H), 8.45-8.41 (m, 2H), 7.85 (t, J=8.0 Hz, 1H), 3.70-3.60 (m, 2H), 3.52-3.47 (m, 2H), 3.41-3.36 (m, 1H), 3.25-3.14 (m, 3H), 2.89-2.75 (m, 2H), 2.08-2.02 (m, 1H), 1.90-1.82 (m, 1H).

MS-ESI calc'd. [M+H]$^+$ 352, found 352.

Example 24

4-fluoro-5-((hexahydropyrrolo[3,2-b]pyrrol-1(2H)-yl)sulfonyl)isoquinoline

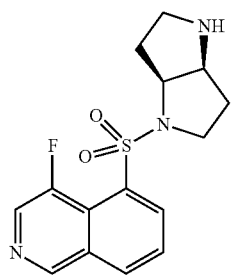 [SMILES: O=S(=O)(c1cccc2cncc(F)c12)N1CC[C@@H]2NCC[C@@H]21]

Step 1

To a solution of n-butyl lithium (133 mL, 332.5 mmol, 2.5 M in THF) in 760 mL THF was added a solution of 4-bromoisoquinoline 24a (20 g, 96.6 mmol) in 144 mL THF dropwise at −65° C. and the resulting mixture was stirred at this temperature for another 30 min after the completion of addition. A solution of N-fluorobenzenesulfonimide (66.68 g, 211.7 mmol) in 216 mL THF was added at −65° C. in 1 h dropwisely. After being stirred for another 1 h at this temperature, the reaction mixture was warmed to room temperature slowly with stirring, after the reaction is over, 300 mL saturated aq. NH$_4$Cl was added slowly, extracted with EtOAc (300 mL×3). The combined organic layers were washed with 300 mL brine, dried over anhydrous Na$_2$SO$_4$ and concentrated. The crude product was purified by silica gel column chromatography (0-100% EtOAc/PE) to give 4-fluoroisoquinoline 24b (8.5 g, red oil, yield: 60%).

Step 2

From 4-fluoroisoquinoline 24b (8.5 g, 57.8 mmol) the compound 4-fluoro-5-nitroisoquinoline 24c was made following the procedure described for the synthesis of 4-chloro-5-nitroisoquinoline 16b (example 16). (7.2 g, yellow oil, yield: 64.8%).

Step 3

From 4-fluoro-5-nitroisoquinoline 24c (7.2 g, 37.5 mmol) the compound 4-fluoroisoquinolin-5-amine 24d was made following the procedure described for the synthesis of 4-chloroisoquinolin-5-amine 16c (example 16). (5.5 g, yellow solid, yield: 90%).

Step 4

From 4-fluoroisoquinolin-5-amine 24d (5.5 g, 33.95 mmol) the compound 4-fluoroisoquinoline-5-sulfonyl chloride 24e was made following the procedure described for the synthesis of 4-chloroisoquinoline-5-sulfonyl chloride 16d (example 16). (4.5 g, white solid, yield: 54%).

$^1$H NMR (400 MHz, CDCl$_3$): δ 9.32-9.20 (m, 1H), 8.79-8.67 (m, 2H), 8.48-8.37 (m, 1H), 7.85 (t, J=8.0 Hz, 1H).

Step 5

From cis-tert-butyl hexahydropyrrolo[3,2-b]pyrrole-1(2H)-carboxylate 1d (30 mg, 0.142 mmol) and 4-fluoroisoquinoline-5-sulfonyl chloride 24e (35 mg, 0.14 mmol), the compound tert-butyl 4-((4-fluoroisoquinolin-5-yl)sulfonyl)hexahydropyrrolo[3,2-b]pyrrole-1(2H)-carboxylate 24f was made following the procedure described for the synthesis of 1e (example 1). (56 mg, yellow oil, yield: 94%).

MS-ESI calc'd. [M+Na]$^+$ 444, found 444.

Step 6

The compound 4-fluoro-5-((hexahydropyrrolo[3,2-b]pyrrol-1(2H)-yl)sulfonyl) isoquinoline 24 was made from tert-butyl 4-((4-fluoroisoquinolin-5-yl)sulfonyl)hexahydropyrrolo[3,2-b]pyrrole-1(2H)-carboxylate 24f (56 mg, 0.13 mmol) following the procedure described in example 1. (20 mg, white solid, yield: 42%).

$^1$H NMR (400 MHz, D$_2$O): δ 9.24 (s, 1H), 8.56-8.46 (m, 3H), 7.88 (t, J=8.0 Hz, 1H), 4.47 (m, 1H), 3.68 (m, 1H), 3.53-3.43 (m, 1H), 3.37-3.24 (m, 3H), 2.45-2.31 (m, 1H), 2.23-2.08 (m, 3H).

MS-ESI calc'd. [M+H]$^+$ 322, found 322.

Example 25

4-fluoro-5-((hexahydropyrrolo[3,4-b]pyrrol-5(1H)-yl)sulfonyl)isoquinoline

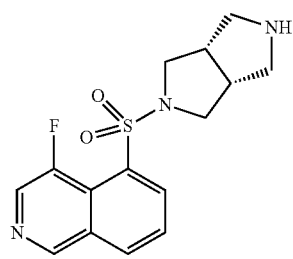 [SMILES: O=S(=O)(c1cccc2cncc(F)c12)N1C[C@H]2CNC[C@H]2C1]

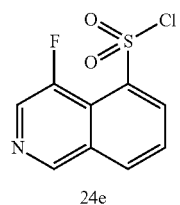

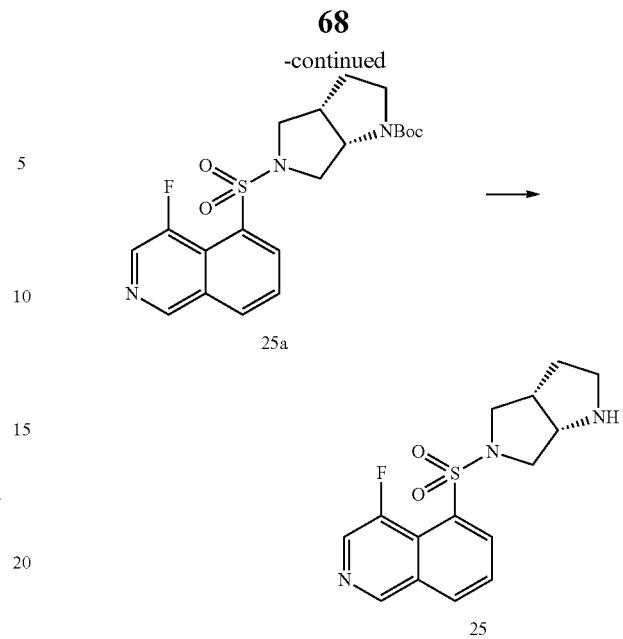

Step 1

From cis-tert-butyl hexahydropyrrolo[3,4-b]pyrrole-1(2H)-carboxylate 2f (55 mg, 0.24 mmol, example 2) and 4-fluoroisoquinoline-5-sulfonyl chloride 24e (50 mg, 0.2 mmol, example 24), the compound tert-butyl 5-((4-fluoroisoquinolin-5-yl)sulfonyl)hexahydropyrrolo[3,4-b]pyrrole-1(2H)-carboxylate 25a was made following the procedure described in example 1. (55 mg, yellow solid, yield: 58%).

MS-ESI calc'd. [M+H−56]$^-$ 366, found 366.

Step 2

The compound 4-fluoro-5-((hexahydropyrrolo[3,4-b]pyrrol-5(1H)-yl)sulfonyl) isoquinoline 25 was made from tert-butyl 5 ((4-fluoroisoquinolin-5-yl)sulfonyl)hexahydropyrrolo[3,4-b]pyrrole-1(2H)-carboxylate 25a (50 mg, 0.085 mmol) following the procedure described in example 1. (30 mg, white solid, yield: 78%).

$^1$H NMR (400 MHz, D$_2$O): δ 9.26 (s, 1H), 8.60-8.49 (m, 3H), 7.89 (t, J=7.2 Hz, 1H), 4.41 (t, J=6.4 Hz, 1H), 36.76-3.25 (m, 7H), 2.26-2.20 (m, 1H), 1.92-1.87 (m, 1H).

MS-ESI calc'd. [M+H]$^+$322, found 322.

Example 26

4-fluoro-5-((hexahydro-1H-pyrrolo[3,4-b]pyridin-6(2H)-yl)sulfonyl)isoquinoline

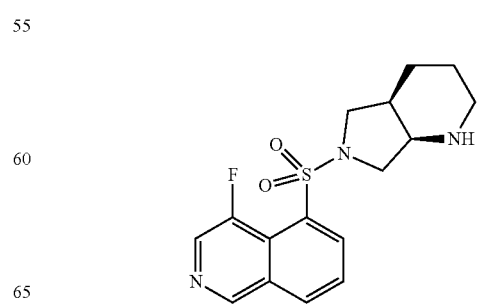

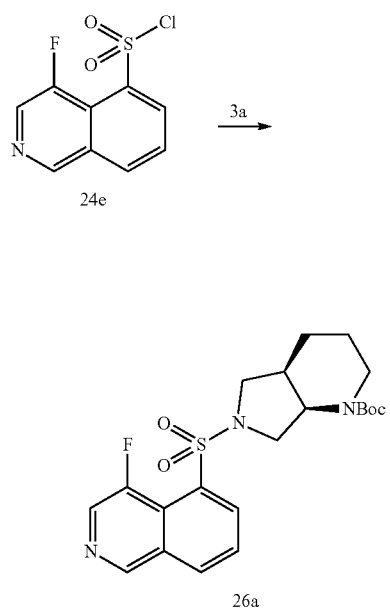

Example 27

5-(3,6-diazabicyclo[3.2.0]heptan-3-ylsulfonyl)-4-fluoroisoquinoline

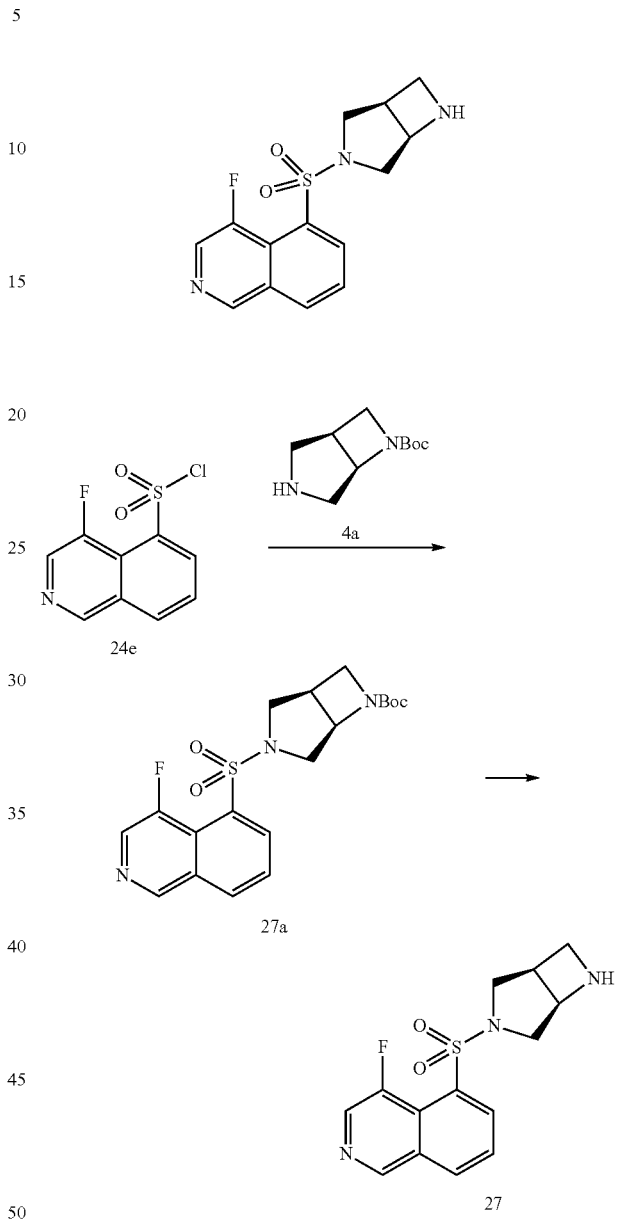

Step 1

4-fluoroisoquinoline-5-sulfonyl chloride 24e (45 mg, 0.2 mmol, example 24) and from cis-tert-butyl octahydro-1H-pyrrolo[3,4-b]pyridine-1-carboxylate 3a (50 mg, 0.22 mmol, example 3), the compound tert-butyl 6-((4-fluoroisoquinolin-5-yl)sulfonyl)octahydro-1H-pyrrolo[3,4-b]pyridine-1-carboxylate 26a was made following the procedure described in example 1. (50 mg, colorless oil, yield: 52%).

Step 2

The compound 4-fluoro-5-((hexahydro-1H-pyrrolo[3,4-b]pyridin-6(2H)-yl)sulfonyl) isoquinoline 26 was made from tert-butyl 6-((4-fluoroisoquinolin-5-yl)sulfonyl)octahydro-1H-pyrrolo[3,4-b]pyridine-1-carboxylate 26a (50 mg, 0.11 mmol) following the procedure described in example 1. (20 mg, white solid, yield: 42%).

$^1$H NMR (400 MHz, CD$_3$OD): δ 9.46 (s, 1H), 8.75-8.67 (m, 1H), 8.65-8.56 (m, 2H), 8.05-7.96 (m, 1H), 4.02-3.96 (m, 1H), 3.95-3.88 (m, 1H), 3.79-3.70 (m, 2H), 3.55-3.50 (m, 1H), 3.36-3.31 (m, 2H), 3.12-3.03 (m, 1H), 2.94-2.84 (m, 1H), 1.97-1.88 (m, 1H), 1.86-1.76 (m, 2H).

Step 1

From tert-butyl 3,6-diazabicyclo[3.2.0]heptane-6-carboxylate 4a (30 mg, 0.15 mmol) and 4-fluoroisoquinoline-5-sulfonyl chloride 24e (41 mg, 0.17 mmol, example 24), the compound tert-butyl 3((4-fluoroisoquinolin-5-yl)sulfonyl)-3,6-diazabicyclo[3.2.0]heptane-6-carboxylate 27a was made following the procedure described in example 1. (52 mg, yellow oil, yield: 84%).

MS-ESI calc'd. [M+Na]$^+$ 430, found 430.

Step 2

The compound 5-(3,6-diazabicyclo[3.2.0]heptan-3-ylsulfonyl)-4-fluoroisoquinoline 27 was made from tert-butyl 3((4-fluoroisoquinolin-5-yl)sulfonyl)-3,6-diazabicyclo[3.2.0]heptane-6-carboxylate 27a (52 mg, 0.13 mmol) following the procedure described in example 1. (20 mg, white solid, yield: 44%).

¹H NMR (400 MHz, D₂O): δ 9.42 (s, 1H), 8.71 (d, J=8.0 Hz, 1H), 8.66 (d, J=4.0 Hz, 1H), 8.59 (d, J=8.0 Hz, 1H), 7.99 (t, J=8.0 Hz, 1H), 4.99-4.95 (m, 1H), 4.22-4.17 (m, 1H), 4.00 (d, J=12.4 Hz, 1H), 3.85 (d, J=11.2 Hz, 1H), 3.78-3.74 (m, 1H), 3.55-3.48 (m, 2H), 3.38-3.34 (m, 1H).

MS-ESI calc'd. [M+H]⁺ 308, found 308.

Example 28

4-fluoro-5-((octahydro-1H-pyrrolo[3,2-b]pyridin-1-yl)sulfonyl)isoquinoline

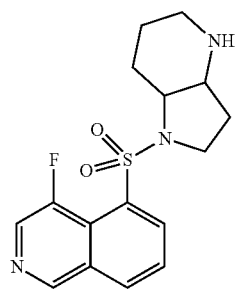 [SMILES: O=S(=O)(c1cccc2cncc(F)c12)N1CCC2NCCCC21]

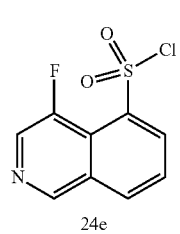

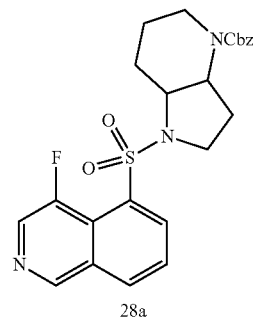

Step 1

From benzyl hexahydro-1H-pyrrolo[3,2-b]pyridine-4(2H)-carboxylate 6e (50 mg, 0.17 mmol, example 6) and 4-fluoroisoquinoline-5-sulfonyl chloride 24e (50 mg, 0.2 mmol, example 24), the compound benzyl 1-((4-fluoroisoquinolin-5-yl)sulfonyl)hexahydro-1H-pyrrolo[3,2-b]pyridine-4(2H)-carboxylate 28a was made following the procedure described in example 1. (72 mg, yellow oil, yield: 91%).

MS-ESI calc'd. [M+Na]⁺ 492, found 492.

Step 2

The compound 4-fluoro-5-((octahydro-1H-pyrrolo[3,2-b]pyridin-1-yl)sulfonyl) isoquinoline 28 was made from benzyl 1-((4-fluoroisoquinolin-5-yl)sulfonyl)hexahydro-1H-pyrrolo[3,2-b]pyridine-4(2H)-carboxylate 28a (72 mg, 0.15 mmol) following the procedure described for the synthesis of 6-(isoquinolin-5-ylsulfonyl)decahydro-1,6-naphthyridine 5 in example 5. (25 mg, white solid, yield: 49%).

¹H NMR (400 MHz, CD₃OD): δ 9.28 (s, 1H), 8.64 (d, J=8.0 Hz, 1H), 8.60 (d, J=4.0 Hz, 1H), 8.51 (d, J=8.0 Hz, 1H), 7.91 (t, J=8.0 Hz, 1H), 4.16-4.11 (m, 1H), 3.89-3.83 (m, 1H), 3.81-3.66 (m, 2H), 3.14-3.06 (m, 1H), 3.04-2.93 (m, 1H), 2.34-2.20 (m, 2H), 2.04-1.98 (m, 1H), 1.85-1.82 (m, 1H), 1.55-1.50 (m, 2H).

MS-ESI calc'd. [M+H]⁺ 336, found 336.

Example 29

4-fluoro-5-((hexahydropyrrolo[3,4-c]pyrrol-2(1H)-yl)sulfonyl)isoquinoline

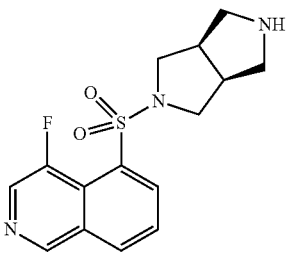 [SMILES: O=S(=O)(c1cccc2cncc(F)c12)N1C[C@H]2CNC[C@H]2C1]

Step 1

From cis-tert-butyl hexahydropyrrolo[3,4-c]pyrrole-2(1H)-carboxylate 7a (30 mg, 0.14 mmol, example 7) and 4-fluoroisoquinoline-5-sulfonyl chloride 24e (35 mg, 0.14 mmol), the compound tert-butyl 5-((4-fluoroisoquinolin-5-yl)sulfonyl)hexahydropyrrolo[3,4-c]pyrrole-2(1H)-carboxylate 29a was made following the procedure described in example 1. (55 mg, yellow oil, yield: 92%).

MS-ESI calc'd. [M+Na]+ 444, found 444.

Step 2

The compound 4-fluoro-5-((hexahydropyrrolo[3,4-c]pyrrol-2(1H)-yl)sulfonyl) isoquinoline 29 was made from tert-butyl 5-((4-fluoroisoquinolin-5-yl)sulfonyl)hexahydropyrrolo[3,4-c]pyrrole-2(1H)-carboxylate 29a (55 mg, 0.13 mmol) following the procedure described in example 1. (26 mg, white solid, yield: 55%).

¹H NMR (400 MHz, D₂O): δ 9.26 (brs, 1H), 8.58-8.53 (m, 2H), 8.49 (d, J=8.0 Hz, 1H), 7.89 (t, J=8.0 Hz, 1H), 3.61-3.56 (m, 2H), 3.54-3.47 (m, 2H), 3.45-3.42 (m, 2H), 3.19-3.14 (m, 2H), 2.98-2.91 (m, 2H).

MS-ESI calc'd. [M+H]+ 322, found 322.

Example 30

4-fluoro-5-((hexahydro-1H-pyrrolo[3,4-b]pyridin-6(2H)-yl)sulfonyl)isoquinoline

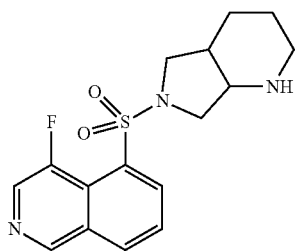 [SMILES: O=S(=O)(c1cccc2cncc(F)c12)N1CC2CCCNC2C1]

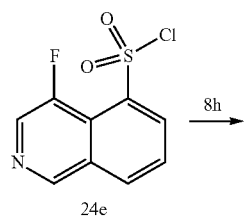

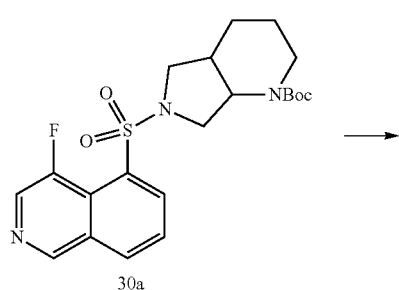

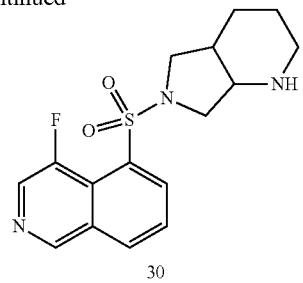

Step 1

From tert-butyl hexahydro-1H-pyrrolo[3,4-c]pyridine-5(6H)-carboxylate 8 h (30 mg, 0.13 mmol, example 8) and 4-fluoroisoquinoline-5-sulfonyl chloride 24e (33 mg, 0.13 mmol, example 24), the compound tert-butyl 6-((4-fluoroisoquinolin-5-yl)sulfonyl)octahydro-1H-pyrrolo[3,4-b]pyridine-1-carboxylate 30a was made following the procedure described in example 1. (17 mg, yellow oil, yield: 29%).

MS-ESI calc'd. [M+H]+ 436, found 436.

Step 2

The compound 4-fluoro-5-((hexahydro-1H-pyrrolo[3,4-b]pyridin-6(2H)-yl)sulfonyl) isoquinoline 30 was made from tert-butyl 6-((4-fluoroisoquinolin-5-yl)sulfonyl)octahydro-1H-pyrrolo[3,4-b]pyridine-1-carboxylate 30a (17 mg, 0.039 mmol) following the procedure described in example 1. (6 mg, white solid, yield: 46%).

¹H NMR (400 MHz, D₂O): δ 9.33 (s, 1H), 8.59 (d, J=5.6 Hz, 1H), 8.53-8.49 (m, 2H), 7.92 (t, J=8.0 Hz, 1H), 3.67-3.60 (m, 2H), 3.50-3.40 (m, 2H), 3.35-3.30 (m, 1H), 3.20-3.08 (m, 3H), 2.81-2.70 (m, 2H), 2.04-1.95 (m, 1H), 1.83-1.74 (m, 1H).

MS-ESI calc'd. [M+H]+ 336, found 336.

Example 31

4-(difluoromethyl)-5-((hexahydropyrrolo[3,2-b]pyrrol-1(2H)-yl)sulfonyl)isoquinoline

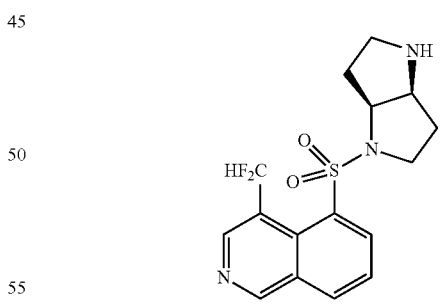

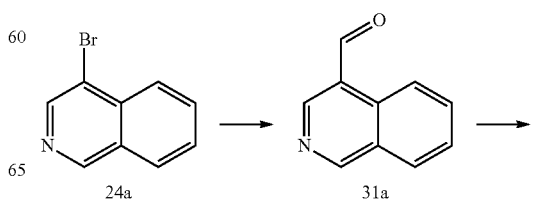

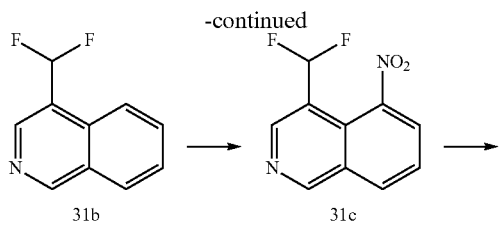

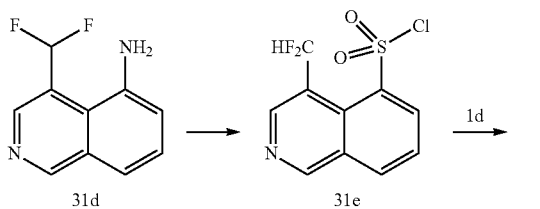

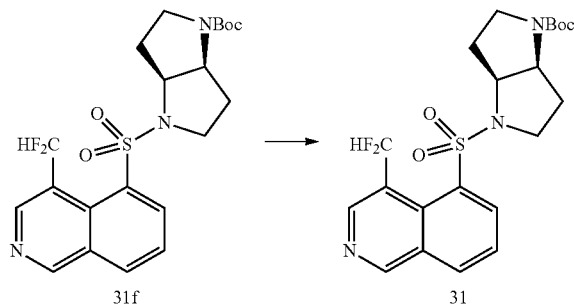

Step 1

To a solution of 4-bromoisoquinoline 24a (2.0 g, 9.6 mmol) in 30 mL re-distilled THF was added n-butyl lithium (4.0 mL, 10 mmol, 2.5 M in THF) dropwisely at −65° C. under $N_2$ atmosphere. The resulting mixture was stirred for 30 min at this temperature before N,N-dimethylformamide (730 mg, 10 mmol) was added dropwise, and stirred for additional 1 h at this temperature. After the reaction was over, 100 mL saturated aq. $NH_4Cl$ was added to the reaction mixture, and the mixture was extracted with EtOAc (50 mL×3). The combined organic layers were washed with 100 mL brine, dried over anhydrous $Na_2SO_4$, concentrated under reduced pressure. The crude was purified by silica gel column chromatography (0-100% EtOAc/PE) to give isoquinoline-4-carbaldehyde 31a (550 mg, yellow solid, yield: 36%).

$^1$H NMR (400 MHz, $CDCl_3$): δ 10.41 (s, 1H), 9.45 (s, 1H), 9.22 (d, J=8.4 Hz, 1H), 8.96 (s, 1H), 8.10 (d, J=8.4 Hz, 1H), 7.96-7.92 (m, 1H), 7.76 (t, J=8.4 Hz, 1H).

MS-ESI calc'd. $[M+H_3O]^+$ 176, found 176.

Step 2

To a solution of isoquinoline-4-carbaldehyde 31a (100 mg, 0.63 mmol) in 5 mL anhydrous dichloromethane was added diethylaminosulphur trifluoride (1.1 g, 6.3 mmol) at 0° C. under $N_2$ atmosphere dropwise. The resulting mixture was stirred at room temperature for 5 hours then quenched by pouring into 30 mL ice-water. The mixture was adjusted to pH 8-9 using saturated aq. $NaHCO_3$, then extracted with dichloromethane (20 mL×3). The combined organic layers were dried over anhydrous $Na_2SO_4$, filtered and concentrated under reduced pressure. The crude was purified by silica gel column chromatography (0-100% EtOAc/PE) to give 4-(difluoromethyl)isoquinoline 31b (80 mg, yellow oil, yield: 70%).

$^1$H NMR (400 MHz, $CDCl_3$): δ 9.36 (s, 1H), 8.66 (s, 1H), 8.21 (d, J=8.4 Hz, 1H), 8.07 (d, J=8.4 Hz, 1H), 7.86-7.73 (m, 1H), 7.75-7.65 (m, 1H), 7.07 (t, J=54.4 Hz, 1H).

MS-ESI calc'd. $[M+H]^+$ 180, found 180.

Step 3

The compound 4-(difluoromethyl)-5-nitroisoquinoline 31c was made from 4-(difluoromethyl)isoquinoline 31b (1.3 g, 7.2 mmol) following the procedure described in example 16. (1.16 g, yellow solid, yield: 71%).

$^1$H NMR (400 MHz, $CD_3OD$): δ 9.60 (s, 1H), 8.94 (s, 1H), 8.60 (d, J=8.0 Hz, 1H), 8.45 (d, J=8.0 Hz, 1H), 7.94 (t, J=8.0 Hz, 1H), 7.24 (t, J=56.0 Hz, 1H).

MS-ESI calc'd. $[M+H]^+$ 225, found 225.

Step 4

To a solution of 4-(difluoromethyl)-5-nitroisoquinoline 31c (100 mg, 0.45 mmol) in 30 mL ethanol was added wet Pd/C (30 mg, 10%) and hydrazine hydrate (22 mg, 0.45 mmol, 85%) under $N_2$ atmosphere. The resulting mixture was refluxed for 1 h, cooled down to room temperature and filtered. The filtrate was concentrated and purified by silica gel column chromatography (30% EtOAc/PE) to give 4-(difluoromethyl)isoquinolin-5-amine 31d (62 mg, yellow solid, yield: 78.5%).

$^1$H NMR (400 MHz, $CDCl_3$): δ 9.25 (s, 1H), 8.70 (s, 1H), 7.78-7.64 (m, 1H), 7.54-7.49 (m, 2H), 7.15-7.10 (m, 1H).

MS-ESI calc'd. $[M+H]^+$ 195, found 195.

Step 5

The compound 4-(difluoromethyl)isoquinoline-5-sulfonyl chloride 31e was made from 4-(difluoromethyl)isoquinolin-5-amine 31d (230 mg, 1.18 mmol) following the procedure described for the synthesis of 4-chloroisoquinoline-5-sulfonyl chloride 16d in example 16. (130 mg, yellow solid, yield: 39%).

MS-ESI calc'd. $[M+H]^+$ 278, found 278.

Step 6

From cis-tert-butyl hexahydropyrrolo[3,2-b]pyrrole-1(2H)-carboxylate 1d (37 mg, 0.24 mmol, example 1) and 4-(difluoromethyl)isoquinoline-5-sulfonyl chloride 31e (68 mg, 0.24 mmol), the compound tert-butyl 4-((4-(difluoromethyl)isoquinolin-5-yl)sulfonyl) hexahydropyrrolo[3,2-b]pyrrole-1(2H)-carboxylate 31f was made following the procedure described in example 1. (50 mg, yellow solid, yield: 46%).

MS-ESI calc'd. $[M+H]^+$ 454, found 454.

Step 7

The compound 4-(difluoromethyl)-5-((hexahydropyrrolo[3,2-b]pyrrol-1(2H)-yl)sulfonyl) isoquinoline 31 was made from tert-butyl 4-((4-(difluoromethyl)isoquinolin-5-yl)sulfonyl) hexahydropyrrolo[3,2-b]pyrrole-1(2H)-carboxylate 31f (50 mg, 0.11 mmol) following the procedure described in example 1. (25 mg, white solid, yield: 53%).

$^1$H NMR (400 MHz, $D_2O$): δ 9.69 (s, 1H), 9.06 (s, 1H), 8.63-8.60 (m, 2H), 8.21-7.94 (m, 2H), 4.66-4.48 (m, 2H), 3.64-3.61 (m, 1H), 3.54-3.49 (m, 1H), 3.32-3.28 (m, 2H), 2.44-2.39 (m, 1H), 2.24-2.22 (m, 1H), 2.07-2.05 (m, 2H).

MS-ESI calc'd. $[M+H]^+$ 354, found 354.

Example 32

4-(difluoromethyl)-5-((hexahydropyrrolo[3,4-b]pyrrol-5(1H)-yl)sulfonyl)isoquinoline

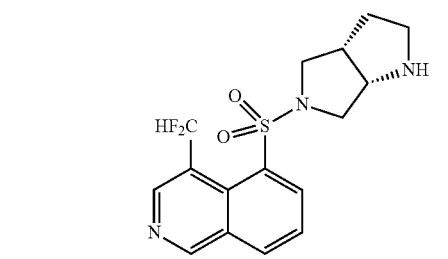

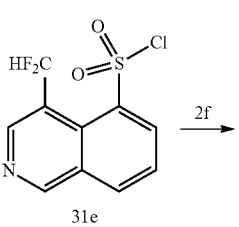

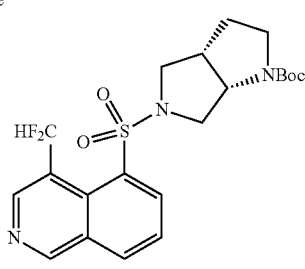

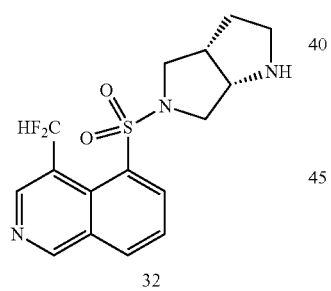

Step 1

From cis-tert-butyl hexahydropyrrolo[3,4-b]pyrrole-1(2H)-carboxylate 2f (37 mg, 0.24 mmol, example 2) and 4-(difluoromethyl)isoquinoline-5-sulfonyl chloride 31e (68 mg, 0.24 mmol, example 31), the compound tert-butyl 5-((4-(difluoromethyl)isoquinolin-5-yl)sulfonyl) hexahydropyrrolo[3,4-b]pyrrole-1(2H)-carboxylate 32a was made following the procedure described in example 1. (45 mg, yellow solid, yield: 41%).

MS-ESI calc'd. [M+H]+ 454, found 454.

Step 2

The compound 4-(difluoromethyl)-5-((hexahydropyrrolo[3,4-b]pyrrol-5(1H)-yl)sulfonyl) isoquinoline 32 was made from tert-butyl 5-((4-(difluoromethyl)isoquinolin-5-yl)sulfonyl) hexahydropyrrolo[3,4-b]pyrrole-1(2H)-carboxylate 32a (45 mg, 0.1 mmol) following the procedure described in example 1. (25 mg, white solid, yield: 60%).

1H NMR (400 MHz, D2O): δ 9.63 (s, 1H), 9.04 (s, 1H), 8.71-8.56 (m, 2H), 8.18-7.92 (m, 2H), 4.41-4.38 (m, 1H), 3.69-3.67 (m, 2H), 3.53-3.50 (m, 1H), 3.36-3.21 (m, 4H), 2.24-2.18 (m, 1H), 1.90-1.76 (m, 1H).

MS-ESI calc'd. [M+H]+ 354, found 354.

Example 33

4-(difluoromethyl)-5-((hexahydro-1H-pyrrolo[3,4-b]pyridin-6(2H)-yl)sulfonyl)isoquinoline

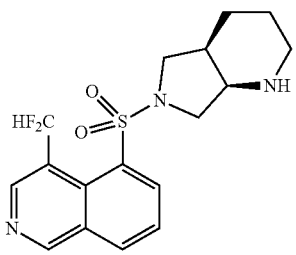

Step 1

From cis-tert-butyl octahydro-1H-pyrrolo[3,4-b]pyridine-1-carboxylate 3a (30 mg, 0.18 mmol, example 3) and 4-(difluoromethyl)isoquinoline-5-sulfonyl chloride 31e (50 mg, 0.18 mmol, example 31), the compound tert-butyl 6-((4-(difluoromethyl)isoquinolin-5-yl)sulfonyl)octahydro-1H-pyrrolo[3,4-b]pyridine-1-carboxylate 33a was made following the procedure described in example 1. (40 mg, yellow solid, yield: 47%).

MS-ESI calc'd. [M+H]+ 468, found 468.

Step 2

The compound 4-(difluoromethyl)-5-((hexahydro-1H-pyrrolo[3,4-b]pyridin-6(2H)-yl) sulfonyl)isoquinoline 33 was made from tert-butyl 6-((4-(difluoromethyl)isoquinolin-5-yl)sulfonyl)octahydro-1H-pyrrolo[3,4-b]pyridine-1-carboxylate 33a (40 mg, 0.085 mmol) following the procedure described in example 1. (10 mg, white solid, yield: 27%).

$^1$H NMR (400 MHz, D$_2$O): δ 9.64-9.59 (m, 1H), 9.03 (s, 1H), 8.57-8.47 (m, 2H), 8.21-7.92 (m, 2H), 3.97 (s, 1H), 3.79-3.74 (m, 2H), 3.64-3.61 (m, 1H), 3.46 (t, J=10.2 Hz, 1H), 3.32-3.28 (m, 1H), 3.00-2.92 (m, 2H), 1.84-1.72 (m, 4H).

MS-ESI calc'd. [M+H]$^+$ 368, found 368.

Example 34

5-(3,6-diazabicyclo[3.2.0]heptan-3-ylsulfonyl)-4-(difluoromethyl)isoquinoline

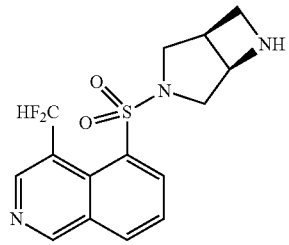

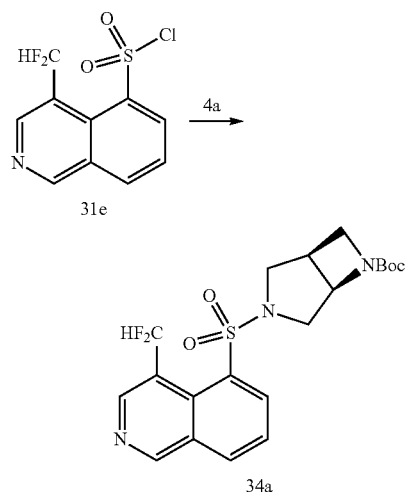

Step 1

From tert-butyl 3,6-diazabicyclo[3.2.0]heptane-6-carboxylate 4a (30 mg, 0.18 mmol, example 4) and 4-(difluoromethyl)isoquinoline-5-sulfonyl chloride 31e (50 mg, 0.18 mmol, example 31), the compound tert-butyl 3-((4-(difluoromethyl)isoquinolin-5-yl)sulfonyl)-3,6-diazabicyclo[3.2.0]heptanes-6-carboxylate 34a was made following the procedure described in example 1. (40 mg, yellow solid, yield: 50%).

MS-ESI calc'd. [M+H]$^+$ 440, found 440.

Step 2

The compound 5-(3,6-diazabicyclo[3.2.0]heptan-3-ylsulfonyl)-4-(difluoromethyl) isoquinoline 34 was made from tert-butyl 3-((4-(difluoromethyl)isoquinolin-5-yl)sulfonyl)-3,6-diazabicyclo[3.2.0]heptanes-6-carboxylate 34a (40 mg, 0.085 mmol) following the procedure described in example 1. (10 mg, white solid, yield: 26%).

$^1$H NMR (400 MHz, D$_2$O): δ 9.60 (s, 1H), 9.07 (s, 1H), 8.65-8.60 (m, 2H), 8.20 (t, J=53.2 Hz, 1H), 7.94 (t, J=8.0 Hz, 1H), 5.00-4.95 (m, 1H), 4.20-4.15 (m, 1H), 4.00-3.95 (m, 1H), 3.95-3.70 (m, 2H), 3.54-3.50 (m, 2H), 3.35-3.31 (m, 1H).

MS-ESI calc'd. [M+H]$^+$ 340, found 340.

Example 35

4-(difluoromethyl)-5-((hexahydropyrrolo[3,4-c]pyrrol-2(1H)-yl)sulfonyl)isoquinoline

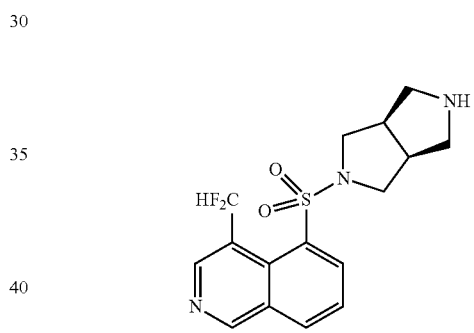

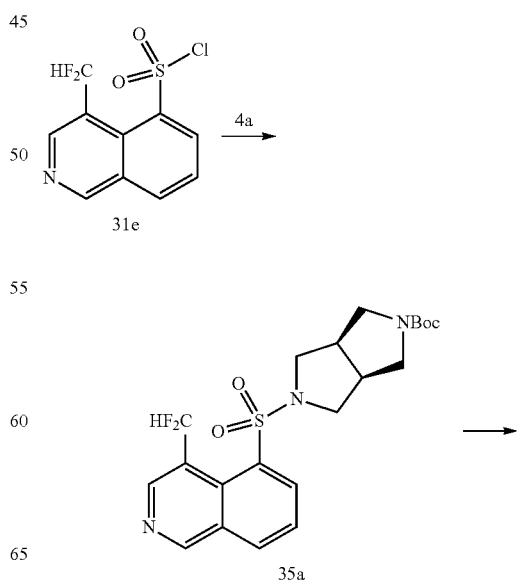

-continued

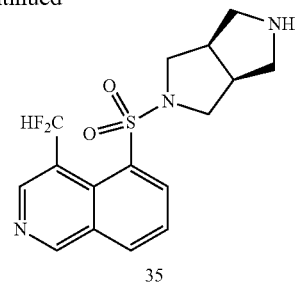

35

-continued

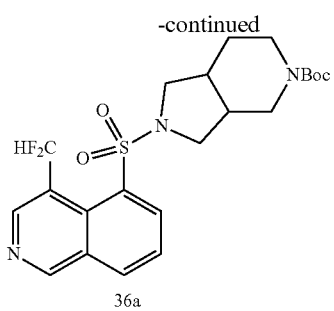

36a

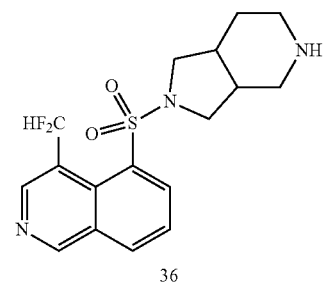

36

Step 1

From cis-tert-butyl hexahydropyrrolo[3,4-c]pyrrole-2(1H)-carboxylate 7a (37 mg, 0.24 mmol, example 7) and 4-(difluoromethyl)isoquinoline-5-sulfonyl chloride 31e (68 mg, 0.24 mmol, example 31), the compound tert-butyl 5-((4-(difluoromethyl)isoquinolin-5-yl)sulfonyl) hexahydropyrrolo[3,4-c]pyrrole-2(1H)-carboxylate 35a was made following the procedure described in example 1. (52 mg, yellow solid, yield: 48%).

MS-ESI calc'd. [M+H]$^+$ 454, found 454.

Step 2

The compound 4-(difluoromethyl)-5-((hexahydropyrrolo[3,4-c]pyrrol-2(1H)-yl)sulfonyl) isoquinoline 35 was made from tert-butyl 5-((4-(difluoromethyl)isoquinolin-5-yl)sulfonyl) hexahydropyrrolo[3,4-c]pyrrole-2(1H)-carboxylate 35a (52 mg, 0.11 mmol) following the procedure described in example 1. (25 mg, white solid, 51%).

$^1$H NMR (400 MHz, D$_2$O): δ 9.59 (s, 1H), 9.05 (s, 1H), 8.66-8.54 (m, 2H), 8.24-7.91 (m, 2H), 4.56-4.46 (m, 4H), 3.35-3.31 (m, 2H), 3.20-3.15 (m, 2H), 3.00-2.90 (m, 2H).

MS-ESI calc'd. [M+H]$^+$ 354, found 354.

Example 36

4-(difluoromethyl)-5-((hexahydro-1H-pyrrolo[3,4-c]pyridin-2(3H)-yl)sulfonyl)isoquinoline

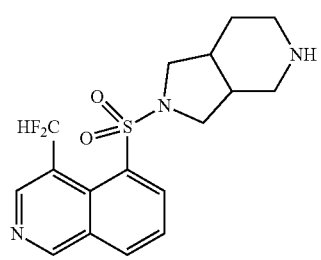

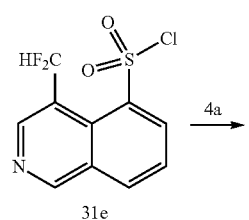

31e

Step 1

From tert-butyl hexahydro-1H-pyrrolo[3,4-c]pyridine-5(6H)-carboxylate 8 h (56 mg, 0.25 mmol, example 8) and 4-(difluoromethyl)isoquinoline-5-sulfonyl chloride 31e (75 mg, 0.27 mmol, example 31), the compound tert-butyl 2-((4-(difluoromethyl)isoquinolin-5-yl)sulfonyl) hexahydro-1H-pyrrolo[3,4-c]pyridine-5(6H)-carboxylate 36a was made following the procedure described in example 1. (45 mg, light yellow oil, yield: 45%).

MS-ESI calc'd. [M+H]$^+$ 490, found 490.

Step 2

The compound 4-(difluoromethyl)-5-((hexahydro-1H-pyrrolo[3,4-c]pyridine-2(3H)-yl)sulfonyl)isoquinoline 36 was made from tert-butyl 2-((4-(difluoromethyl)isoquinolin-5-yl)sulfonyl) hexahydro-1H-pyrrolo[3,4-c]pyridine-5(6H)-carboxylate 36a (45 mg, 0.096 mmol) following the procedure described in example 1. (30 mg, white solid, yield: 86%).

$^1$H NMR (400 MHz, CD$_3$OD): δ 9.78 (s, 1H), 9.18 (s, 1H), 8.76-8.73 (m, 1H), 8.71-8.66 (m, 1H), 8.39 (t, J=5 4.0 Hz, 1H), 8.08 (t, J=8.0 Hz, 1H), 3.66-3.59 (m, 2H), 3.55-3.48 (m, 2H), 3.43-3.36 (m, 1H), 3.27-3.23 (m, 1H), 3.24-3.14 (m, 2H), 2.88-2.70 (m, 2H), 2.13-2.02 (m, 1H), 1.97-1.85 (m, 1H).

MS-ESI calc'd. [M+H]$^+$ 368, found 368.

Example 37

5-((hexahydropyrrolo[3,2-b]pyrrol-1(2H)-yl)sulfonyl)-4-methylisoquinoline

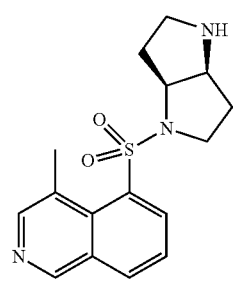 [SMILES: Cc1cncc2cccc(S(=O)(=O)N3CC[C@@H]4NCC[C@@H]43)c12]

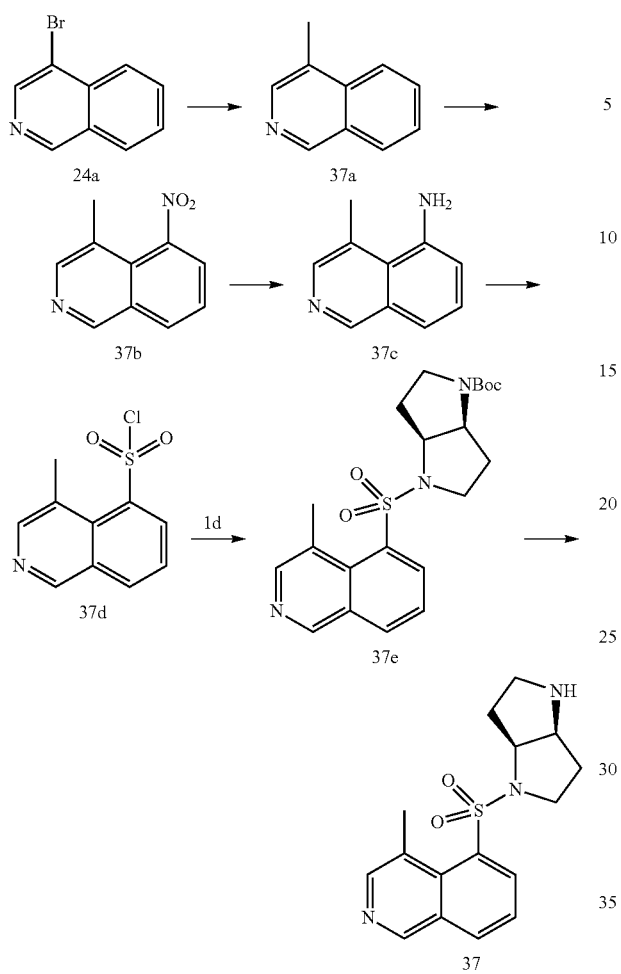

mg, 3.16 mmol) following the procedure described in example 16. (300 mg, green solid, yield: 40%).

¹H NMR (400 MHz, DMSO-d6): δ 9.78 (brs., 1H), 8.89-8.90 (m, 1H), 8.55-8.50 (m, 2H), 8.01-7.88 (m, 1H), 3.34 (s, 3H).

Step 5

From cis-tert-butyl hexahydropyrrolo[3,2-b]pyrrole-1(2H)-carboxylate 1d (33 mg, 0.14 mmol) and 4-methylisoquinoline-5-sulfonyl chloride 37d (68 mg, 0.28 mmol), the compound tert-butyl 4-((4-methylisoquinolin-5-yl)sulfonyl)hexahydropyrrolo[3,2-b]pyrrole-1(2H)-carboxylate 37e was made following the procedure described in example 1. (15 mg, yellow oil, yield: 25%).

MS-ESI calc'd. [M+H]⁺ 418, found 418.

Step 6

The compound 5-((hexahydropyrrolo[3,2-b]pyrrol-1(2H)-yl)sulfonyl)-4-methyl isoquinoline 37 was made from tert-butyl 4-((4-methylisoquinolin-5-yl)sulfonyl)hexahydropyrrolo[3,2-b]pyrrole-1(2H)-carboxylate 37e (15 mg, 0.036 mmol) following the procedure described in example 1. (10 mg, yellow solid, yield: 67%).

¹H NMR (400 MHz, D₂O): δ9.58 (s, 1H), 8.64-8.62 (m, 1H), 8.51-8.50 (m, 2H), 8.02 (t, J=8.0, 1H), 4.85-4.81 (m, 2H), 4.62-4.59 (m, 1H), 3.79-3.73 (m, 1H), 3.66-3.60 (m, 1H), 3.48-3.40 (m, 2H), 3.06 (s, 3H), 2.64-2.54 (m, 1H), 2.34-2.25 (m, 2H).

MS-ESI calc'd. [M+H]⁺ 318, found 318.

Example 38

5-((hexahydropyrrolo[3,4-d]pyrrol-5 (1H)-yl)sulfonyl)-4-methylisoquinoline

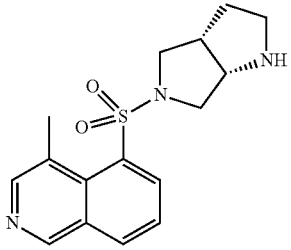 [SMILES: Cc1cncc2cccc(S(=O)(=O)N3C[C@@H]4CCN[C@@H]4C3)c12]

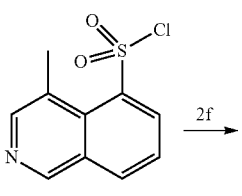

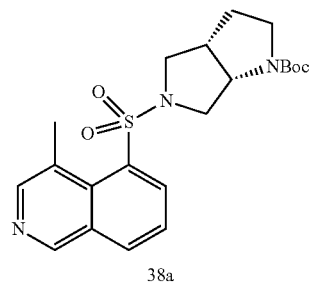

Step 1

To a solution of 4-bromoisoquinoline 24a (15.0 g, 72.5 mmol), methylboronic acid (8.8 g, 146 mmol) and K₃PO₄ (62.0 g, 292 mmol) in 350 mL toluene was added Pd₂(dba)₃ (6.6 g, 7.2 mmol) and Dicyclohexyl (2',6'-dimethoxy-[1,1'-biphenyls]-2-base) phosphine (5.9 g, 14.3 mmol) under N₂ atmosphere. The resulting mixture was heated under reflux for 20 h, then was cooled down to room temperature and quenched by pouring into 300 mL water. The aqueous mixture was extracted with EtOAc (100 mL×2), the combined organic layers were dried over anhydrous Na₂SO₄ and concentrated. The crude product was purified by silica gel column chromatography (0-100 EtOAc/PE) to give 4-methylisoquinoline 37a (10.7 g, yellow oil, yield: 94%).

Step 2

The compound 4-methyl-5-nitroisoquinoline 37b was made from 4-methylisoquinoline 37a (10.0 g, 69.9 mmol) following the procedure described in example 16. (10 g, yellow oil, yield: 76%).

Step 3

The compound 4-methylisoquinolin-5-amine 37c was made from 4-methyl-5-nitroisoquinoline 37b (9.00 g, 47.8 mmol) following the procedure described in example 16. (6.0 g, yellow solid, yield: 71%).

Step 4

The compound 4-methylisoquinoline-5-sulfonyl chloride 37d was made from 4-methylisoquinolin-5-amine 37c (500

-continued

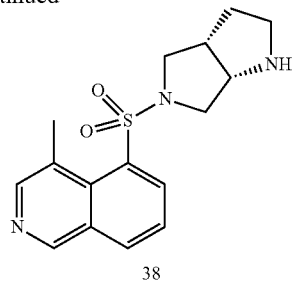

38

Step 1
From cis-tert-butyl hexahydropyrrolo[3,4-b]pyrrole-1(2H)-carboxylate 2f (50 mg, 0.24 mmol, example 2) and 4-methylisoquinoline-5-sulfonyl chloride 37d (85 mg, 0.35 mmol), the compound tert-butyl 54(4-methylisoquinolin-5-yl)sulfonyl)hexahydropyrrolo[3,4-b]pyrrole-1 (2H)-carboxylate 38a was made following the procedure described in example 1. (40 mg, colorless oil, yield: 40%).

Step 2
The compound 5-((hexahydropyrrolo[3,4-b]pyrrol-5(1H)-yl)sulfonyl)-4-methyl isoquinoline 38 was made from tert-butyl 5-((4-methylisoquinolin-5-yl)sulfonyl)hexahydropyrrolo[3,4-b]pyrrole-1 (2H)-carboxylate 38a (40 mg, 0.095 mmol) following the procedure described in example 1. (28 mg, white solid, yield: 75%).

$^1$H NMR (400 MHz, D$_2$O): δ 9.52 (s, 1H), 8.66-8.42 (m, 3H), 7.96 (t, J=7.8 Hz, 1H), 4.46 (brs., 1H), 3.94-3.80 (m, 2H), 3.75-3.70 (m, 1H), 3.55-3.50 (m, 1H), 3.45-3.26 (m, 3H), 3.01 (brs, 3H), 2.35-2.22 (m, 1H), 2.00-1.95 (m, 1H).

Example 39

5-((hexahydropyrrolo[3,4-b]pyrrol-5(1H)-yl)sulfonyl)-4-methylisoquinolin-1-ol

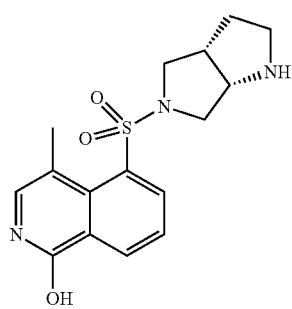

39

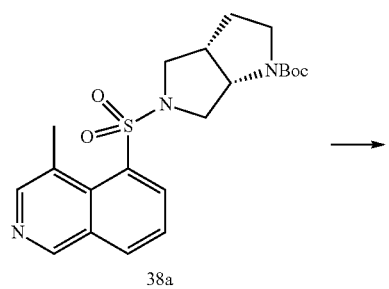

38a

-continued

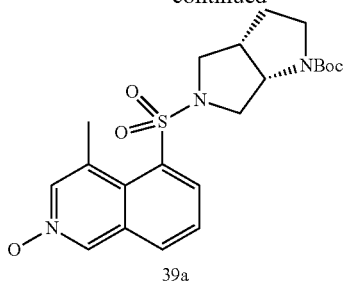

39a

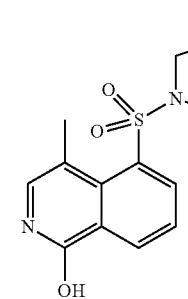

39b

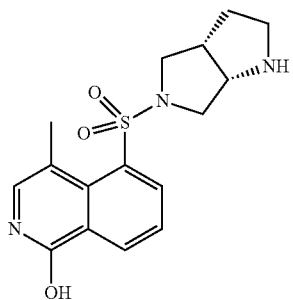 [SMILES: Cc1cnc(O)c2cccc(S(=O)(=O)N3C[C@@H]4CCN[C@@H]4C3)c12]

39

Step 1
To a solution of tert-butyl 5-((4-methylisoquinolin-5-yl)sulfonyl) hexahydropyrrolo[3,4-b]pyrrole-1(2H)-carboxylate 38a (100 mg, 0.24 mmol) in 5 mL dichloromethane was added m-CPBA (83 mg, 0.48 mmol) at 0° C. and the mixture was stirred for 2 h at room temperature. The reaction mixture was concentrated directly and purified by silica gel column chromatography (0-100% EtOAc/PE) to give 5-((1-(tert-butoxycarbonyl)hexahydropyrrolo[3,4-b]pyrrol-5(1H)-yl)sulfonyl)-4-methylisoquinoline 2-oxide 39a (75 mg, yellow oil, yield: 73%).

Step 2
A solution of 5-((1-(tert-butoxycarbonyl) hexahydropyrrolo[3,4-b]pyrrol-5(1H)-yl) sulfonyl)-4-methylisoquinoline 2-oxide 39a (75 mg, 0.17 mmol) in 1 mL acetic anhydride was stirred at 100° C. for 2 h. The reaction mixture was concentrated under reduced pressure to remove the solvent. To the residue was added 6 mL THF and Na$_2$CO$_3$ (37 mg, 0.35 mmol) in 2 mL water, and the resulting mixture was stirred at room temperature for 30 min, and then was extracted with dichloromethane (20 mL×3). The combined organic layers were dried over anhydrous Na$_2$SO$_4$, concentrated and purified by silica gel column chromatography (0-100% EtOAc/PE) to give tert-butyl 5-((1-hydroxy-4-methylisoquinolin-5-yl)sulfonyl)hexahydropyrrolo[3,4-b]pyrrole-1(2H)-carboxylate 39b (35 mg, yellow oil, yield: 47%).

Step 3

The compound 5-((hexahydropyrrolo[3,4-b]pyrrol-5(1H)-yl)sulfonyl)-4-methyl isoquinolin-1-ol 39 was made from tert-butyl 5-((1-hydroxy-4-methylisoquinolin-5-yl)sulfonyl)hexahydropyrrolo[3,4-b]pyrrole-1(2H)-carboxylate 39b (35 mg, 0.081 mmol) following the procedure described in example 1. (13 mg, white solid, yield: 48%).

$^1$H NMR (400 MHz, D$_2$O): δ8.57 (d, J=7.2 Hz, 1H), 8.14 (d, J=7.2 Hz, 1H), 7.62-7.57 (m, 1H), 7.19 (brs, 1H), 3.76 (brs, 2H), 3.44 (brs, 2H), 3.40-3.30 (m, 3H), 2.52 (s, 3H), 2.27 (brs, 1H), 1.96 (brs, 2H).

Example 40

5-((hexahydro-1H-pyrrolo[3,4-b]pyridin-6(2H)-yl)sulfonyl)-4-methylisoquinoline

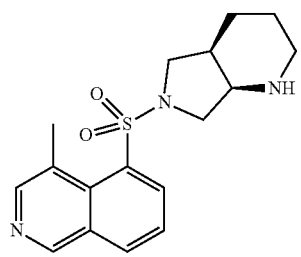 [SMILES: Cc1cncc2cccc(S(=O)(=O)N3C[C@H]4CCCN[C@H]4C3)c12]

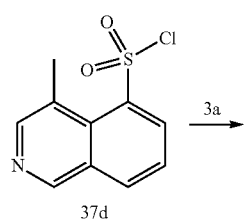

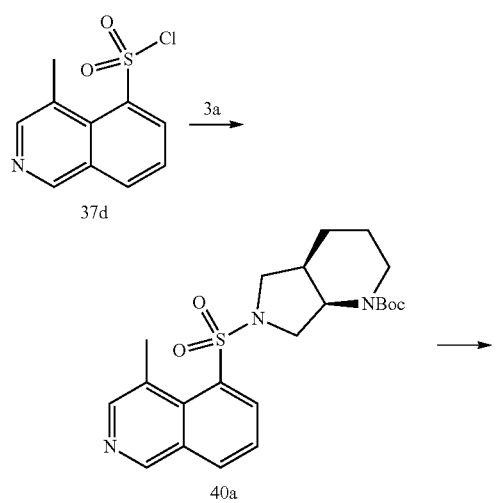

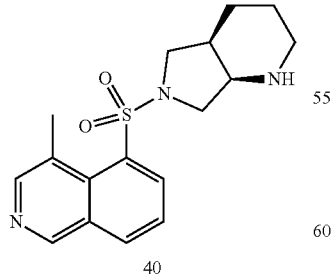

Step 1

From cis-tert-butyl octahydro-1H-pyrrolo[3,4-b]pyridine-1-carboxylate 3a (50 mg, 0.22 mmol, example 3) and 4-methylisoquinoline-5-sulfonyl chloride 37d (106 mg, 0.44 mmol), the compound tert-butyl 6-((4-methylisoquinolin-5-yl)sulfonyl)octahydro-1H-pyrrolo[3,4-b]pyridine-1-carboxylate 40a was made following the procedure described in example 1. (30 mg, yellow oil, yield: 31%).

MS-ESI calc'd. [M+H]$^+$ 432, found 432.

Step 2

The compound 5-((hexahydro-1H-pyrrolo[3,4-b]pyridin-6(2H)-yl)sulfonyl)-4-methyl isoquinoline 40 was made from tert-butyl 6-((4-methylisoquinolin-5-yl)sulfonyl)octahydro-1H-pyrrolo[3,4-b]pyridine-1-carboxylate 40a (30 mg, 0.074 mmol) following the procedure described in example 1. (20 mg, white solid, yield: 87%).

$^1$H NMR (400 MHz, CDCl$_3$): δ 9.55 (s, 1H), 8.62 (d, J=8.0 Hz, 1H), 8.52-8.44 (m, 2H), 8.00 (t, J=8.0 Hz, 1H), 4.06 (s, 1H), 3.97-3.91 (m, 1H), 3.89-3.84 (m, 1H), 3.80-3.75 (m, 1H), 3.65-3.60 (m, 1H), 3.40-3.35 (m, 1H), 3.10 (s, 1H), 3.07 (s, 3H), 2.04-1.73 (m, 5H).

MS-ESI calc'd. [M+H]$^+$ 332, found 332.

Example 41

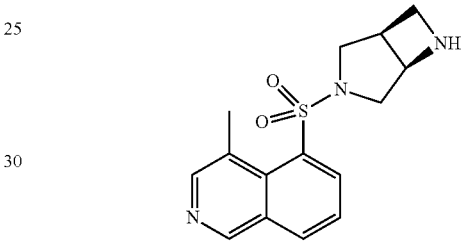

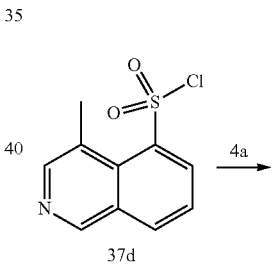

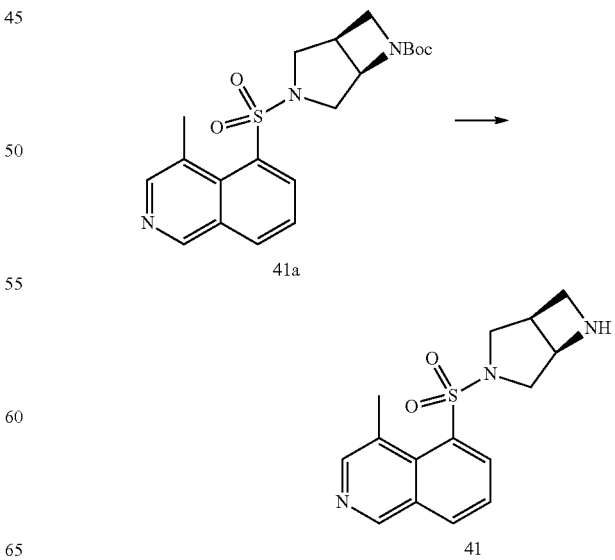

Step 1

From tert-butyl 3,6-diazabicyclo[3.2.0]heptane-6-carboxylate 4a (30 mg, 0.15 mmol, example 4) and 4-methylisoquinoline-5-sulfonyl chloride 37d (73 mg, 0.31 mmol, example 37), the compound tert-butyl 3((4-methylisoquinolin-5-yl)sulfonyl)-3,6-diazabicyclo[3.2.0]heptane-6-carboxylate 41a was made following the procedure described in example 1. (45 mg, yellow oil, yield: 74%).

MS-ESI calc'd. [M+H]$^+$ 404, found 404.

Step 2

The compound 5-(3,6-diazabicyclo[3.2.0]heptan-3-ylsulfonyl)-4-methylisoquinoline 41 was made from tert-butyl 3((4-methylisoquinolin-5-yl)sulfonyl)-3,6-diazabicyclo[3.2.0]heptane-6-carboxylate 41a (45 mg, 0.11 mmol) following the procedure described in example 1. (25 mg, yellow solid, yield: 74%).

$^1$H NMR (400 MHz, D$_2$O): δ9.49 (s, 1H), 8.57-8.55 (m, 1H), 8.47-8.46 (m, 2H), 7.94 (t, J=8.0 Hz, 1H), 4.24-4.16 (m, 3H), 3.90 (d, J=8.0 Hz, 1H), 3.82-3.78 (m, 1H), 3.73-3.68 (m, 1H), 3.53 (d, J=8.0 Hz, 2H), 3.06 (s, 3H).

MS-ESI calc'd. [M+H]$^+$ 304, found 304.

Example 42

4-methyl-5-((octahydro-1H-pyrrolo[3,2-b]pyridin-1-yl)sulfonyl)isoquinoline

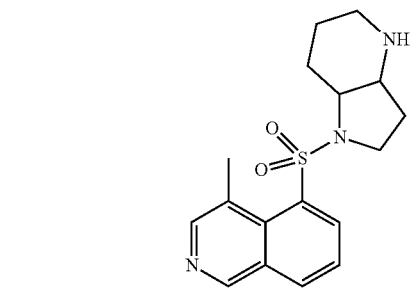 [SMILES: Cc1cncc2cccc(S(=O)(=O)N3CCC4NCCCC43)c12]

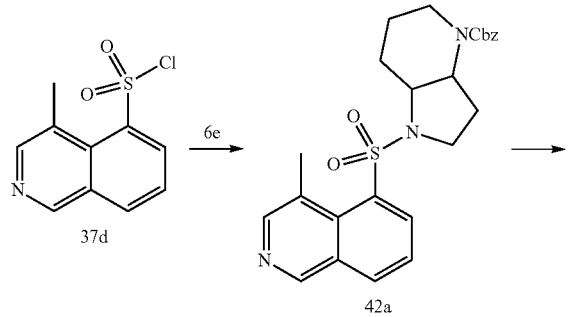

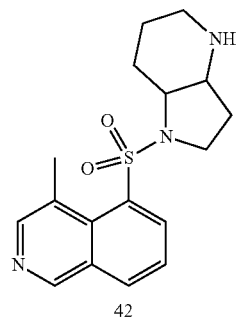

Step 1

From benzyl hexahydro-1H-pyrrolo[3,2-b]pyridine-4(2H)-carboxylate 6e (30 mg, 0.12 mmol, example 6) and 4-methylisoquinoline-5-sulfonyl chloride 37d (139 mg, 0.58 mmol, example 37), the compound benzyl 1-((4-methylisoquinolin-5-yl)sulfonyl)hexahydro-1H-pyrrolo[3,2-b]pyridine-4(2H)-carboxylate 42a was made following the procedure described in example 1. (30 mg, yellow oil, yield: 56%).

MS-ESI calc'd. [M+H]$^+$ 466, found 466.

Step 2

The compound 4-methyl-5-((octahydro-1H-pyrrolo[3,2-b]pyridin-1-yl)sulfonyl) isoquinoline 42 was made from benzyl 1-((4-methylisoquinolin-5-yl)sulfonyl)hexahydro-1H-pyrrolo[3,2-b]pyridine-4(2H)-carboxylate 42a (30 mg, 0.065 mmol) following the procedure described for the synthesis of 6-(isoquinolin-5-ylsulfonyl)decahydro-1,6-naphthyridine 5 in example 5. (5 mg, yellow solid, yield: 23%).

$^1$H NMR (400 MHz, D$_2$O): δ8.98 (s, 1H), 8.30 (s, 1H), 8.24-8.21 (m, 2H), 7.64 (t, J=8.0, 1H), 4.16-4.11 (m, 1H), 4.06-4.03 (m, 1H), 3.70-3.65 (m, 2H), 3.15-3.03 (m, 2H), 2.78 (s, 3H), 2.40-2.34 (m, 2H), 1.80-1.72 (m, 3H), 1.52-1.50 (m, 1H).

MS-ESI calc'd. [M+H]$^+$ 332, found 332.

Example 43

5-((hexahydropyrrolo[3,4-c]pyrrol-2(1H)-yl)sulfonyl)-4-methylisoquinoline

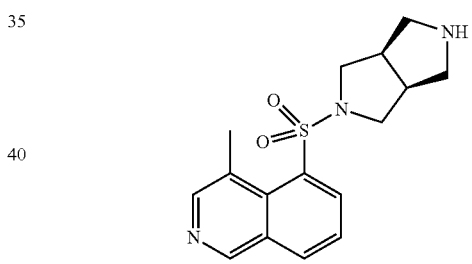

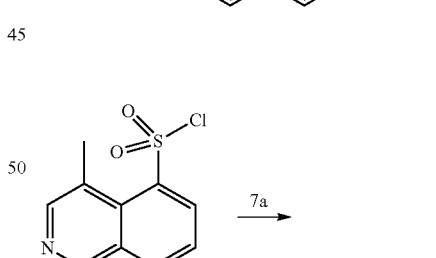

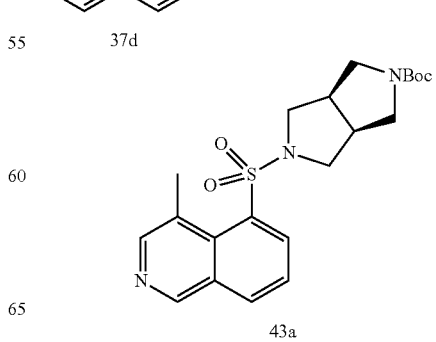

91

-continued

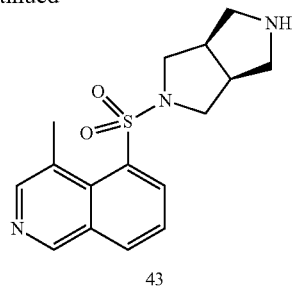

43

Step 1

From cis-tert-butyl hexahydropyrrolo[3,4-c]pyrrole-2(1H)-carboxylate 7a (30 mg, 0.14 mmol, example 7) and 4-methylisoquinoline-5-sulfonyl chloride 37d (68 mg, 0.28 mmol, example 37), the compound tert-butyl 5-((4-methyl-isoquinolin-5-yl)sulfonyl)hexahydropyrrolo[3,4-c]pyrrole-2(1H)-carboxylate 43a was made following the procedure described in example 1. (28 mg, yellow oil, yield: 48%).

MS-ESI calc'd. [M+H]$^+$ 418, found 418.

Step 2

The compound 5-((hexahydropyrrolo[3,4-c]pyrrol-2(1H)-yl)sulfonyl)-4-methyl isoquinoline 43 was made from tert-butyl 5-((4-methylisoquinolin-5-yl)sulfonyl)hexahydro-pyrrolo[3,4-c]pyrrole-2(1H)-carboxylate 43a (28 mg, 0.067 mmol) following the procedure described in example 1. (8 mg, white solid, yield: 34%).

$^1$H NMR (400 MHz, D$_2$O): δ 8.99 (brs, 1H), 8.39-8.28 (m, 2H), 8.21 (m, 1H), 7.64 (t, J=8.0 Hz, 1H), 3.68-3.59 (m, 4H), 3.49-3.47 (m, 2H), 3.30-3.23 (m, 2H), 3.12-3.04 (m, 2H), 2.84-2.76 (brs, 3H).

MS-ESI calc'd. [M+H]$^+$ 318, found 318.

Example 44

5-((hexahydro-1H-pyrrolo[3,4-c]pyridin-2(3H)-yl)sulfonyl)-4-methylisoquinoline

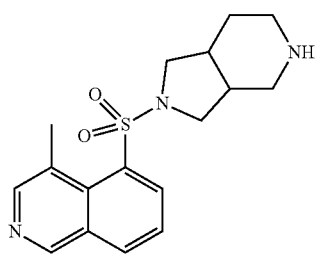 [SMILES: Cc1cncc2cccc(S(=O)(=O)N3CC4CCNCC4C3)c12]

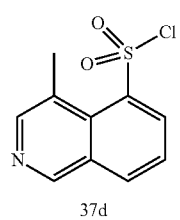

37d

8h →

92

-continued

44a

→

44

Step 1

From tert-butyl hexahydro-1H-pyrrolo[3,4-c]pyridine-5(6H)-carboxylate 8 h (30 mg, 0.13 mmol, example 8) and 4-methylisoquinoline-5-sulfonyl chloride 37d (48 mg, 0.2 mmol, example 37), the compound tert-butyl 2-((4-methyl-isoquinolin-5-yl)sulfonyl)hexahydro-1H-pyrrolo[3,4-c]pyridine-5(6H)-carboxylate 44a was made following the procedure described in example 1. (40 mg, colorless oil, yield: 70%).

Step 2

The compound 5-((hexahydro-1H-pyrrolo[3,4-c]pyridin-2(3H)-yl)sulfonyl)-4-methyl isoquinoline 44 was made from tert-butyl 2-((4-methylisoquinolin-5-yl)sulfonyl)hexahydro-1H-pyrrolo[3,4-c]pyridine-5(6H)-carboxylate 44a (40 mg, 0.47 mmol) following the procedure described in example 1. (15 mg, white solid, yield: 40%).

$^1$H NMR (400 MHz, D$_2$O): δ 9.50 (s, 1H), 8.58 (d, J=8.0 Hz, 1H), 8.52-8.44 (m, 2H), 7.96 (t, J=8.0 Hz, 1H) 3.70-3.65 (m, 2H), 3.57-3.48 (m, 2H), 3.40-3.35 (m, 1H), 3.26-3.10 (m, 3H), 3.03 (s, 3H), 2.89-2.73 (m, 2H), 2.08-1.97 (m, 1H), 1.89-1.77 (m, 1H).

Example 45

6-((4-methylisoquinolin-5-yl)sulfonyl)decahydro-1,6-naphthyridine

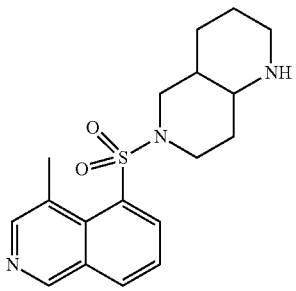 [SMILES: Cc1cncc2cccc(S(=O)(=O)N3CCC4NCCCC4C3)c12]

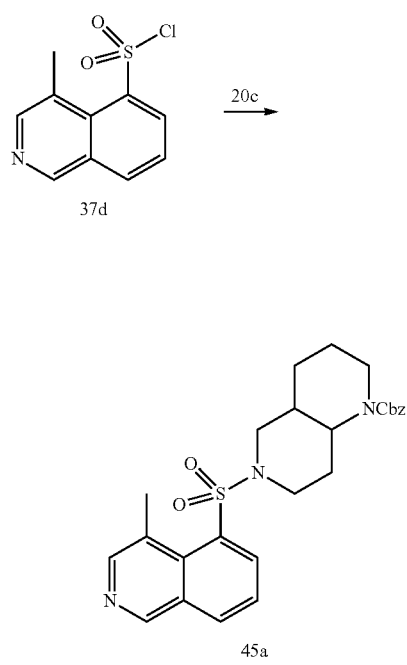

Example 46

5-((hexahydropyrrolo[3,4-b]pyrrol-5 (1H)-yl)sulfonyl)-4-(trifluoromethyl)isoquinoline

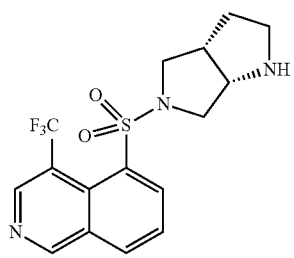 [SMILES: O=S(=O)(c1cccc2cncc(C(F)(F)F)c12)N1C[C@@H]2CCN[C@@H]2C1]

Step 1

From benzyl octahydro-1,6-naphthyridine-1(2H)-carboxylate 20c (30 mg, 0.11 mmol, example 20) and 4-methylisoquinoline-5-sulfonyl chloride 37d (40 mg, 0.16 mmol, example 37), the compound benzyl 6-((4-methylisoquinolin-5-yl)sulfonyl)octahydro-1,6-naphthyridine-1(2H)-carboxylate 45a was made following the procedure described in example 1. (40 mg, colorless oil, yield: 76%).

Step 2

The compound 6-((4-methylisoquinolin-5-yl)sulfonyl)decahydro-1,6-naphthyridine 45 was made from benzyl 6-((4-methylisoquinolin-5-yl)sulfonyl)octahydro-1,6-naphthyridine-1(2H)-carboxylate 45a (40 mg, 0.084 mmol) following the procedure described for the synthesis of 6-(isoquinolin-5-ylsulfonyl)decahydro-1,6-naphthyridine 5 in example 5. (12 mg, white solid, yield: 41%).

$^1$H NMR (400 MHz, D$_2$O): δ 9.03 (brs, 1H), 8.36-8.30 (m, 2H), 8.21 (brs, 1H), 7.65 (brs, 1H), 3.98-3.74 (m, 2H), 3.60-3.55 (m, 1H), 3.45-3.40 (m, 1H), 3.34-2.88 (m, 4H), 2.80 (brs, 3H), 2.35-2.02 (m, 2H), 1.96-1.70 (m, 4H), 1.59 (brs, 1H).

Step 1

The compound 4-bromo-5-nitroisoquinoline 46a was made from 4-bromoisoquinoline 24a (10 g, 48.3 mmol) following the procedure described for the synthesis of 4-fluoro-5-nitroisoquinoline 24c in example 24. (8.5 g, yellow solid, yield: 85%). It was used in the next step directly.

Step 2

To a solution of 4-bromo-5-nitroisoquinoline 46a (1.00 g, 3.95 mmol) in 40 mL 1-methyl pyrrolidone was added Potassium fluoride (459 mg, 7.90 mmol), Trimethyl(trifluoromethyl)silane (2.80 g, 19.7 mmol) and cuprous iodide (1.13 g, 5.93 mmol) under $N_2$ atmosphere. The resulting mixture was stirred at 100° C. for 8 h, cooled down to room temperature, diluted with 300 mL EtOAc, and filtered to remove solid impurity. The filtrate was washed with 20 mL water and 20 mL brine in sequence, dried over anhydrous $Na_2SO_4$, and filtered. The filtrate was concentrated under reduced pressure to give a crude product which was purified by silica gel column chromatography (30% EtOAc/PE) to give 5-nitro-4-(trifluoromethyl)isoquinoline 46b (500 mg, yellow solid, yield: 52%).

$^1$H NMR (400 MHz, DMSO-d6): δ9.82 (s, 1H), 9.20 (s, 1H), 8.71 (d, J=7.2 Hz, 1H), 8.57 (d, J=7.2 Hz, 1H), 8.05-8.01 (m, 1H).

MS-ESI calc'd. [M+H]$^+$ 243, found 243.

Step 3

The compound 4-(trifluoromethyl)isoquinolin-5-amine 46c was made from 5-nitro-4-(trifluoromethyl)isoquinoline 46b (1.00 g, 4.15 mmol) following the procedure described for the synthesis of 4-(difluoromethyl)isoquinolin-5-amine 31d in example 31. (523 mg, yellow solid, yield: 59%).

$^1$H NMR (400 MHz, DMSO): δ 9.41 (s, 1H), 8.76 (s, 1H), 7.61-7.55 (m, 2H), 7.10-7.05 (m, 1H), 5.45 (s, 2H).

MS-ESI calc'd. [M+H]$^+$ 213, found 213.

Step 4

The compound 4-(trifluoromethyl)isoquinoline-5-sulfonyl chloride 46d was made from 4-(trifluoromethyl)isoquinolin-5-amine 46c (300 mg, 1.41 mmol) following the procedure described for the synthesis of 4-chloroisoquinoline-5-sulfonyl chloride 16d in example 16. (74 mg, light yellow solid, yield: 18%).

$^1$H NMR (400 MHz, DMSO-d6): δ 9.53 (s, 1H), 8.89 (s, 1H), 8.60 (d, J=8.0 Hz, 1H), 8.27 (d, J=8.0 Hz, 1H), 7.81-7.77 (m, 1H).

Step 5

From cis-tert-butyl hexahydropyrrolo[3,4-b]pyrrole-1(2H)-carboxylate 2f (32 mg, 0.15 mmol, example 2) and 4-(trifluoromethyl)isoquinoline-5-sulfonyl chloride 46d (45 mg, 0.15 mmol), the compound tert-butyl 5-((4-(trifluoromethyl)isoquinolin-5-yl)sulfonyl) hexahydropyrrolo[3,4-b]pyrrole-1(2H)-carboxylate 46e was made following the procedure described in example 1. (30 mg, yellow solid, yield: 42%).

MS-ESI calc'd. [M+H]$^+$ 472, found 472.

Step 6

The compound 5-((hexahydropyrrolo[3,4-b]pyrrol-5(1H)-yl)sulfonyl)-4-(trifluoromethyl) isoquinoline 46 was made from tert-butyl 5-((4-(trifluoromethyl)isoquinolin-5-yl)sulfonyl) hexahydropyrrolo[3,4-b]pyrrole-1(2H)-carboxylate 46e (30 mg, 0.063 mmol) following the procedure described in example 1. (14 mg, white solid, yield: 60%).

$^1$H NMR (400 MHz, CD$_3$OD): δ 9.62 (s, 1H), 9.04 (s, 1H), 8.58-8.55 (m, 2H), 8.0-7.98 (m, 1H), 4.35-4.30 (m, 1H), 3.75-3.70 (m, 1H), 3.46-3.35 (m, 3H), 3.27-3.12 (m, 3H), 2.28-2.23 (m, 1H), 1.99-1.93 (m, 1H).

MS-ESI calc'd. [M+H]$^+$ 372, found 372.

Example 47

5-((hexahydropyrrolo[3,2-b]pyrrol-1(2H)-yl)sulfonyl)-4-methoxyisoquinoline

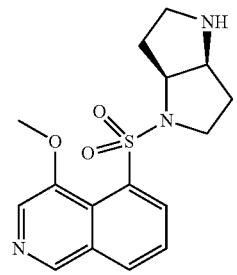 [SMILES: COc1cncc2cccc(S(=O)(=O)N3CC[C@@H]4NCC[C@@H]43)c12]

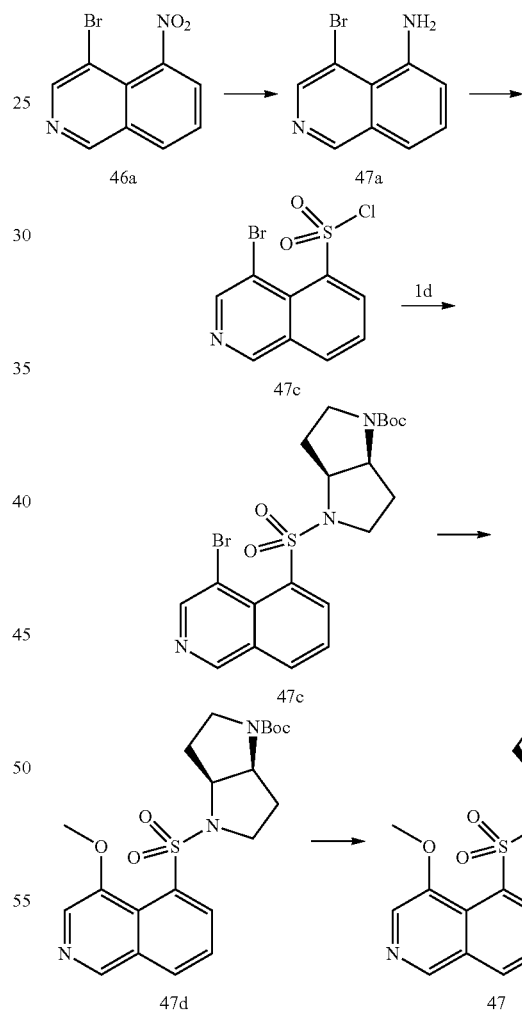

Step 1

The compound 4-bromoisoquinolin-5-amine 47a was made from 4-bromo-5-nitroisoquinoline 46a (3.00 g, 11.8 mmol, example 46) following the procedure described for the synthesis of 4-chloroisoquinolin-5-amine 16c in example 16. (1.9 g, light yellow solid, yield: 73%).

$^1$H NMR (400 MHz, DMSO): δ 9.03 (s, 1H), 8.42 (s, 1H), 7.46-7.42 (m, 1H), 7.36 (d, J=7.2 Hz, 1H), 7.06 (d, J=7.2 Hz, 1H), 6.17 (s, 2H).

Step 2

The compound 4-bromoisoquinoline-5-sulfonyl chloride 47b was made from 4-bromoisoquinolin-5-amine 47a (1.90 g, 8.52 mmol) following the procedure described for the synthesis of 4-chloroisoquinoline-5-sulfonyl chloride 16d in example 16. (500 mg, light yellow solid, yield: 20%).

$^1$H NMR (400 MHz, DMSO): δ 9.57 (s, 1H), 8.91 (s, 1H), 8.40 (d, J=7.2 Hz, 1H), 8.39 (d, J=7.2 Hz, 1H), 7.86-7.82 (m, 1H).

Step 3

From cis-tert-butyl hexahydropyrrolo[3,2-b]pyrrole-1 (2H)-carboxylate 1d (40 mg, 0.19 mmol) and 4-bromoisoquinoline-5-sulfonyl chloride 47b (57 mg, 0.19 mmol), the compound tert-butyl 4-((4-bromoisoquinolin-5-yl)sulfonyl) hexahydropyrrolo[3,2-b]pyrrole-1(2H)-carboxylate 47c was made following the procedure described in example 1. (62 mg, yellow solid, yield: 68%).

$^1$H NMR (400 MHz, CDCl$_3$): δ 9.23 (s, 1H), 9.02 (s, 1H), 8.37 (d, J=7.2 Hz, 1H), 8.22 (d, J=7.2 Hz, 1H), 7.73-7.69 (m, 1H), 4.67-4.47 (m, 2H), 3.81-3.63 (m, 2H), 3.50-3.37 (m, 3H), 2.39-2.21 (m, 2H), 2.05-1.93 (m, 1H), 1.45 (s, 9H).

MS-ESI calc'd. [M+H]$^+$ 482, found 482.

Step 4

To a solution of tert-butyl 4-((4-bromoisoquinolin-5-yl) sulfonyl)hexahydropyrrolo[3,2-b]pyrrole-1(2H)-carboxylate 47c (62 mg, 0.13 mmol) in 1 mL anhydrous MeOH was added pyridine (0.2 mg, 0.003 mmol), NaOMe (300 mg, 1.28 mmol) and CuI (12 mg, 0.064 mmol) under N$_2$ atmosphere. The resulting mixture was stirred at 100° C. for 3 h, cooled down to room temperature, diluted with 30 mL EtOAc, and filtered to removed solid impurities. The filtrate was washed with saturated aq. NH$_4$Cl 20 mL water 20 mL and 20 mL brine in sequence, dried over anhydrous Na$_2$SO$_4$, and filtered. The filtrate was concentrated under reduced pressure and purified by prep. TLC (100% EtOAc) to give tert-butyl 4-((4-methoxyisoquinolin-5-yl)sulfonyl)hexahydropyrrolo[3,2-b]pyrrole-1(2H)-carboxylate 47d (33 mg, white solid, yield: 60%).

MS-ESI calc'd. [M+H]$^+$ 434, found 434.

Step 5

The compound 5-((hexahydropyrrolo[3,2-b]pyrrol-1 (2H)-yl)sulfonyl)-4-methoxy isoquinoline 47 was made from tert-butyl 4-((4-methoxyisoquinolin-5-yl)sulfonyl) hexahydropyrrolo[3,2-b]pyrrole-1(2H)-carboxylate 47d (33 mg, 0.063 mmol) following the procedure described in example 1. (26 mg, white solid, yield: 83%).

$^1$H NMR (400 MHz, D$_2$O): δ 9.31 (s, 1H), 8.61 (d, J=7.6 Hz, 1H), 8.50 (d, J=7.6 Hz, 1H), 8.34 (s, 1H), 8.05-8.01 (m, 1H), 4.81-4.75 (m, 1H), 4.58-4.57 (m, 1H), 4.16 (s, 3H), 3.80-3.70 (m, 1H), 3.67-3.64 (m, 1H), 3.41-3.38 (m, 2H), 2.53-2.50 (m, 1H), 2.35-2.34 (m, 1H), 2.25-2.21 (m, 2H).

MS-ESI calc'd. [M+H]$^+$ 334, found 334.

Example 48

5-((hexahydropyrrolo[3,4-b]pyrrol-5 (1H)-yl)sulfonyl)-4-methoxyisoquinoline

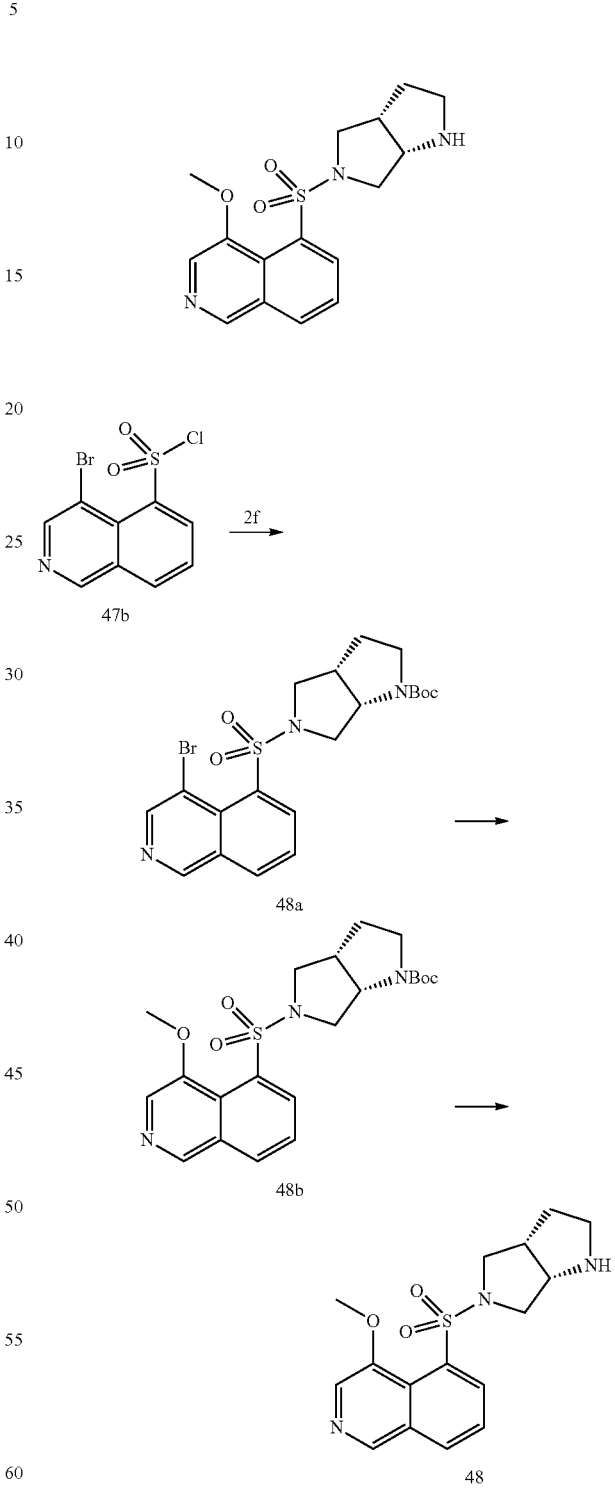

Step 1

From cis-tert-butyl hexahydropyrrolo[3,4-b]pyrrole-1 (2H)-carboxylate 2f (76 mg, 0.36 mmol, example 2) and 4-bromoisoquinoline-5-sulfonyl chloride 47b (94 mg, 0.30 mmol, example 47), the compound tert-butyl 5-((4-bromoisoquinolin-5-yl)sulfonyl)hexahydropyrrolo[3,4-b]pyrrole-1(2H)-carboxylate 48a was made following the procedure described in example 1. (120 mg, white solid, yield: 81%).

Step 2

The compound tert-butyl 5-((4-methoxyisoquinolin-5-yl)sulfonyl)hexahydropyrrolo[3,4-b]pyrrole-1(2H)-carboxylate 48b was made from tert-butyl 5((4-bromoisoquinolin-5-yl)sulfonyl)hexahydropyrrolo[3,4-b]pyrrole-1(2H)-carboxylate 48a (120 mg, 0.250 mmol) following the procedure described in example 47. (86 mg, white solid, yield: 80%).

MS-ESI calc'd. [M+H]⁺ 434, found 434.

Step 3

The compound 5-((hexahydropyrrolo[3,4-b]pyrrol-5(1H)-yl)sulfonyl)-4-methoxy isoquinoline 48 was made from tert-butyl 5-((4-methoxyisoquinolin-5-yl)sulfonyl)hexahydropyrrolo[3,4-b]pyrrole-1(2H)-carboxylate 48b (86 mg, 0.2 mmol) following the procedure described in example 1. (25 mg, white solid, yield: 38%).

¹H NMR (400 MHz, D₂O): δ 9.28 (s, 1H), 8.56-8.53 (m, 2H), 8.28 (s, 1H), 8.00-7.96 (m, 1H), 4.39-4.36 (m, 1H), 4.10 (s, 3H), 3.84-3.81 (m, 1H), 3.75-3.74 (m, 1H), 3.62-3.60 (m, 1H), 3.55-3.54 (m, 1H), 3.31-3.27 (m, 3H), 2.28-2.22 (m, 1H), 1.95-1.92 (m, 1H).

MS-ESI calc'd. [M+H]⁺ 334, found 334.

Example 49

5-((hexahydro-1H-pyrrolo[3,4-b]pyridin-6(2H)-yl)sulfonyl)-4-methoxyisoquinoline

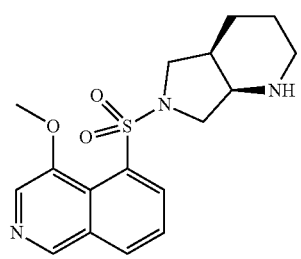 [SMILES: COc1cncc2cccc(S(=O)(=O)N3C[C@H]4CCCN[C@H]4C3)c12]

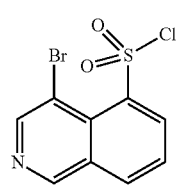

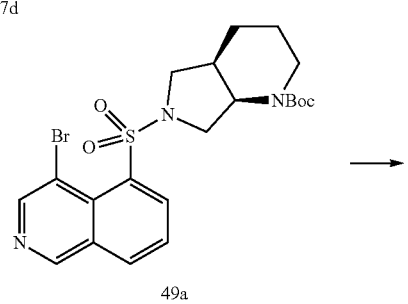

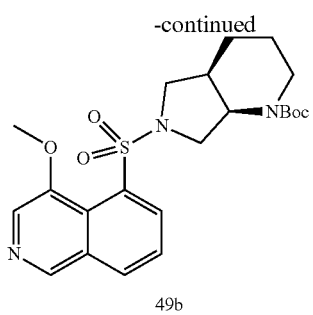

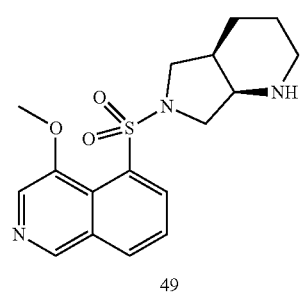

Step 1

From cis-tert-butyl octahydro-1H-pyrrolo[3,4-b]pyridine-1-carboxylate 3a (40 mg, 0.18 mmol) and 4-bromoisoquinoline-5-sulfonyl chloride 47b (54 mg, 0.18 mmol, example 47), the compound tert-butyl 6-((4-bromoisoquinolin-5-yl)sulfonyl)octahydro-1H-pyrrolo[3,4-b]pyridine-1-carboxylate 49a was made following the procedure described in example 1. (80 mg, white solid, yield: 91%).

¹H NMR (400 MHz, CDCl3): δ 9.21 (s, 1H), 8.99 (s, 1H), 8.34-8.32 (m, 1H), 8.20-8.18 (m, 1H), 7.72-7.68 (m, 1H), 4.01-3.98 (m, 1H), 3.56-3.51 (m, 2H), 3.48-3.41 (m, 2H), 2.80-2.75 (m, 1H), 2.28-2.24 (m, 1H), 1.83-1.77 (m, 2H), 1.60-1.57 (m, 3H), 1.43 (s, 9H).

MS-ESI calc'd. [M+H]⁺ 496, found 496.

Step 2

The compound tert-butyl 6-((4-methoxyisoquinolin-5-yl)sulfonyl)octahydro-1H-pyrrolo[3,4-b]pyridine-1-carboxylate 49b was made from tert-butyl 6-((4-bromoisoquinolin-5-yl)sulfonyl)octahydro-1H-pyrrolo[3,4-b]pyridine-1-carboxylate 49a (80 mg, 0.16 mmol) following the procedure described in example 47. (46 mg, white solid, yield: 64%).

MS-ESI calc'd. [M+H]⁺ 448, found 448.

Step 3

The compound 5-((hexahydro-1H-pyrrolo[3,4-b]pyridin-6(2H)-yl)sulfonyl)-4-methoxy isoquinoline 49 was made from tert-butyl 6-((4-methoxyisoquinolin-5-yl)sulfonyl)octahydro-1H-pyrrolo[3,4-b]pyridine-1-carboxylate 49b (46 mg, 0.1 mmol) following the procedure described in example 1. (20 mg, white solid, yield: 56%).

¹H NMR: (400 MHz, D₂O): δ9.21 (s, 1H), 8.51-8.50 (m, 1H), 8.36-8.34 (m, 1H), 8.29 (s, 1H), 7.95-7.91 (m, 1H), 4.08 (s, 3H), 3.96-3.94 (m, 1H), 3.83-3.79 (m, 2H), 3.67-3.65 (m, 1H), 3.54-3.49 (m, 1H), 3.31-3.28 (m, 1H), 3.01-2.93 (m, 2H), 1.90-1.65 (m, 4H).

MS-ESI calc'd. [M+H]⁺ 348, found 348.

Example 50

5-(3,6-diazabicyclo[3.2.0]heptan-3-ylsulfonyl)-4-methoxyisoquinoline

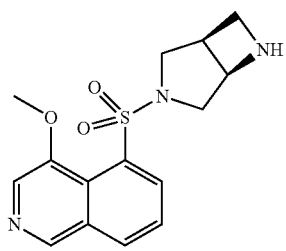 [SMILES: COc1cncc2cccc(S(=O)(=O)N3C[C@H]4CN[C@H]4C3)c12]

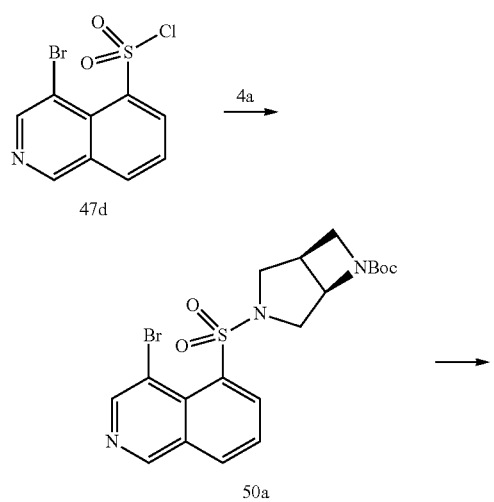

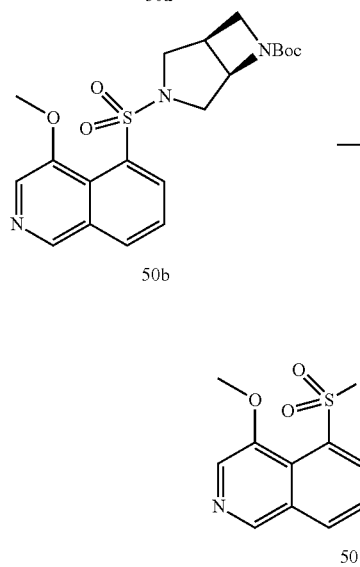

Step 1

From tert-butyl 3,6-diazabicyclo[3.2.0]heptane-6-carboxylate 4a (40 mg, 0.12 mmol, example 4) and 4-bromoisoquinoline-5-sulfonyl chloride 47b (57 mg, 0.19 mmol, example 47), the compound tert-butyl 3-((4-bromoisoquinolin-5-yl)sulfonyl)-3,6-diazabicyclo[3.2.0]heptane-6-carboxylate 50a was made following the procedure described in example 1. (82 mg, yellow solid, yield: 87%).

$^1$H NMR (400 MHz, CDCl$_3$): δ 9.22 (s, 1H), 9.02 (s, 1H), 8.69 (d, J=7.6 Hz, 1H), 8.23 (d, J=7.6 Hz, 1H), 7.73-7.69 (m, 1H), 4.78-4.76 (m, 1H), 4.10-3.92 (m, 2H), 3.75-3.56 (m, 2H), 3.44-3.12 (m, 3H), 1.39 (s, 9H).

MS-ESI calc'd. [M+H]$^+$ 468, found 468.

Step 2

The compound tert-butyl 3-((4-methoxyisoquinolin-5-yl)sulfonyl)-3,6-diazabicyclo[3.2.0]heptane-6-carboxylate 50b was made from tert-butyl 3((4-bromoisoquinolin-5-yl)sulfonyl)-3,6-diazabicyclo[3.2.0]heptane-6-carboxylate 50a (82 mg, 0.18 mmol) following the procedure described in example 47. (30 mg, white solid, yield: 42%).

MS-ESI calc'd. [M+H]$^+$ 420, found 420.

Step 3

The compound 5-(3,6-diazabicyclo[3.2.0]heptan-3-ylsulfonyl)-4-methoxyisoquinoline 50 was made from tert-butyl 3-((4-methoxyisoquinolin-5-yl)sulfonyl)-3,6-diazabicyclo[3.2.0]heptane-6-carboxylate 50b (30 mg, 0.071 mmol) following the procedure described in example 1. (20 mg, white solid, yield: 86%).

$^1$H NMR (400 MHz, D$_2$O): δ 9.32 (s, 1H), 8.62-8.57 (m, 2H), 8.33 (s, 1H), 8.03-7.99 (m, 1H), 5.01 (t, J=6.0 Hz, 1H), 4.28-4.23 (m, 1H), 4.17 (s, 3H), 4.11 (d, J=13.6 Hz, 1H), 3.96 (d, J=13.6 Hz, 1H), 3.84-3.79 (m, 1H), 3.62-3.52 (m, 2H), 3.46-3.42 (m, 1H).

MS-ESI calc'd. [M+H]$^+$ 320, found 320.

Example 51

4-methoxy-5-((octahydro-1H-pyrrolo[3,2-b]pyridin-1-yl)sulfonyl)isoquinoline

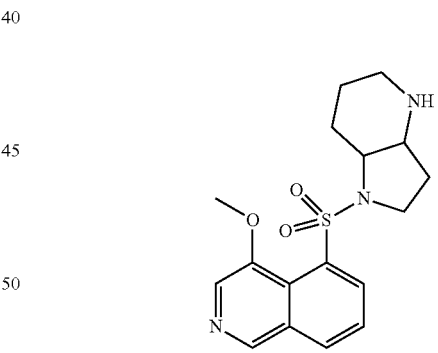

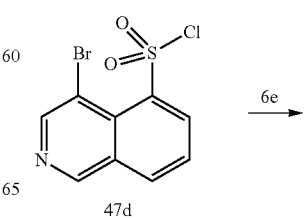

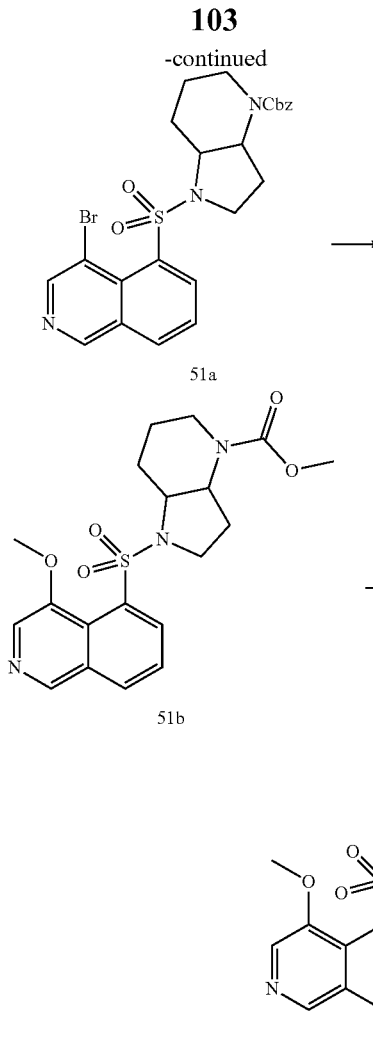

Step 1

From benzyl hexahydro-1H-pyrrolo[3,2-b]pyridine-4 (2H)-carboxylate 6e (50 mg, 19 mmol, example 6) and 4-bromoisoquinoline-5-sulfonyl chloride 47b (59 mg, 0.19 mmol, example 47), the compound benzyl 1-((4-bromoisoquinolin-5-yl)sulfonyl)hexahydro-1H-pyrrolo[3,2-b]pyridine-4(2H)-carboxylate 51a was made following the procedure described in example 1. (90 mg, white solid, yield: 88%).

¹H NMR (400 MHz, CDCl₃): δ 9.21 (s, 1H), 8.99 (s, 1H), 8.20-8.18 (m, 2H), 7.77-7.70 (m, 1H), 7.38 (brs, 5H), 5.18 (s, 2H), 4.07-4.05 (m, 1H), 3.89-3.86 (m, 1H), 3.68-3.63 (m, 3H), 3.45-3.43 (m, 1H), 2.87-2.84 (m, 1H), 2.24-2.16 (m, 3H), 1.69-1.65 (m, 1H), 1.40-1.34 (m, 1H).

MS-ESI calc'd. [M+H]⁺ 530, found 530.

Step 2

The compound methyl 1-((4-methoxyisoquinolin-5-yl)sulfonyl)hexahydro-1H-pyrrolo[3,2-b]pyridine-4(2H)-carboxylate 51b was made from benzyl 1-((4-bromoisoquinolin-5-yl)sulfonyl)hexahydro-1H-pyrrolo[3,2-b]pyridine-4(2H)-carboxylate 51a (90 mg, 0.17 mmol) following the procedure described in example 47. (30 mg, white solid, yield: 44%).

MS-ESI calc'd. [M+H]⁺ 406, found 406.

Step 3

To a solution of methyl 1-((4-methoxyisoquinolin-5-yl)sulfonyl)hexahydro-1H-pyrrolo[3,2-b]pyridine-4(2H)-carboxylate 51b (30 mg, 0.074 mmol) and NaOMe (40 mg, 0.74 mmol) in 2 mL MeOH was added 0.1 mL 25% aq. NaOH. The resulting mixture was microwave heated at 90° C. for 2 h under N₂ atmosphere, cooled down to room temperature when the reaction finished and diluted with 50 mL EtOAc. The resulting mixture was washed with 50 mL brine, the organic layer was dried over anhydrous Na₂SO₄. The filtrate was concentrated under reduced pressure and purified by prep. TLC (50% MeOH/EtOAc) to give 4-methoxy-5-((octahydro-1H-pyrrolo[3,2-b]pyridin-1-yl)sulfonyl)isoquinoline 51 (20 mg, white solid, yield: 78%).

¹H NMR (400 MHz, CD₃OD): δ 9.01 (s, 1H), 8.51-8.49 (m, 1H), 8.40-8.38 (s, 1H), 8.36 (s, 1H), 7.86-7.82 (m, 1H), 4.15 (s, 3H), 4.14-4.12 (m, 1H), 3.93-3.92 (m, 1H), 3.80-3.76 (m, 2H), 3.13-3.11 (m, 1H), 3.02-3.00 (m, 1H), 2.34-2.28 (m, 2H), 1.99-1.89 (m, 2H), 1.65-1.54 (m, 2H).

MS-ESI calc'd. [M+H]⁺ 348, found 348.

Example 52

5-((hexahydropyrrolo[3,4-c]pyrrol-2(1H)-yl)sulfonyl)-4-methoxyisoquinoline

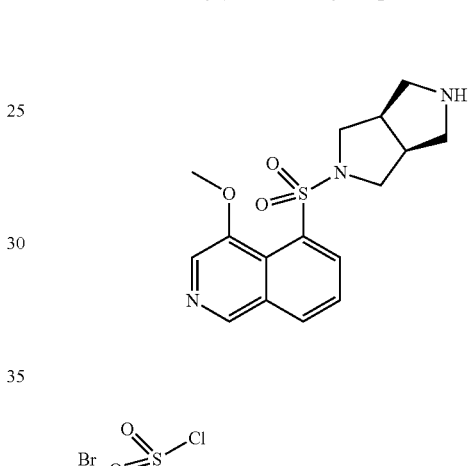

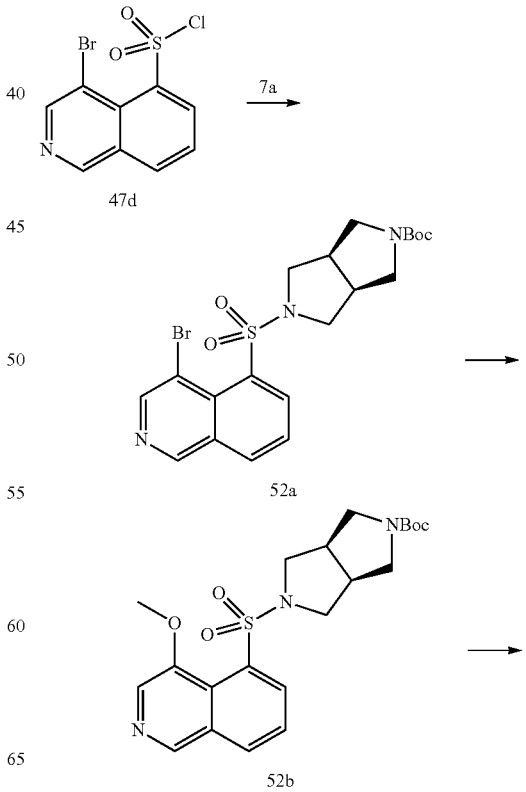

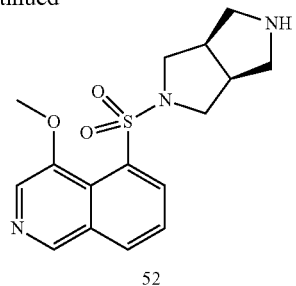

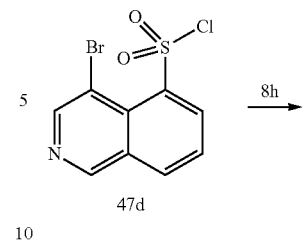

Step 1

From cis-tert-butyl hexahydropyrrolo[3,4-c]pyrrole-2(1H)-carboxylate 7a (40 mg, 0.19 mmol, example 7) and 4-bromoisoquinoline-5-sulfonyl chloride 47b (58 mg, 0.19 mmol, example 47), the compound tert-butyl 5-((4-bromoisoquinolin-5-yl)sulfonyl)hexahydropyrrolo[3,4-c]pyrrole-2(1H)-carboxylate 52a was made following the procedure described in example 1. (80 mg, white solid, yield: 88%).

$^1$H NMR (400 MHz, CDCl$_3$): δ 9.21 (s, 1H), 9.00 (s, 1H), 8.43-8.41 (m, 1H), 8.22-8.20 (m, 1H), 7.73-7.69 (m, 1H), 3.76-3.72 (m, 2H), 3.38-3.34 (m, 4H), 3.08-3.03 (m, 4H), 1.61 (s, 9H).

MS-ESI calc'd. [M+H]$^+$ 482, found 482.

Step 2

The compound tert-butyl 5-((4-methoxyisoquinolin-5-yl)sulfonyl)hexahydropyrrolo[3,4-c]pyrrole-2(1H)-carboxylate 52b was made from tert-butyl 5-((4-bromoisoquinolin-5-yl)sulfonyl)hexahydropyrrolo[3,4-c]pyrrole-2(1H)-carboxylate 52a (80 mg, 0.17 mmol) following the procedure described in example 47. (45 mg, white solid, yield: 63%).

MS-ESI calc'd. [M+H]$^+$ 434, found 434.

Step 3

The compound 5-((hexahydropyrrolo[3,4-c]pyrrol-2(1H)-yl)sulfonyl)-4-methoxy isoquinoline 52 was made from tert-butyl 5-((4-methoxyisoquinolin-5-yl)sulfonyl)hexahydropyrrolo[3,4-c]pyrrole-2(1H)-carboxylate 52b (45 mg, 0.1 mmol) following the procedure described in example 1. (20 mg, white solid, yield: 58%).

$^1$H NMR (400 MHz, D$_2$O): δ 9.22 (s, 1H), 8.53-8.49 (m, 2H), 8.28 (s, 1H), 7.97-7.93 (m, 1H), 4.10 (s, 3H), 3.64-3.60 (m, 4H), 3.56-3.53 (m, 2H), 3.24-3.22 (m, 2H), 3.08-3.05 (m, 2H).

MS-ESI calc'd. [M+H]$^+$ 334, found 334.

Example 53

5-((hexahydro-1H-pyrrolo[3,4-c]pyridin-2(3H)-yl)sulfonyl)-4-methoxyisoquinoline

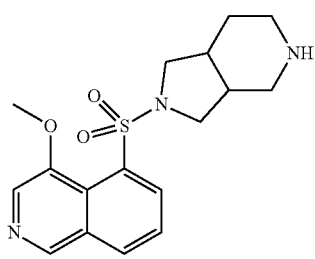 [SMILES: COc1cncc2cccc(S(=O)(=O)N3CC4CCNCC4C3)c12]

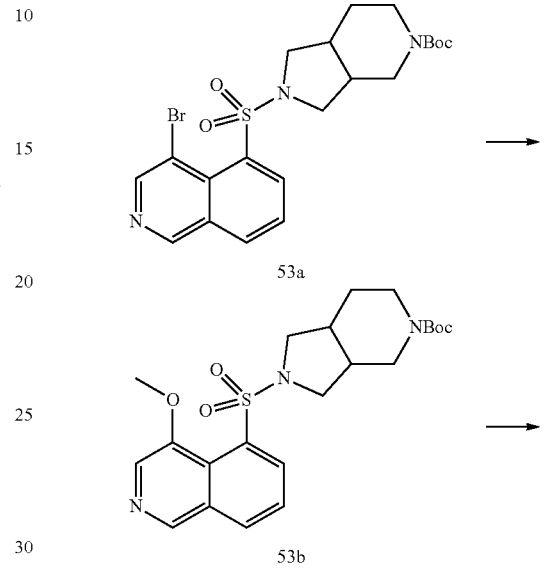

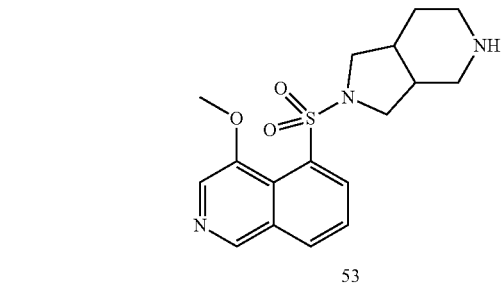

Step 1

From tert-butyl hexahydro-1H-pyrrolo[3,4-c]pyridine-5(6H)-carboxylate 8 h (40 mg, 0.17 mmol, example 8) and 4-bromoisoquinoline-5-sulfonyl chloride 47b (54 mg, 0.17 mmol, example 47), the compound tert-butyl 2-((4-bromoisoquinolin-5-yl)sulfonyl)hexahydro-1H-pyrrolo[3,4-c]pyridine-5(6H)-carboxylate 53a was made following the procedure described in example 1. (40 mg, yellow solid, yield: 46%).

MS-ESI calc'd. [M+H]$^+$ 496, found 496.

Step 2

The compound tert-butyl 2-((4-methoxyisoquinolin-5-yl)sulfonyl)hexahydro-1H-pyrrolo[3,4-c]pyridine-5(6H)-carboxylate 53b was made from tert-butyl 2-((4-bromoisoquinolin-5-yl)sulfonyl)hexahydro-1H-pyrrolo[3,4-c]pyridine-5(6H)-carboxylate 53a (40 mg, 0.081 mmol) following the procedure described in example 47. (20 mg, white solid, yield: 55%).

MS-ESI calc'd. [M+H]$^+$ 448, found 448.

Step 3

The compound 5-((hexahydro-1H-pyrrolo[3,4-c]pyridin-2(3H)-yl)sulfonyl)-4-methoxyisoquinoline 53 was made from tert-butyl 2-((4-methoxyisoquinolin-5-yl)sulfonyl)hexahydro-1H-pyrrolo[3,4-c]pyridine-5(6H)-carboxylate 53b (20 mg, 0.044 mmol) following the procedure described in example 1. (14 mg, white solid, yield: 77%).

¹H NMR (400 MHz, D₂O): δ 9.26 (s, 1H), 8.57 (d, J=7.2 Hz, 1H), 8.46 (d, J=7.2 Hz, 1H), 8.33 (s, 1H), 8.01-7.97 (m, 1H), 4.15 (s, 3H), 3.72-3.66 (m, 2H), 3.59-3.53 (m, 2H), 3.42-3.37 (m, 1H), 3.25-3.14 (m, 3H), 2.87-2.77 (m, 2H), 2.10-2.02 (m, 1H), 1.88-1.82 (m, 1H).

MS-ESI calc'd. [M+H]⁺ 348, found 348.

Example 54

6-((4-methoxyisoquinolin-5-yl)sulfonyl)decahydro-1,6-naphthyridine

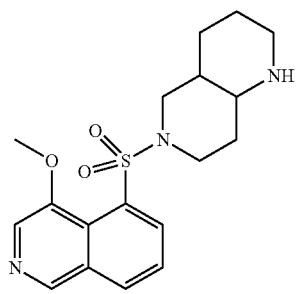 [SMILES: COc1cncc2cccc(S(=O)(=O)N3CCC4NCCCC4C3)c12]

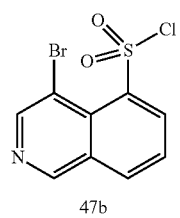

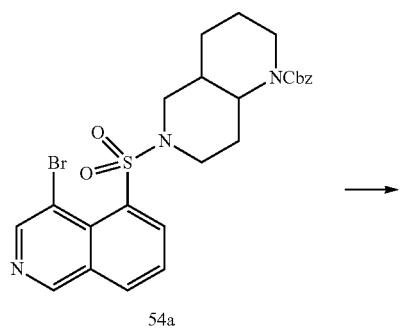

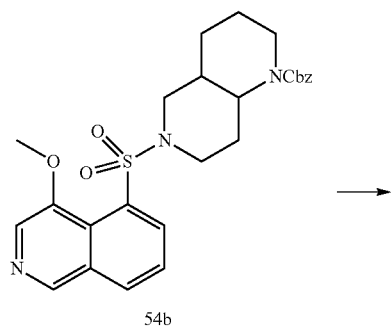

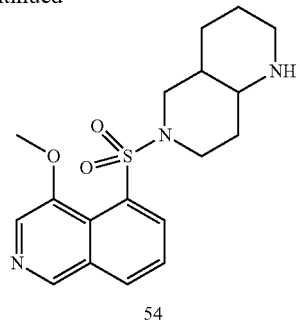

54

Step 1

From benzyl octahydro-1,6-naphthyridine-1(2H)-carboxylate 20c (50 mg, 0.16 mmol, example 20) and 4-bromoisoquinoline-5-sulfonyl chloride 47b (49 mg, 0.16 mmol, example 47), the compound benzyl 6-((4-bromoisoquinolin-5-yl)sulfonyl)octahydro-1,6-naphthyridine-1(2H)-carboxylate 54a was made following the procedure described in example 1. (46 mg, yellow solid, yield: 53%).

¹H NMR (400 MHz, CDCl₃): δ 9.22 (s, 1H), 9.01 (s, 1H), 8.34-8.12 (m, 2H), 7.72-7.68 (m, 1H), 7.37-7.32 (m, 5H), 5.15 (s, 2H), 4.12-3.84 (m, 2H), 3.71-3.49 (m, 2H), 3.26-2.67 (m, 2H), 2.05-1.67 (m, 4H), 1.54-1.45 (m, 4H).

MS-ESI calc'd. [M+H]⁺ 544, found 544.

Step 2

The compound benzyl 6-((4-methoxyisoquinolin-5-yl)sulfonyl)octahydro-1,6-naphthyridine-1(2H)-carboxylate 55b was made from benzyl 6-((4-bromoisoquinolin-5-yl)sulfonyl)octahydro-1,6-naphthyridine-1(2H)-carboxylate 54a (46 mg, 0.084 mmol) following the procedure described in example 47. (20 mg, white solid, yield: 47%).

MS-ESI calc'd. [M+H]⁺ 496, found 496.

Step 3

The compound 6-((4-methoxyisoquinolin-5-yl)sulfonyl)decahydro-1,6-naphthyridine 55 was made from benzyl 6-((4-methoxyisoquinolin-5-yl)sulfonyl)octahydro-1,6-naphthyridine-1(2H)-carboxylate 55b (20 mg, 0.04 mmol) following the procedure described in example 5. (3 mg, white solid, yield: 21%).

¹H NMR (400 MHz, CD₃OD): δ 8.97 (s, 1H), 8.39-8.33 (m, 2H), 8.31 (s, 1H), 7.80-7.76 (m, 1H), 4.11 (s, 3H), 3.95-3.56 (m, 2H), 3.41-3.35 (m, 1H), 3.20-3.03 (m, 2H), 2.83-2.49 (m, 2H), 1.98-1.84 (m, 1H), 1.80-1.48 (m, 6H).

MS-ESI calc'd. [M+H]⁺ 362, found 362.

Example 55

3-(isoquinolin-5-ylsulfonyl)-3-azabicyclo[3.2.0]heptan-1-amine

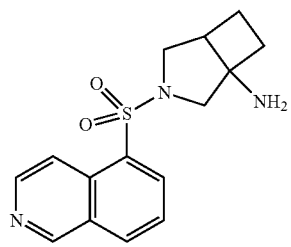 [SMILES: NC12CCC1CN(S(=O)(=O)c1cccc3cnccc13)C2]

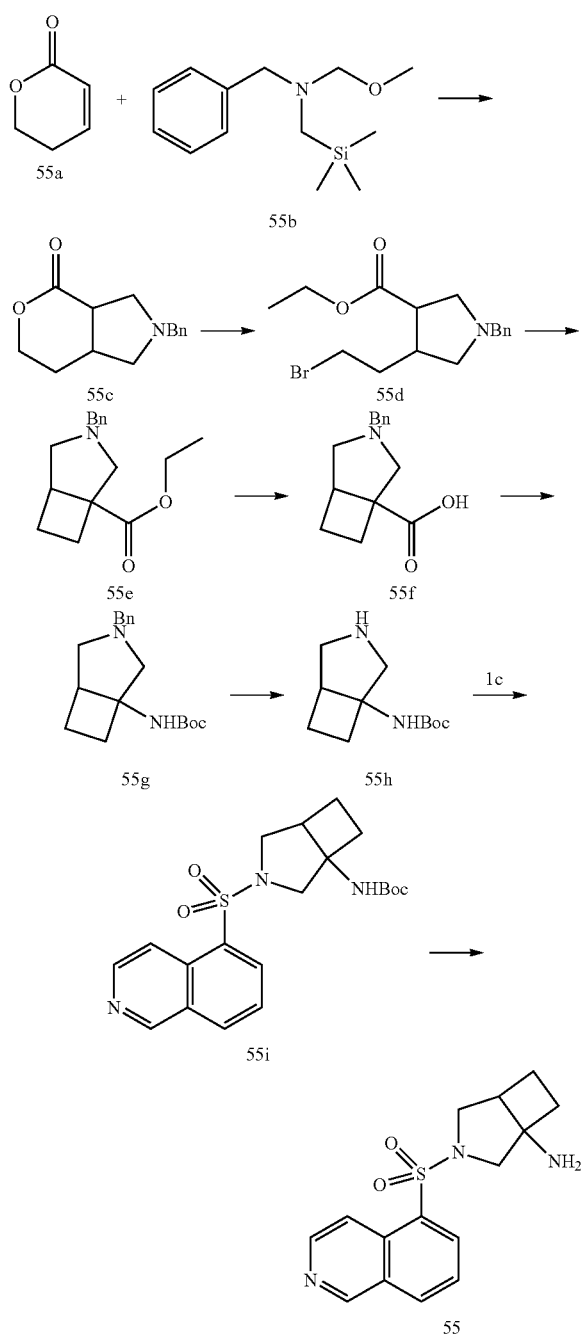

Step 1

To a solution of 5,6-dihydro-2H-pyran-2-one 55a (300 mg, 3.06 mmol) and N-benzyl-1-methoxy-N-((trimethylsilyl)methyl)methanamine 55b (1.09 g, 4.59 mmol) in 15 mL dichloromethane was added TFA (520 mg, 4.59 mmol, in 0.6 mL DICHLOROMETHANE) at −78° C. under $N_2$ atmosphere. The resulting mixture was warmed to 25° C. and stirred for 4 h, diluted with 50 mL dichloromethane, washed with saturated aq. $K_2CO_3$ (50 mL×2) and brine (50 mL×1) successively. The organic layer was dried over anhydrous $Na_2SO_4$, filtered, and concentrated under reduced pressure. The crude was purified by prep. TLC (50% EtOAc/PE) to give 2-benzylhexahydropyrano[3,4-c]pyrrol-4(2H)-one 55c (533 mg, colorless oil, yield: 75%).

$^1$H NMR (400 MHz, $CDCl_3$): δ 7.26-7.18 (m, 5H), 4.34-4.33 (m, 2H), 4.18-4.15 (m, 1H), 3.57-3.46 (m, 2H), 2.89-2.85 (m, 2H), 2.77-2.73 (m, 1H), 2.71-2.61 (m, 1H), 2.23-2.19 (m, 1H), 1.94-1.93 (m, 1H), 1.60-1.59 (m, 1H).

MS-ESI calc'd. [M+H]$^+$ 232, found 232.

Step 2

To a solution of 2-benzylhexahydropyrano[3,4-c]pyrrol-4(2H)-one 55c (9 g, 38.9 mmol) in 100 mL EtOH was bubbled freshly prepared HBr (g) at 0° C. The resulting mixture was stirred at this temperature for 3 h, warmed to 25° C. and stirred continuously for 24 h. The reaction mixture was concentrated directly to give a crude product which was recrystallized in EtOH to give ethyl 1-benzyl-4-(2-bromoethyl)pyrrolidine-3-carboxylate 55d (9.0 g, white solid, yield: 85%).

$^1$H NMR (400 MHz, $CDCl_3$): δ 7.69-7.67 (m, 2H), 7.42-7.41 (m, 3H), 4.41-4.37 (m, 2H), 4.26-4.19 (m, 2H), 3.93-3.88 (m, 1H), 3.72-3.62 (m, 1H), 3.42-3.39 (m, 2H), 3.33-3.29 (m, 2H), 3.05-2.95 (m, 1H), 2.82-2.79 (m, 1H), 1.92-1.87 (m, 2H), 1.33-1.27 (m, 3H).

MS-ESI calc'd. [M+H]$^+$ 340, found 340.

Step 3

To a solution of 1-benzyl-4-(2-bromoethyl)pyrrolidine-3-carboxylate 55d (1.00 g, 2.94 mmol) in 100 mL anhydrous THF was added Lithium Hexamethyldisilazide (17.6 mL, 17.6 mmol, 1.0 M in THF) dropwisely at −78° C. under $N_2$ atmosphere. The resulting mixture was stirred at 20° C. for 18 h, then was diluted with 100 mL EtOAc. The mixture was washed with saturated aq. $NH_4Cl$ (100 mL×3) and brine (100 mL×1) in sequence, dried over anhydrous $Na_2SO_4$ and filtered. The filtrate was concentrated under reduced pressure and purified by prep. TLC (50% EtOAc/PE) to give ethyl 3-benzyl-3-azabicyclo[3.2.0]heptane-1-carboxylate 55e (130 mg, white solid, yield: 17%).

$^1$H NMR (400 MHz, $CDCl_3$): δ 7.41-7.39 (m, 2H), 7.34-7.31 (m, 2H), 7.26-7.23 (m, 1H), 4.17-4.12 (m, 2H), 3.71-3.67 (m, 2H), 2.96-2.94 (m, 2H), 2.85-2.82 (m, 1H), 2.45-2.26 (m, 3H), 2.14-2.09 (m, 2H), 1.77-1.76 (m, 1H), 1.27-1.24 (m, 3H).

MS-ESI calc'd. [M+H]$^+$ 260, found 260.

Step 4

To a solution of thyl 3-benzyl-3-azabicyclo[3.2.0]heptane-1-carboxylate 55e (130 mg, 0.5 mmol) in 7 mL mixed solvent of THF/EtOH/$H_2O$ (v/v/v=4/2/1) was added LiOH. $H_2O$ (63 mg, 1.5 mmol). The resulting mixture was stirred at 40° C. for 6 h, cooled down to 0° C., adjusted to pH 2 using 6 N hydrochloric acid, and added 30 mL brine. The aqueous layer was extracted with mixed solvents of EtOAc/THF (v/v=4/1, 100 mL×3). The combined organic layers were washed with water (100 mL×2), brine (100 mL×2) successively, dried over anhydrous $Na_2SO_4$, filtered. The filtrate was concentrated under reduced pressure to give crude product 3-benzyl-3-azabicyclo[3.2.0]heptane-1-carboxylic acid 55f (30 mg, white solid, yield: 95%) which was used directly without purification.

1H NMR (400 MHz, DMSO-d6): δ 11.01 (brs, 1H), 7.62-7.47 (m, 5H), 4.45 (s, 2H), 2.44-2.42 (m, 7H), 2.19-1.92 (m, 2H).

MS-ESI calc'd. [M+H]$^+$ 232, found 232.

Step 5

A solution of 3-benzyl-3-azabicyclo[3.2.0]heptane-1-carboxylic acid 55f (50 mg, 0.22 mmol), N,N-diisopropylethylamine (56 mg, 0.43 mmol) and diphenyl phosphorazidate (65 mg, 0.24 mmol) in 2 mL tertiary butanol was stirred at 40° C. for 2 h and 80° C. for 12 h. The reaction mixture was cooled down to room temperature, diluted with 50 mL brine, extracted by EtOAc (100 mL×3). The combined organic layers were washed by 100 mL water and 100 mL brine in sequence, dried over anhydrous Na₂SO₄, and filtered. The filtrate was concentrated under reduced pressure to give tert-butyl (3-benzyl-3-azabicyclo[3.2.0]heptan-1-yl)carbamate 55g (20 mg, white solid, yield: 31%) which used directly without purification.

MS-ESI calc'd. [M+H]⁺ 303, found 303.

Step 6

To a solution of tert-butyl (3-benzyl-3-azabicyclo[3.2.0]heptan-1-yl)carbamate 55g (20 mg, 0.066 mmol) in 5 mL THF was added Pd(OH)₂/C (5 mg, 20% wt) under N₂ atmosphere. The reaction mixture was stirred under H₂ (40 psi) atmosphere at 30° C. for 48 h, cooled down to room temperature and filtered. The filtrate was concentrated under reduced pressure to give tert-butyl 3-azabicyclo[3.2.0]heptan-1-ylcarbamate 55 h (10 mg, white solid, yield: 71%) which used directly without purification.

MS-ESI calc'd. [M+H]⁺ 213, found 213.

Step 7

From tert-butyl 3-azabicyclo[3.2.0]heptan-1-ylcarbamate 55 h (20 mg, 0.094 mmol) and isoquinoline-5-sulfonyl chloride 1c (22 mg, 0.094 mmol), the compound tert-butyl (3-(isoquinolin-5-ylsulfonyl)-3-azabicyclo[3.2.0]heptan-1-yl)carbamate 55I was made following the procedure described in example 1. (15 mg, white solid, yield: 40%). It was used directly without purification.

MS-ESI calc'd. [M+H]⁺ 404, found 404.

Step 8

To a solution of (3-(isoquinolin-5-ylsulfonyl)-3-azabicyclo[3.2.0]heptan-1-yl)carbamate 55I (30 mg, 0.074 mmol) in 3 mL anhydrous dichloromethane was added TFA (0.5 mL in 1 mL dichloromethane) dropwisely at 0° C. under N₂ atmosphere. The resulting mixture was stirred for 3 h until starting material disappeared, diluted with 50 mL dichloromethane, washed with saturated aq. NaHCO₃ (50 mL×3), brine (50 mL) successively, dried over anhydrous Na₂SO₄ and filtered. The filtrate was concentrated under reduced pressure and purified by prep. HPLC to give 3-(isoquinolin-5-ylsulfonyl)-3-azabicyclo[3.2.0]heptan-1-amine 55 (3 mg, white solid, yield: 13%).

¹H NMR (400 MHz, CD₃OD): δ 9.49 (s, 1H), 8.76-8.74 (m, 1H), 8.70-8.68 (m, 1H), 8.56-8.53 (m, 2H), 7.96-7.92 (m, 1H), 3.84-3.82 (m, 1H), 3.56-3.54 (m, 1H), 3.15-3.11 (m, 1H), 2.99-2.96 (m, 1H), 2.31-2.21 (m, 3H), 1.65-1.63 (m, 1H), 1.39-1.38 (m, 1H).

MS-ESI calc'd. [M+H]⁺ 304, found 304.

Example 56

3-(isoquinolin-5-ylsulfonyl)-3-azabicyclo[3.1.0]hexan-1-amine

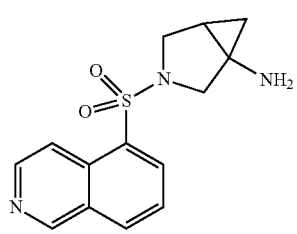 [SMILES: NC12CC1CN(S(=O)(=O)c1cccc3cnccc13)C2]

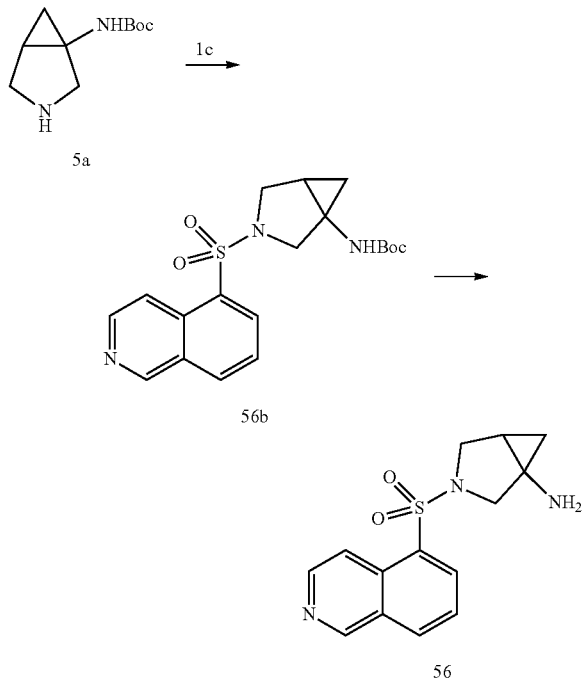

Step 1

From tert-butyl 3-azabicyclo[3.1.0]hexan-1-ylcarbamate 56a (50 mg, 0.25 mmol) and isoquinoline-5-sulfonyl chloride 1c (75 mg, 0.25 mmol, example 1), the compound tert-butyl (3-(isoquinolin-5-ylsulfonyl)-3-azabicyclo[3.1.0]hexan-1-yl) carbamate 56b was made following the procedure described in example 1. (80 mg, yellow oil, yield: 82%).

MS-ESI calc'd. [M+H]⁺ 390, found 390.

Step 2

The compound 3-(isoquinolin-5-ylsulfonyl)-3-azabicyclo[3.1.0]hexan-1-amine 56 was made from tert-butyl (3-(isoquinolin-5-ylsulfonyl)-3-azabicyclo[3.1.0]hexan-1-yl) carbamate 56b (30 mg, 0.077 mmol) following the procedure described in example 1. (7 mg, yellow solid, yield: 29%).

¹H NMR (400 MHz, D₂O): δ 9.70 (s, 1H), 8.90-8.85 (m, 1H), 8.75-8.70 (m, 1H), 8.65-8.60 (m, 1H), 8.60-8.55 (m, 1H), 8.05-8.00 (m, 1H), 3.82-3.80 (m, 1H), 3.53-3.47 (m, 1H), 3.45-3.36 (m, 2H), 1.95-1.87 (m, 1H), 1.15-1.13 (m, 1H), 0.83-0.77 (m, 1H).

MS-ESI calc'd. [M+H]⁺ 290, found 290.

Example 57

N-ethyl-3-(isoquinolin-5-ylsulfonyl)-3-azabicyclo[3.1.0]hexan-1-amine

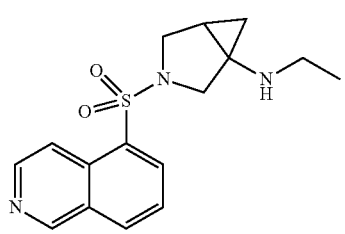 [SMILES: CCNC12CC1CN(S(=O)(=O)c1cccc3cnccc13)C2]

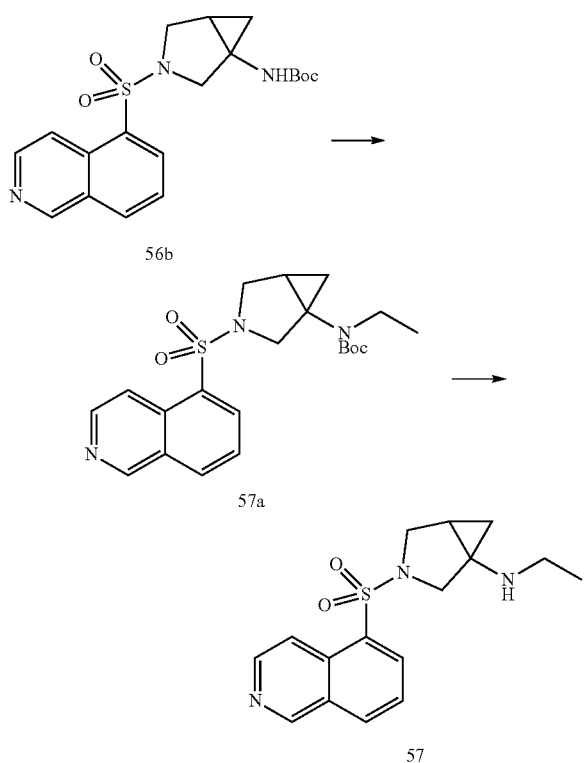

Step 1

The compound tert-butyl ethyl(3-(isoquinolin-5-ylsulfonyl)-3-azabicyclo[3.1.0]hexan-1-yl)carbamate 57a was made from tert-butyl (3-(isoquinolin-5-ylsulfonyl)-3-azabicyclo[3.1.0]hexan-1-yl) carbamate 56b (50 mg, 0.13 mmol) following the procedure described in example 11. (33 mg, yellow oil, yield: 62%).

MS-ESI calc'd. [M+H]$^+$ 418, found 418.

Step 2

The compound N-ethyl-3-(isoquinolin-5-ylsulfonyl)-3-azabicyclo[3.1.0]hexan-1-amine 57 was made from tert-butyl ethyl(3-(isoquinolin-5-ylsulfonyl)-3-azabicyclo[3.1.0]hexan-1-yl)carbamate 57a (33 mg, 0.079 mmol) following the procedure described in example 1. (10 mg, yellow solid, yield: 40%).

$^1$H NMR (400 MHz, D$_2$O): δ 9.59 (s, 1H), 8.71 (d, J=6.8 Hz, 1H), 8.63-8.54 (m, 3H), 7.96 (d, J=8.0 Hz, 1H), 3.88 (d, J=9.2 Hz, 1H), 3.54-3.41 (m, 3H), 3.09-2.99 (m, 2H), 2.05-2.00 (m, 1H), 1.25 (t, J=8.4 Hz, 1H), 1.14 (t, J=7.2 Hz, 3H), 0.90-0.85 (m, 1H).

MS-ESI calc'd. [M+H]$^+$ 318, found 318.

Biological Activity Experiment: In Vitro ROCK Kinase Inhibition Activity Evaluation Experimental Objective: Test ROCK Inhibition IC50 Value of Invented Compounds Material:

Buffer solution: 20 mM Hepes (pH 7.5), 10 mM MgCl2, 1 mM EGTA, 0.02% Brij35, 0.02 mg/ml BSA, 0.1 mM Na3VO4, 2 mM DTT, 1% DMSO Procedure:

To a freshly prepared buffer solution was added ROCK substrate Long S6 Kinase substrate peptide, with concentration at 20 μM. 1 nM ROCK kinase was then added, and well stirred. A series of DMSO solution (starting from 10 μM, dilution factor 3) of testing article was added using Echo550. The mixture was incubated for 20 min at room temperature, then was added $^{33}$P-ATP (radioactive intensity 10 μCi/μL) to initiate reaction and further reacted for 2 h at room temperature. The mixture was filtered through P81 ion exchange paper (Whatman #3698-915), and washed by 0.75% phosphoric acid. The intensity of radiation was measured by Filter-Binding method.

The inhibition activity of the testing articles were measured by comparing the residue kinase activity to blank substrate (pure DMSO). Using Prism software ((GraphPad Software, San Diego Calif., USA) to calculate IC50 and curve.

EXPERIMENT RESULTS

TABLE 1

| ROCK kinase inhibition activity test result | |
|---|---|
| Test article (each invented compound) | ROCK inhibition activity |
| Example 1 | ++ |
| Example 2 | ++ |
| Example 3 | ++ |
| Example 4 | ++ |
| Example 5 | ++ |
| Example 6 | ++ |
| Example 7 | ++ |
| Example 8 | ++ |
| Example 9 | + |
| Example 10 | -- |
| Example 11 | -- |
| Example 12/12' | ++/++ |
| Example 13 | +++ |
| Example 14 | ++ |
| Example 15 | ++ |
| Example 16 | ++ |
| Example 17 | ++ |
| Example 18 | ++ |
| Example 19 | +++ |
| Example 20 | ++ |
| Example 21 | ++ |
| Example 22 | ++ |
| Example 23 | ++ |
| Example 24 | + |
| Example 25 | ++ |
| Example 26 | ++ |
| Example 27 | ++ |
| Example 28 | ++ |
| Example 29 | ++ |
| Example 30 | ++ |
| Example 31 | -- |
| Example 32 | -- |
| Example 33 | -- |
| Example 34 | -- |
| Example 35 | -- |
| Example 36 | -- |
| Example 37 | ++ |
| Example 38 | +++ |
| Example 39 | ++ |
| Example 40 | +++ |
| Example 41 | +++ |
| Example 42 | +++ |
| Example 43 | +++ |
| Example 44 | +++ |
| Example 45 | + |
| Example 46 | -- |
| Example 47 | + |
| Example 48 | + |
| Example 49 | + |
| Example 50 | + |
| Example 51 | + |
| Example 52 | + |
| Example 53 | + |
| Example 54 | + |
| Example 55 | + |

TABLE 1-continued

ROCK kinase inhibition activity test result

| Test article (each invented compound) | ROCK inhibition activity |
|---|---|
| Example 56 | ++ |
| Example 57 | + |

Note:
1 µM ≤ + < 5 µM;
0.1 µM ≤ ++ < 1 µM;
+++ < 0.1 µM;
-- N/A

Conclusion: the invented compounds have significant and unexpected kinase inhibition activity.

What is claimed is:

1. A compound of formula (I) or a pharmaceutically acceptable salt thereof,

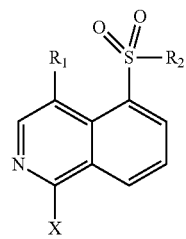
(I)

wherein, $R_1$, and X are separately and independently selected from the group consisting of H, F, Cl, Br, I, CN, OH, $NH_2$, $C_{1-3}$ alkyl, $C_{1-3}$ alkoxy, $C_{1-3}$ alkylamino and N,N-di($C_{1-3}$alkyl)amino, wherein the $C_{1-3}$ alkyl is substituted or unsubstituted by $R_{01}$;

$R_2$ is

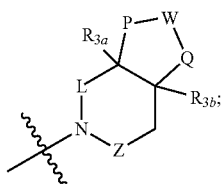

W is $N(R_{w1})$, or $C(R_{w2})(R_{w3})$;
L is $C(R_{z1})(R_{z2})$;
Z is a single bond or $C(R_{z1})(R_{z2})$;
P is $(CH_2)_{q1}$;
Q is $(CH_2)_{q2}$;
$q_1$ is 0, 1, 2, 3 or 4;
$q_2$ is 0, 1, 2, 3 or 4;
$R_{3a}$, $R_{3b}$, $R_{w1}$, $R_{w2}$, $R_{w3}$, $R_{z1}$, $R_{z2}$ are separately and independently selected from the group consisting of H, F, Cl, Br, I, OH, $C_{1-3}$alkyl and $NH_2$;
$R_{01}$ is selected from the group consisting of F, Cl, Br, I, OH, $NH_2$, the number of $R_{01}$ is 1, 2 or 3.

2. The compound of claim 1 or a pharmaceutically acceptable salt thereof, wherein $R_1$ is selected from the group consisting of H, F, Cl, Br, I, methyl, difluoromethyl, trifluoromethyl and methoxyl; X is selected from the group consisting of H and OH.

3. The compound of claim 2 or a pharmaceutically acceptable salt thereof, wherein the moiety of

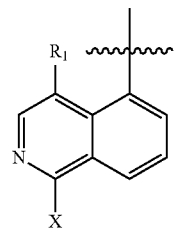

is selected from the group consisting of

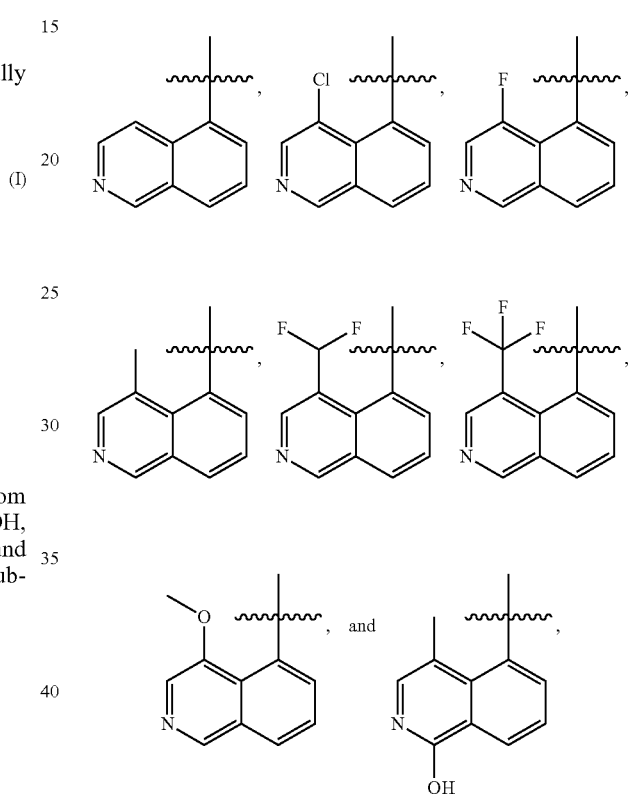

4. The compound of claim 1 or a pharmaceutically acceptable salt thereof, wherein $R_2$ is selected from the group consisting of

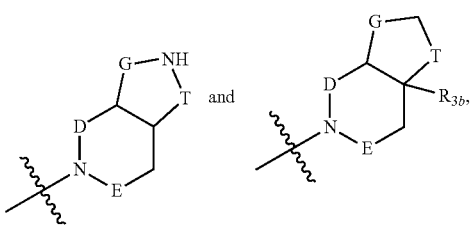

in which E is single bond, and D is methylene; G is elected from $(CH_2)_g$; T is selected from $(CH_2)_t$; g is selected from 0, 1, 2, 3 and 4, t is selected from the group consisting of 0, 1, 2, 3 and 4; $R_{3b}$ is the same as defined in claim 1.

5. A compound of formula (I) or a pharmaceutically acceptable salt thereof,

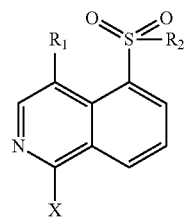

(I)

wherein,

R₁, X are separately and independently selected from the group consisting of H, F, Cl, Br, I, CN, OH, NH$_2$, C$_{1-3}$alkyl, C$_{1-3}$alkoxy, C$_{1-3}$ alkylamino and N,N-di(C$_{1-3}$alkyl)amino, wherein the C$_{1-3}$alkyl is optionally substituted by R$_{01}$;

R$_{01}$ is selected from the group consisting of F, Cl, Br, I, OH, NH$_2$, the number of R$_{01}$ is 1, 2 or 3;

R$_2$ is

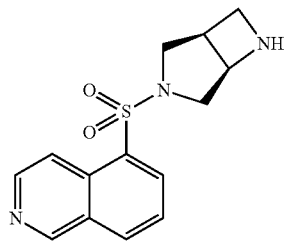

in which, Y is selected from (CH$_2$)$_y$; M is selected from (CH$_2$)$_m$; y is selected from the group consisting of 1, 2 or 3; m is 0 or 1.

6. A compound or a pharmaceutically acceptable salt thereof, wherein the compound is selected from the group consisting of

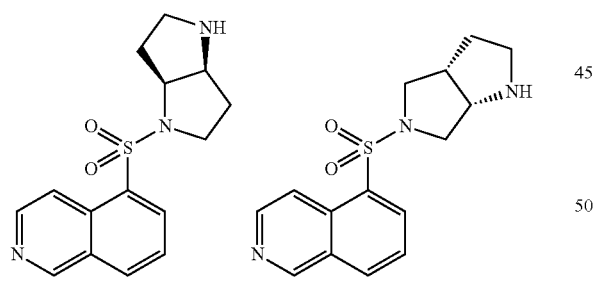

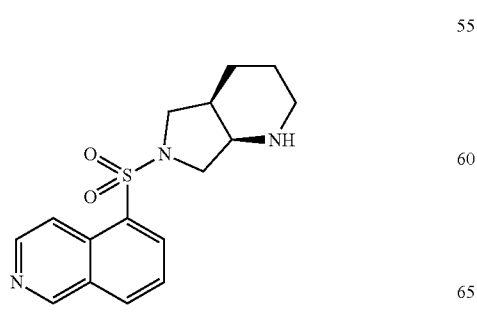

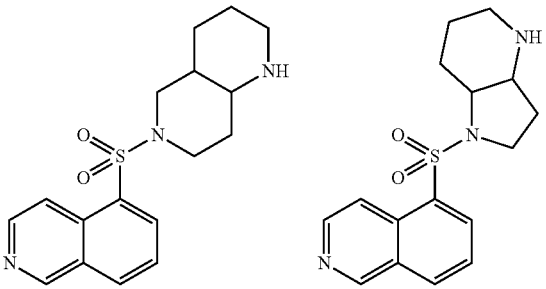

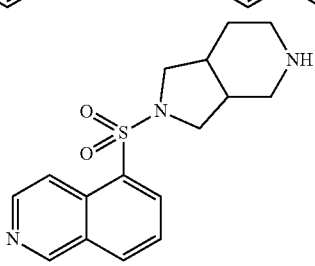

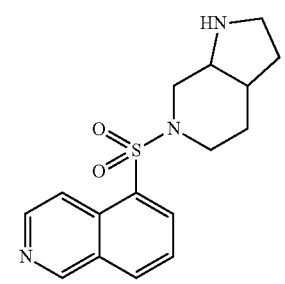 [SMILES: O=S(=O)(c1cccc2cnccc12)N1CCC2CCNC2C1]

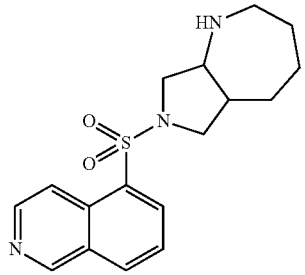

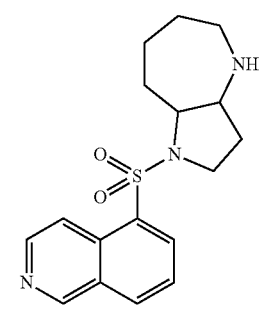

-continued
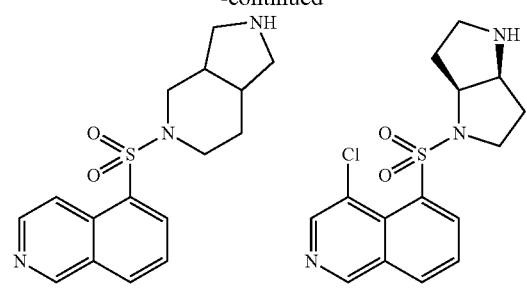
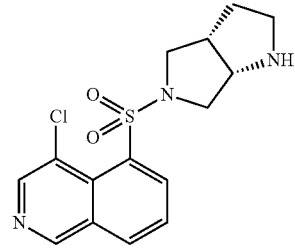
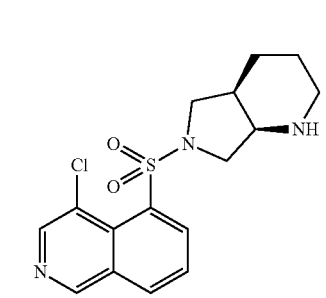
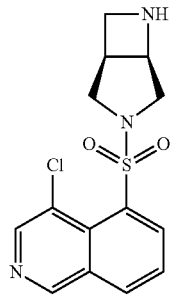
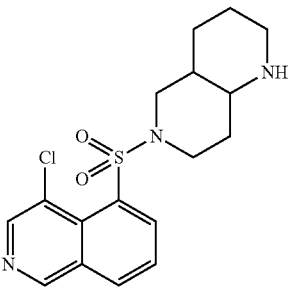
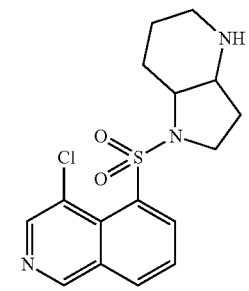
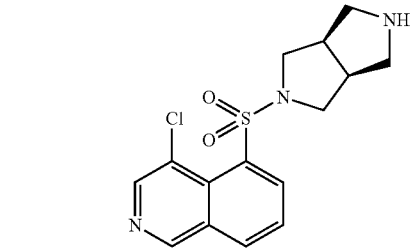
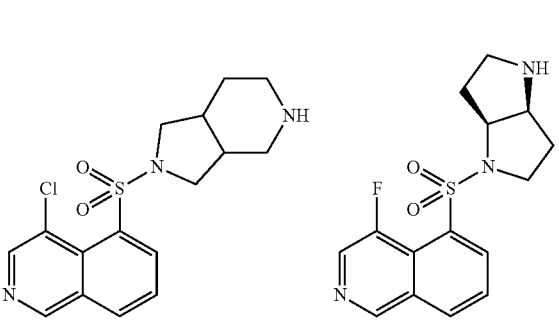
-continued
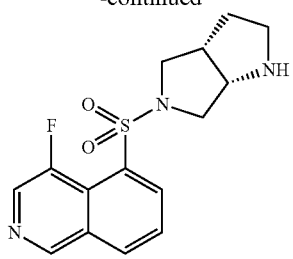
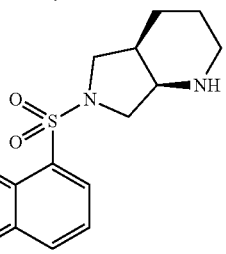
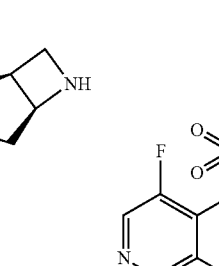
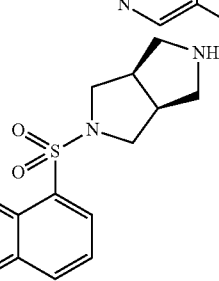
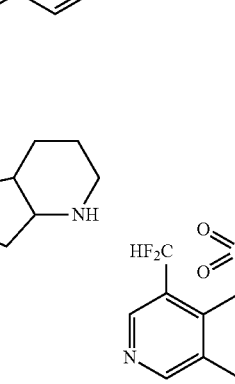
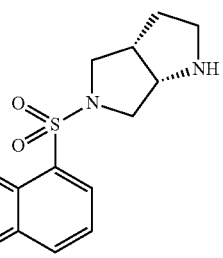

121
-continued
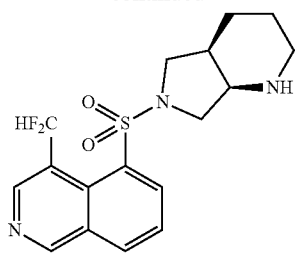
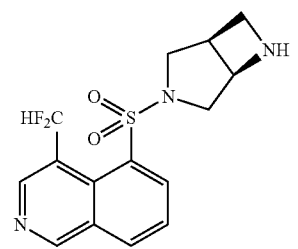
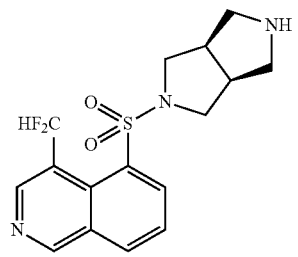
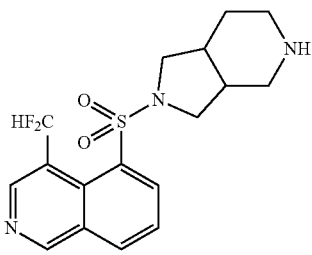
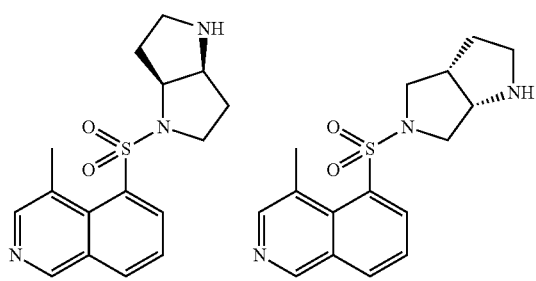
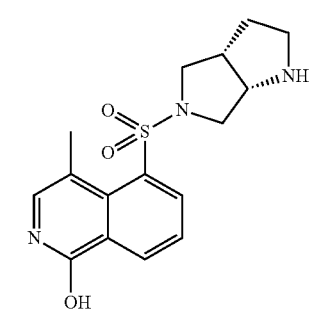
122
-continued
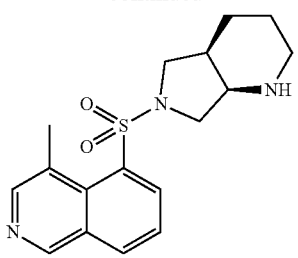
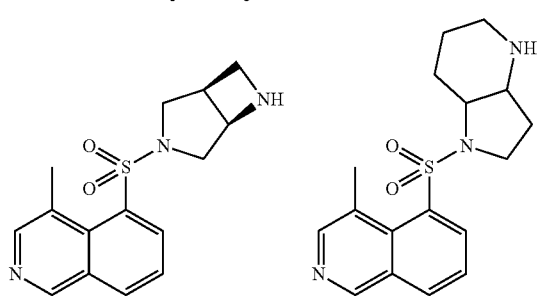
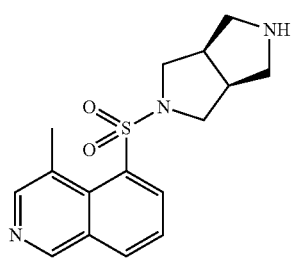
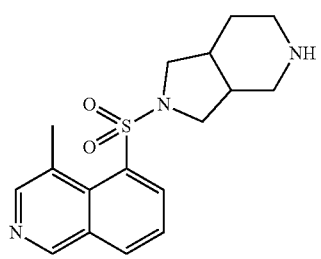
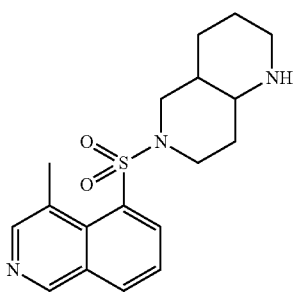
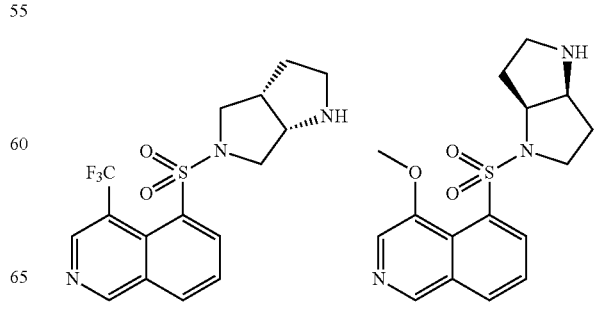

-continued

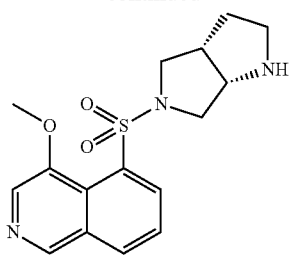
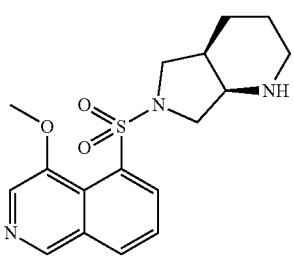
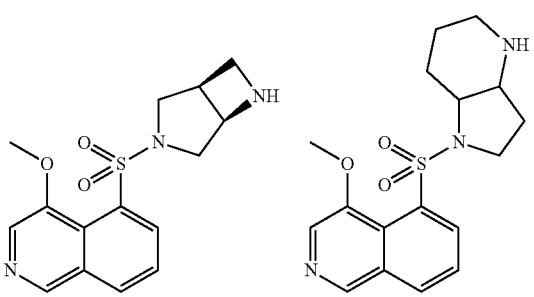
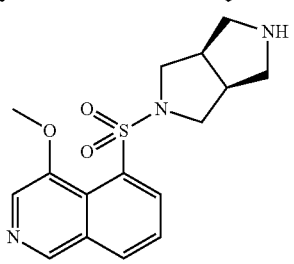
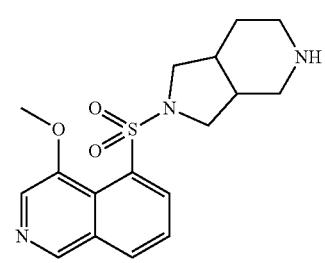
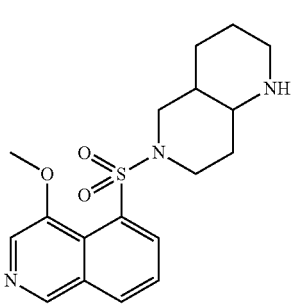

-continued

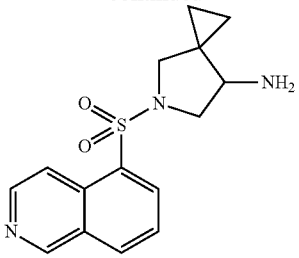
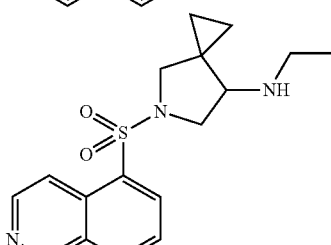
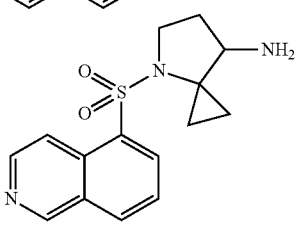
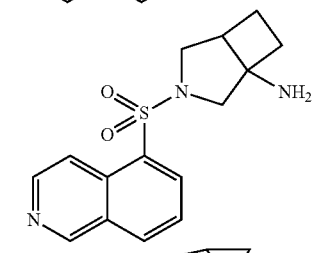
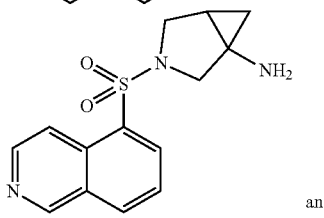

and

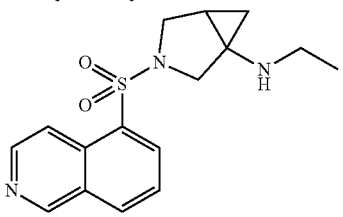

7. A pharmaceutical composition comprising therapeutically effective amount of the compound of formula (I) or a pharmaceutically acceptable salt thereof according to claim 1 and pharmaceutical acceptable carriers.

8. A method for preventing or treating various diseases caused by vasoconstriction, in which the diseases include cerebral embolism, cerebral ischemia, cerebral injury, vertebrobasilar insufficiency, cerebral angiospasm caused by subarachnoid hemorrhage, angina, glaucoma, hypertension and fibrosis, in a subject in need thereof, comprising: administering an effective amount of the compound of formula (I) or a pharmaceutically acceptable salt thereof according to claim 1 to the subject.

9. The compound of claim 4 or a pharmaceutically acceptable salt thereof, wherein g is 1, 2, 3 or 4, t is 0 or 1.

10. The compound of claim 4 or a pharmaceutically acceptable salt thereof, wherein $R_{3b}$ is $NH_2$.

11. A compound of formula (I) or a pharmaceutically acceptable salt thereof,

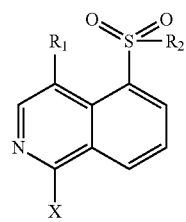
(I)

wherein, $R_1$, X are separately and independently selected from the group consisting of H, F, Cl, Br, I, CN, OH, $NH_2$, $C_{1-3}$alkyl, $C_{1-3}$alkoxy, $C_{1-3}$ alkylamino and N,N-di($C_{1-3}$alkyl)amino, wherein the $C_{1-3}$alkyl is optionally substituted by $R_{01}$;

$R_{01}$ is selected from the group consisting of F, Cl, Br, I, OH, $NH_2$, the number of $R_{01}$ is 1, 2 or 3;

$R_2$ is selected from the group consisting of

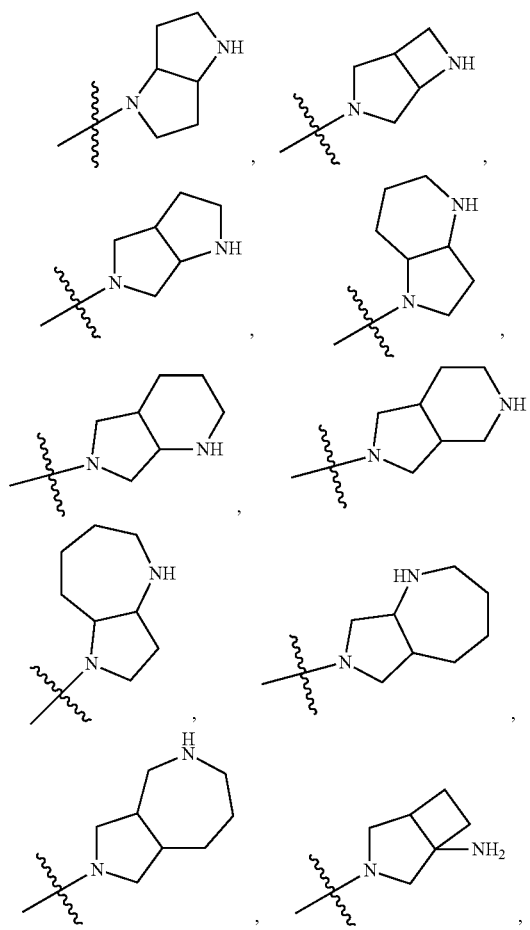

-continued

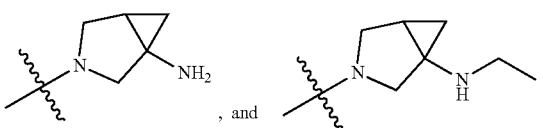
, and

12. A compound of formula (I) or a pharmaceutically acceptable salt thereof,

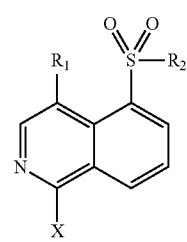

wherein, $R_1$, X are separately and independently selected from the group consisting of H, F, Cl, Br, I, CN, OH, $NH_2$, $C_{1-3}$alkyl, $C_{1-3}$alkoxy, $C_{1-3}$ alkylamino and N,N-di($C_{1-3}$alkyl)amino, wherein the $C_{1-3}$alkyl is optionally substituted by $R_{01}$;

$R_{01}$ is selected from the group consisting of F, Cl, Br, I, OH, $NH_2$, the number of $R_{01}$ is 1, 2 or 3;

$R_2$ is selected from the group consisting of

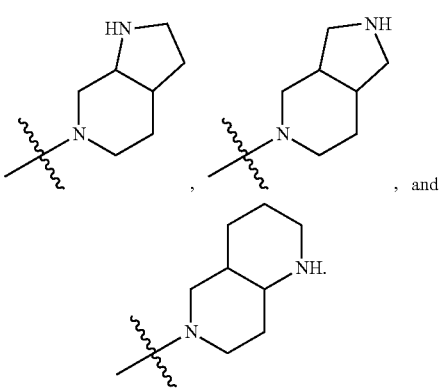

13. A method for preventing or treating various diseases caused by vasoconstriction, in which the diseases include cerebral embolism, cerebral ischemia, cerebral injury, vertebrobasilar insufficiency, cerebral angiospasm caused by subarachnoid hemorrhage, angina, glaucoma, hypertension and fibrosis, in a subject in need thereof, comprising: administering an effective amount of the pharmaceutical composition according to claim 7 to the subject.

14. The compound of claim 5 or a pharmaceutically acceptable salt thereof, wherein $R_1$ is selected from the group consisting of H, F, Cl, Br, I, methyl, difluoromethyl, trifluoromethyl and methoxyl; X is selected from the group consisting of H and OH.

15. The compound of claim 14 or a pharmaceutically acceptable salt thereof, wherein the moiety of

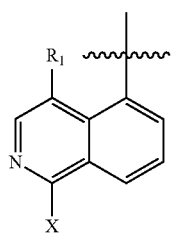

is selected from the group consisting of

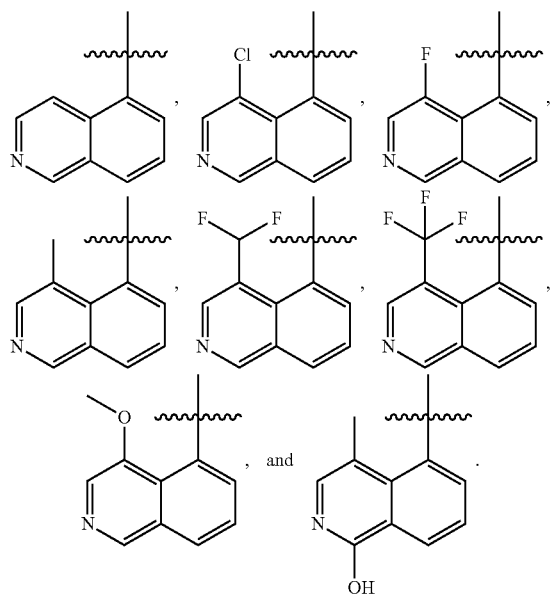

16. The compound of claim 11 or a pharmaceutically acceptable salt thereof, wherein $R_1$ is selected from the group consisting of H, F, Cl, Br, I, methyl, difluoromethyl, trifluoromethyl and methoxyl; X is selected from the group consisting of H and OH.

17. The compound of claim 16 or a pharmaceutically acceptable salt thereof, wherein the moiety of

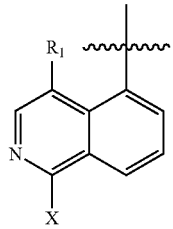

is selected from the group consisting of

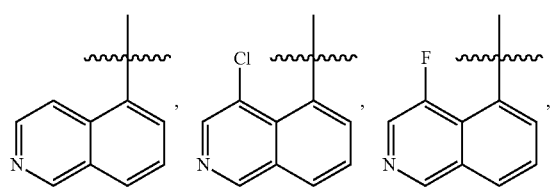

-continued

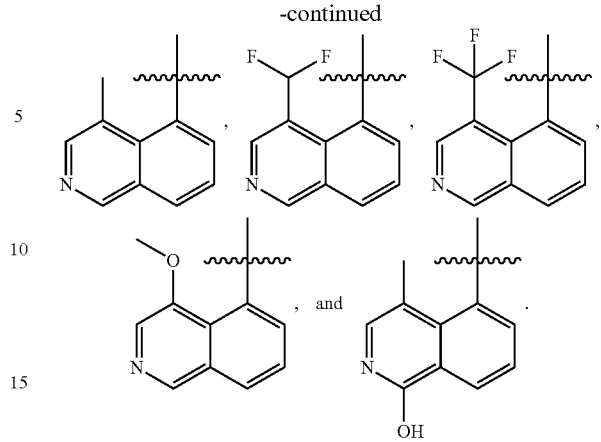

18. The compound of claim 12 or a pharmaceutically acceptable salt thereof, wherein $R_1$ is selected from the group consisting of H, F, Cl, Br, I, methyl, difluoromethyl, trifluoromethyl and methoxyl; X is selected from the group consisting of H and OH.

19. The compound of claim 18 or a pharmaceutically acceptable salt thereof, wherein the moiety of

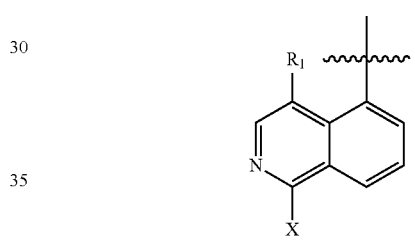

is selected from the group consisting of

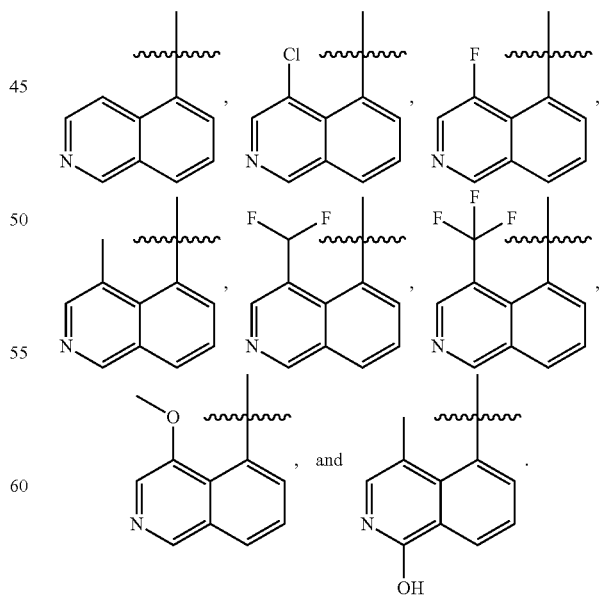

* * * * *